(12) United States Patent
Habashita et al.

(10) Patent No.: US 7,511,159 B2
(45) Date of Patent: Mar. 31, 2009

(54) AZETIDINE RING COMPOUNDS AND DRUGS COMPRISING THE SAME

(75) Inventors: Hiromu Habashita, Mishima-gun (JP); Haruto Kurata, Mishima-gun (JP); Shinji Nakade, Tsukuba (JP); Takeji Ono, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/584,435

(22) PCT Filed: Dec. 24, 2004

(86) PCT No.: PCT/JP2004/019400

§ 371 (c)(1), (2), (4) Date: Aug. 15, 2006

(87) PCT Pub. No.: WO2005/063704

PCT Pub. Date: Jul. 14, 2005

(65) Prior Publication Data

US 2007/0135402 A1    Jun. 14, 2007

(30) Foreign Application Priority Data

Dec. 25, 2003 (JP) .............................. 2003-429948

(51) Int. Cl.
*C07D 205/00* (2006.01)
*A01N 43/00* (2006.01)

(52) U.S. Cl. .................. 548/953; 514/210.01

(58) Field of Classification Search ................. 548/953; 514/210.01
See application file for complete search history.

(56) References Cited

U.S. PATENT DOCUMENTS

| | | | |
|---|---|---|---|
| 5,849,780 A | 12/1998 | Di Malta et al. | |
| 6,335,324 B1 | 1/2002 | Bisacchi et al. | |

FOREIGN PATENT DOCUMENTS

| | | |
|---|---|---|
| EP | 0 560 613 | 9/1993 |
| EP | 1 522 314 | 4/2005 |
| EP | 1 719 762 | 11/2006 |
| EP | 1 719 763 | 11/2006 |
| JP | 6-41131 | 2/1994 |
| JP | 2004-277320 | 10/2004 |
| WO | WO 9967215 | * 6/1999 |
| WO | 99/67215 | 12/1999 |
| WO | 2004/002531 | 1/2004 |
| WO | WO 2004002531 | * 1/2004 |
| WO | 2004/039814 | 5/2004 |
| WO | WO 2004039814 | * 5/2004 |
| WO | 2004/112793 | 12/2004 |
| WO | 2005/051391 | 6/2005 |
| WO | 2006/004195 | 1/2006 |
| WO | 2006/030984 | 3/2006 |
| WO | 2006/038001 | 4/2006 |
| WO | 2006/047196 | 5/2006 |
| WO | 2006/068594 | 6/2006 |

OTHER PUBLICATIONS

Soga et al. Mackenzie et al. Bioorganic and Medicinal chemistry Letters, 2003 13, 2211-2215.*
Office Action issued in European Application No. 04 807 756.4 Dec. 3, 2008.

* cited by examiner

*Primary Examiner*—D. Margaret Seaman
*Assistant Examiner*—Nizal S Chandrakumar
(74) *Attorney, Agent, or Firm*—Wenderoth, Lind & Ponack, L.L.P.

(57) ABSTRACT

It is intended to provide compounds having EDG-5 antagonism. Because of having EDG-5 antagonism, compounds of the formula (I):

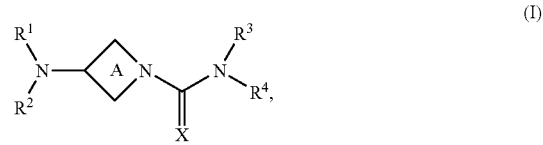

wherein each symbol is as defined in the description; salts thereof, N-oxides thereof, solvates thereof or prodrugs thereof are useful as preventive and/or therapeutic agent for EDG-5 mediated diseases, for example, diseases caused by blood vessel contraction (e.g. cerebrovascular spasms disease, cardiovascular spasms diseases, coronary artery spasms disease, hypertension, pulmonary hypertension, renal diseases, myocardial infarction, angina pectoris, arrhythmia, portal hypertension, varicosity and the like), arteriosclerosis, pulmonary fibrosis, hepatic fibrosis, renal fibrosis, respiratory diseases (e.g. bronchial asthma, chronic obstructive pulmonary diseases and the like), nephropathy, diabetes, hyperlipemia and the like.

5 Claims, No Drawings

AZETIDINE RING COMPOUNDS AND DRUGS COMPRISING THE SAME

This application is a U.S. national stage of International Application No. PCT/JP2004/019400 filed Dec. 24, 2004.

TECHNICAL FIELD

The present invention relates to an azetidine ring compound, which is useful as a pharmaceutical.

BACKGROUND ART

It has been proposed that sphingosine-1-phosphate [(2S, 3R,4E)-2-amino-3-hydroxyoctadec-4-enyl-1-phosphate; hereinafter optionally referred to as S1P], which is a lipid synthesized through intracellular metabolic turnover of sphingolipids and with the activity of an extracellular secretory sphingosine kinase, acts as an intracellular messenger and as an intracellular second messenger.

Recently, cloning of S1P receptor has made remarkable progresses, and as a result, it has been reported that the G-protein coupled receptors of EDG-1 ($S1P_1$), EDG-3 ($S1P_3$), EDG-5 ($AGR16/H218/S1P_2$), EDG-6 (S1P4) and EDG-8 ($S1P_5$) are the specific S1P receptors.

With particular reference to EDG-5, it has been reported that the mRNA expression is strongly recognized in the tissues of the heart, lungs, stomach, and small intestine, and that in the arterial sclerosis model of coronary artery, or the mice carotid balloon injury model, the mRNA expression level in the intima cells significantly decreases as compared with the normal ones [see the specification of JP-A 6-234797].

It is also reported that the S1P receptor (especially EDG-5) is involved in the increased portal vein pressure, asthma and the like (see *Biochem. Biophys. Res. Commun.,* 2004, 320(3), 754-759, *Mol. Immunol.,* 2002, 38(16-18), 1239-1245 and *FASEB J.,* 2003, 17(13), 1789-1799).

It is disclosed that the pyrazopyridine compound of the formula (a):

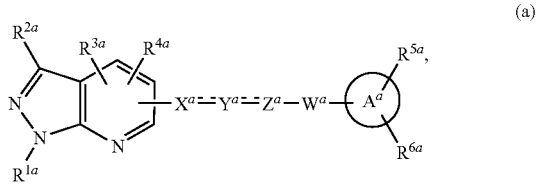

wherein $R^{1a}$, $R^{2a}$ and $R^{3a}$ each represent C1-8 alkyl and the like; $R^{4a}$ represents hydrogen and the like; $R^{5a}$ and $R^{6a}$, being the same or different, individually represent hydrogen, C1-8 alkyl, C1-6 alkoxy, halogen and the like; $X^a$ represents —NH—, —O—, —$CH_2$— and the like; $Y^a$ is —NH— and the like; $Z^a$ represents —CO— and the like; $W^a$ represents —NH— and the like; ring $A^a$ is aryl, heteroaryl and the like; (essence was quoted) or a pharmaceutically acceptable salt thereof acts on EDG-5 specifically, and is useful as a treating agent for fibrosis (see WO 01/98301 pamphlet).

And it is also disclosed that the N-containing compound of the formula (b):

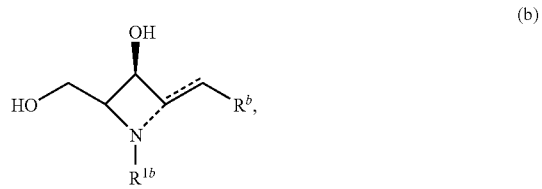

wherein $R^{1b}$ is an optionally substituted —$C_{nb}H_{(2nb-2mb)}CH_3$ or optionally substituted aryl; $R^{2b}$ is hydrogen, alkyl or alkylcarbonyl (essence was quoted) or a pharmaceutically acceptable salt antagonizes the EDG receptor (see WO 03/040097 pamphlet).

DISCLOSURE OF THE INVENTION

Problems to be Solved by the Invention

The EDG-5 antagonist is useful for the prevention and/or treatment of EDG-5-mediated diseases, such as diseases caused by blood vessel contraction (e.g. cerebrovascular spasmodic disease, cardiovascular spasmodic disease, coronary artery spasm, hypertension, pulmonary hypertension, renal disease, cardiac infarction, angina pectoris, arrhythmia, portal hypertension, varicosity and the like), arteriosclerosis, pulmonary fibrosis, hepatic fibrosis, renal fibrosis, respiratory diseases (e.g. bronchial asthma, chronic obstructive pulmonary disease and the like), nephropathy, diabetes, hyperlipidemia and the like, and the development of an excellent EDG-5 antagonist has therefore been strongly demanded.

Means for Solving the Problems

The present inventors have conducted extensive investigation in order to find out a compound which antagonizes EDG-5 and is useful as a pharmaceutical drug, and as a result, have found that the compound of the formula (I) has an excellent antagonistic effect against EDG-5, thereby leading to completion of the present invention. The compound of the formula (I) has an antagonistic effect against EDG-5 and is therefore useful as a preventive and/or therapeutic agent for the diseases induced by EDG-5.

DETAILED DESCRIPTION OF THE PRESENT INVENTION

Namely, the present invention relates to:
[1] a compound of the formula (I):

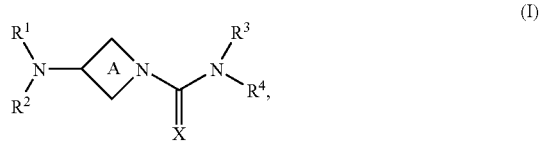

wherein ring A is an azetidine ring which may have further substituent(s); X is oxygen, sulfur or nitrogen which may have substituent(s); $R^1$, $R^2$, $R^3$ and $R^4$ are each independently hydrogen, a hydrocarbon group which may have substituent(s), —$SO_2R^5$ or a heterocyclic ring which may have substituent(s); $R^5$ is a hydrocarbon group which may have substituent(s); $R^1$ and $R^2$, and $R^3$ and $R^4$ may be taken together to form an N-containing heterocyclic ring group which may have further substituent(s), a salt thereof, an N-oxide thereof, a solvate thereof, or a prodrug thereof,

[2] the compound according to the above item [1], wherein X is oxygen,

[3] the compound according to the above item [1], wherein $R^1$, $R^2$, $R^3$ and $R^4$ are each independently hydrogen, a hydrocarbon group which may have substituent(s), or a heterocyclic ring group which may have substituent(s),

[4] the compound according to the above item [1], which is a compound of the formula (I-1):

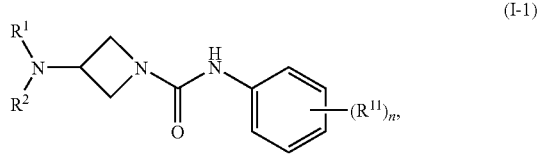

wherein $R^1$ and $R^2$ are each independently hydrogen, a hydrocarbon group which may have substituent(s), —$SO_2R^5$ or a heterocyclic ring group which may have substituent(s); $R^5$ is a hydrocarbon group which may have substituent(s); $R^1$ and $R^2$ are taken together with the adjacent nitrogen atom to form an N-containing heterocyclic ring group which may have substituent(s); $R^{11}$ is any arbitrary substituent(s); and n is 0 or an integer of 1-5, with the proviso that when n is 2 or more, the plural $R^{11}$s may be the same or different,

[5] the compound of the above item [1] or [4] wherein $R^1$ and $R^2$ are taken together with the adjacent nitrogen atom to form an N-containing heterocyclic ring group which may further have substituent(s),

[6] the compound according to the above item [1] or [5] wherein the N-containing heterocyclic ring group is a piperidine, piperazine or indoline ring,

[7] the compound according to the above item [1] or [4], wherein $R^1$ is a benzene ring which may have substituent(s),

[8] the compound according to the above item [1], which is selected from the group consisting of N-(3,5-dichlorophenyl)-3-(4-phenylpiperidin-1-yl)azetidine-1-carboxamide, 3-(2,3-dihydro-1H-indol-1-yl)-N-[3-(trifluoromethyl)phenyl]azetidine-1-carboxamide, N-(3,5-dichlorophenyl)-3-(2,3-dihydro-1H-indol-1-yl)azetidine-1-carboxamide, N-[3,5-bis(trifluoromethyl)phenyl]-3-(2,3-dihydro-1H-indol-1-yl)-azetidine-1-carboxamide, 3-(2,3-dihydro-1H-indol-1-yl)-N-(3-phenoxyphenyl)-azetidine-1-carboxamide, N-[3,5-bis(trifluoromethyl)phenyl]-3-[methyl(phenyl)-amino] azetidine-1-carboxamide and N-[3,5-bis(trifluoromethyl)phenyl]-3-[ethyl-(phenyl)amino]azetidine-1-carboxamide,

[9] a pharmaceutical composition comprising the compound of the formula (I), a salt thereof, an N-oxide, a solvate thereof or a prodrug thereof described in the above item [1],

[10] the pharmaceutical composition according to the above item [9], which is an S1P receptor antagonist,

[11] the pharmaceutical composition according to the above item [10], which is an EDG-5 antagonist,

[12] the pharmaceutical composition according to the above item [9], which is a preventive and/or therapeutic agent for the diseases induced by blood vessel contraction,

[13] the pharmaceutical composition according to the above item [12], wherein the diseases induced by blood vessel contraction include cerebrovascular spasms disease, hypertension, pulmonary hypertension, myocardial infarction, angina pectoris, and portal hypertension,

[14] the pharmaceutical composition according to the above item [9], which is a preventive and/or therapeutic agent for respiratory diseases,

[15] the pharmaceutical composition according to the above item [14] wherein the respiratory diseases include bronchial asthma and chronic obstructive pulmonary disease,

[16] a medicament comprising a combination of the compound of the formula (I), a salt thereof, an N-oxide thereof, a solvate thereof or a prodrug thereof described in the above item [1], and one or more member(s) selected from the group consisting of a calcium antagonist, a thrombolytic agent, a thromboxane synthase inhibitor, an endothelin antagonist, an antioxidant agent, a radical scavenger, a poly-ADP ribose polymerase inhibitor, an astrocyte-function improvement agent, a vasodilating agent and an Rho kinase inhibitor,

[17] a method for the prevention and/or treatment of an EDG-5 mediated disease in a mammal, characterized by administering to a mammal an effective dose of the compound of the formula (I), a salt thereof, an N-oxide thereof, a solvate thereof or a prodrug thereof,

[18] use of the compound of the formula (I), a salt thereof, an N-oxide thereof, a solvate thereof or a prodrug thereof described in the above item [1] for the manufacture of the preventive and/or therapeutic agent for EDG-5-mediated diseases, and

[19] a method for the preparation of the compound of the formula (I), a salt thereof, an N-oxide thereof or a prodrug thereof described in the above item [1].

Effect of the Invention

The compound of the present invention has an excellent EDG-5 antagonistic effect. It is therefore useful for the prevention and/or treatment of the diseases caused by, for example, blood vessel contraction (e.g. cerebrovascular spasmodic disease, cardiovascular spasmodic disease, coronary artery spasm, hypertension, pulmonary hypertension, renal disease, cardiac infarction, angina pectoris, arrhythmia, portal hypertension, varicosity and the like), arteriosclerosis, pulmonary fibrosis, hepatic fibrosis, renal fibrosis, respiratory diseases (e.g. bronchial asthma, chronic obstructive pulmonary disease and the like), nephropathy, diabetes, hyperlipidemia and the like.

BEST MODE FOR CARRYING OUT THE INVENTION

Referring now to the formula (I), the ring A may have optional substituent(s). Such optional substituents in a number of 1 to 5, preferably 1 to 3, may occupy any positions susceptible to substitution. Examples of such substituents on the ring A include (1) a hydrocarbon group which may have substituent(s), (2) a heterocyclic ring which may have substituent(s), (3) a C1-4 alkylsulfonyl group (e.g. methylsulfonyl, ethylsulfonyl and the like), (4) a phenylsulfonyl group which may have substituent(s) (e.g. phenylsulfonyl and 4-methylbenzenesulfonyl and the like), (5) a halogen atom (e.g. fluorine, chlorine, bromine and iodine), (6) a carboxyl group, (7) a cyano group, (8) a nitro group, (9) a carbamoyl group which may have substituent(s), (10) a sulfamoyl group which may have substituent(s), (11) an alkoxycarbonyl group (e.g. C1-6 alkoxycarbonyl (e.g. methoxycarbonyl, ethoxycarbonyl and tert-butoxycarbonyl) and the like), (12) a sulfo group (—$SO_3H$), (13) a sulfino group, (14) a phosphono group, (15) an amidino group, (16) —$B(OH)_2$, (17) a C1-6 acyl group (e.g. formyl, acetyl, propionyl, butyryl and the like), (18) a benzoyl group which may have substituent(s), and the like.

Examples of the "hydrocarbon group" in the "hydrocarbon group which may have substituent(s)" on the ring A include a straight-chain or branched aliphatic hydrocarbon group, a cyclic hydrocarbon group, a cyclic hydrocarbon-aliphatic hydrocarbon group, a cyclic hydrocarbon-cyclic hydrocarbon group and the like.

Examples of the "straight-chain or branched aliphatic hydrocarbon group" include a "C1-8 aliphatic hydrocarbon group" and the like, and as the "C1-8 aliphatic hydrocarbon group", there are mentioned, for example, C1-8 alkyl (e.g. methyl, ethyl, propyl, isopropyl, butyl, sec-butyl, tert-butyl, pentyl, hexyl, heptyl, octyl and the like), C2-8 alkenyl (e.g. vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and the like), C2-8 alkynyl (e.g. ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl and the like), and the like.

Examples of the "cyclic hydrocarbon group" include the above-mentioned "saturated cyclic hydrocarbon group" and "unsaturated cyclic hydrocarbon group". The "saturated cyclic hydrocarbon group" is exemplified by cycloalkanes, such as cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane and the like, as well as frutherrmore "3-15 membered saturated hydrocarbon group", such as perhydropentalene, perhydroazulene, perhydroindene, perhydronaphthalene, perhydroheptalene, spiro[4.4]nonane, spiro[4.5]decane, spiro-[5.5]undecane, bicyclo[2.2.1]heptane, bicyclo[3.1.1]heptane, bicyclo[2.2.2]octane, adamantane or noradamantane ring and the like. Examples of the "unsaturated cyclic hydrocarbon group" include cycloalkene, such as cyclopentene, cyclohexene, cycloheptene, cyclooctene, cyclopentadiene, cyclohexadiene, cycloheptadiene, cyclooctadiene and the like, aromatic hydrocarbon, such as benzene, azulene, naphthalene, phenanthrene, anthracene and the like, and "a 3-15 membered unsaturated cyclic hydrocarbon group", such as pentalene, indene, indan, dihydro-naphthalene, tetrahydronaphthalene, heptalene, biphenylene, as-indacene, s-indacene, acenaphthene, acenaphthyrene, fluorene, phenalene, bicyclo[2.2.1]hept-2-ene, bicyclo[3.1.1]hept-2-ene or bicyclo[2.2.2]oct-2-ene and the like.

As the "cyclic hydrocarbon-aliphatic hydrocarbon group", there are mentioned, for example, a group in which the above-mentioned "cyclic hydrocarbon group" and "straight-chain or branched aliphatic hydrocarbon group" are linked mutually, such as C7-16 aralkyl (e.g. benzyl, phenylethyl, phenylpropyl, naphthalen-1-ylmethyl and the like), C8-16 aralkenyl (e.g. 3-phenyl-2-propenyl and 2-(2-naphthylvinyl)), (C3-8 cycloalkyl)-(C1-4alkyl) (e.g. cyclopropylmethyl, cyclohexylmethyl, cyclohexyl-ethyl, cyclohexylpropyl and 1-methyl-1-cyclohexylmethyl) or (C3-8 cycloalkenyl)-(C1-4 alkyl) (e.g. 3-cyclohexenylmethyl) and the like.

Examples of the "cyclic hydrocarbon-cyclic hydrocarbon group" include a group in which the above "cyclic hydrocarbon group" and "cyclic hydrocarbon group" are linked mutually, such as 2-biphenyl, 3-biphenyl, 4-biphenyl, 2-cyclohexylphenyl, 3-cyclohexylphenyl, 4-cyclohexylphenyl and the like.

In the "heterocyclic ring group which may have substituent(s)", which is a substituent on the ring A, the "heterocyclic ring" is mono-cyclic or multi-cyclic heterocyclic ring group which may have 1-7 of heteroatoms selected from nitrogen, oxygen and sulfur. Examples of the "heterocyclic ring" include "3-15 membered unsaturated mono-cyclic or multi-cyclic heterocyclic ring", "3-15 membered saturated mono-cyclic or multi-cyclic heterocyclic ring" and the like.

As the "3-15 membered unsaturated mono-cyclic or multi-cyclic heterocyclic ring", there are mentioned, for example, an aromatic mono-cyclic heterocyclic ring, (e.g. pyrrole, imidazole, triazole, tetrazole, pyrazole, pyridine, pyrazine, pyrimidine, pyridazine, triazine, furan, thiophene, oxazole, isoxazole, thiazole, isothiazole, furazane, oxadiazole, thiadiazole ring and the like), an aromatic multi-cyclic heterocyclic ring (e.g. indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazane, benzothiadiazole, benzotriazole, carbazole, β-carboline, acridine, phenazine, dibenzofuran, dibenzothiophene, phenanthridine, phenanthroline, perimidine ring and the like), a non-aromatic unsaturated heterocyclic ring (e.g. azepine, diazepine, pyran, oxepin, thiopyran, thiepin, oxazine, oxadiazine, oxazepine, oxadiazepine, thiazine, thiadiazine, thiazepine, thiadiazepine, indolizine, dithianaphthalene, quinolidine, chromene, benzoxepin, benzoxazepine, benzoxadiazepine, benzothiepin, benzothiazepine, benzothiadiazepine, benzazepine, benzodiazepine, xanthene, phenothiazine, phenoxazine, phenoxathiin, thianthrene, pyrroline, imidazoline, 2,3-dihydro-1H-pyrazole, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrofuran, dihydropyran, dihydrooxepin, tetrahydrooxepin, dihydrothiophene, dihydrothiopyran, dihydrothiepin, tetrahydrothiepin, dihydrooxazole, dihydroisoxazole, dihydrothiazole, dihydroisothiazole, dihydrofurazane, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathian, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepan, dihydrobenzoxazepine, tetrahydrobenzoxazepine, dihydrocarbazole, tetrahydrocarbazole, dihydro-β-carboline, tetrahydro-β-carboline, dihydroacridine, tetrahydroacridine, dihydrodibenzofuran, dihydrodibenzothiophene, tetrahydrodibenzofuran, tetrahydrodibenzothiophene, dioxaindan, benzodioxane, chromane, benzodithiolan and benzodithian ring) and the like. And the "3-15 membered saturated mono-cyclic or multi-cyclic heterocyclic ring" includes, for example, aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepin, thiirane, thietane, tetrahydrothiophene, tetrahydrothiopyran, perhydrothiepine, tetrahydrooxazole (oxazolidine), tetrahydroisoxazole (isooxazolidine), tetrahydrothiazole (thiazolidine), tetrahydroisothiazole (isothiazolidine), tetrahydrofurazane, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydro-β-carboline, perhydroacridine, perhydrodibenzofuran, perhydrodibenzothiophene, dioxolane, dioxane, dithiolane, dithiane, the ring of the formula:

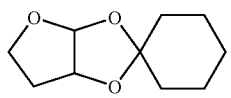

and the like.

The above-mentioned "hydrocarbon group" or "heterocyclic ring group" may have 1-5 of substituents selected from the groups mentioned under the following items (1)-(39), and when they have more than one substituent, such substituents may be the same or different. Examples of the "substituents" include (1) a hydrocarbon group which may have substituent(s) [e.g. a C1-8 aliphatic hydrocarbon group (the "hydrocarbon group" has the same meaning as described hereinbefore, e.g. methyl, ethyl, propyl, isopropyl, butyl, tert-butyl, vinyl, propenyland hexenyl and the like), amino, sulfo, halogen, carboxy, cyano, nitro, oxo, thioxo, hydroxy, methoxy, trifluoromethyl, trifluoromethoxy, allyloxy, benzyloxy and the like] (the "hydrocarbon group" has the same meaning as the "hydrocarbon group" described hereinbefore), (2) a heterocyclic ring which may have substituent(s) [e.g. a hydrocarbon group (the "hydrocarbon group" has the same meaning as the "hydrocarbon group" described hereinbefore) which may have substituent(s) (e.g. halogen, hydroxy, trifluoromethyl, trifluoromethoxy, acetyloxy and the like), amino, sulfo, halogen, carboxy, cyano, nitro, oxo, thioxo, hydroxy, methoxy, methoxycarbonyl, trifluoromethyl, trifluoromethoxy, acetyl and the like], (3) amino, (4) C1-6 acylamino (e.g. acetylamino, propionylamino and the like), (5) mono- or di-substituted amino substituted with a hydrocarbon group (e.g. methylamino, ethylamino, propylamino, isopropylamino, butylamino, dimethylamino, diethylamino, cyclohexylamino, 1-carbamoyl-2-cyclohexylethylamino, N-butyl-N-cyclohexylmethylamino, phenylamino and the like) (the "hydrocarbon group" has the same meaning as the "hydrocarbon group" described hereinbefore, and the group may be substituted with oxo, amino, carbamoyl and the like), (6) C1-4 alkylsulfonylamino (e.g. methylsulfonylamino, ethylsulfonylamino and the like), (7) phenylsulfonylamino, (8) C1-4 alkylsulfonyl (e.g. methylsulfonyl, ethylsulfonyl and the like), (9) phenylsulfonyl, (10) halogen (e.g. fluorine, chlorine, bromine, iodine), (11) carboxy, (12) cyano, (13) nitro, (14) oxo, (15) thioxo, (16) hydroxy, (17) C1-8 alkoxy which may have substituent(s) (e.g. mono- or di-substituted amino, carboxy, halogen and the like) (e.g. methoxy, ethoxy, propoxy, isopropoxy, butoxy, isobutoxy, sec-butoxy, tert-butoxy, hexyloxy, octyloxy, cyclohexylmethyloxy, benzyloxy, 2-propenyloxy, trifluoromethoxy, carboxymethoxy, dimethylaminopropoxy, diethylaminoethoxy and the like), (18) C3-8 cycloalkoxy (e.g. cyclohexyloxy and the like), (19) phenoxy which may have substituent(s) (e.g. halogen and the like), (20) mercapto, (21) C1-4 alkylthio (e.g. methylthio, ethylthio, propylthio, isopropylthio, butylthio, tert-butylthio and the like), (22) phenylthio (e.g. 4-chlorophenylthio and the like) which may have substituent(s) (e.g. halogen and the like), (23) carbamoyl, (24) aminocarbonyl which may be substituted with hydrocarbon group(s) (e.g. N-butylaminocarbonyl, N-cyclohexylmethylaminocarbonyl, N-butyl-N-cyclohexylmethylaminocarbonyl, N-cyclohexylaminocarbonyl, phenylaminocarbonyl and the like) (the "hydrocarbon group" has the same meaning as the "hydrocarbon group" described hereinbefore), (25) sulfamoyl, (26) aminosulfonyl substituted with hydrocarbon group(s) (e.g. methylaminosulfonyl and the like) (the "hydrocarbon group" has the same meaning as the "hydrocarbon group" described hereinbefore), (27) aminosulfonyl (e.g. dimethylaminoethylaminosulfonyl, dimethylaminopropyl-aminosulfonyl and the like) substituted with hydrocarbon group(s) which is/are substituted with amino (the "hydrocarbon group" has the same meaning as the "hydrocarbon group" described hereinbefore), (28) C1-6 alkoxycarbonyl (e.g. methoxycarbonyl, ethoxycarbonyl, tert-butoxycarbonyl and the like), (29) sulfo (—$SO_3H$), (30) sulfino, (31) phosphono, (32) amidino, (33) imino, (34) —$B(OH)_2$, (35) C1-4 alkylsulfinyl (e.g. methylsulfinyl, ethylsulfinyl and the like), (36) C1-6 acyl (e.g. formyl, acetyl, propionyl, butyryl and the like), (37) benzoyl, (38) hydroxyimino or (39) C1-4 alkyloxyimino (e.g. methyloxyimino, ethyloxyimino and the like), etc.

In the definitions of the terms "phenylsulfonyl which may have substituent(s)", "carbamoyl which may have substituent(s)", "sulfamoyl which may have substituent(s)" and "benzoyl which may have substituent(s)", which are described hereinbefore for defining a substituent on the ring A, the term "substituent" has the same meaning as the "substituent" appearing in the term "hydrocarbon group which may have substituent(s)" mentioned for the substituent on the ring A described hereinbefore.

Examples of the "nitrogen atom which may have a substituent" represented by X include =$NR^{101}$ wherein $R^{101}$ includes, for example, hydrogen, cyano, hydroxy, C1-4 alkoxy (e.g. methoxy, ethoxy, propoxy, butoxy and the like), a hydrocarbon group which may have substituent(s) (the "hydrocarbon group" has the same meaning as the "hydrocarbon group which may substituent(s)"), sulfo, C1-8 alkylsulfonyl (e.g. methylsulfonyl, ethylsulfonyl and the like), phenylsulfonyl and the like.

X is preferably oxygen.

The "hydrocarbon group which may have substituent(s)" represented by $R^1$, $R^2$, $R^3$, $R^4$ or $R^5$ has the same meaning as the "hydrocarbon group" mentioned as the substituent on the ring A described hereinbefore.

The "heterocyclic ring group which may have substituent(s)" represented by $R^1$, $R^2$, $R^3$ or $R^4$ has the same meaning as the "heterocyclic ring group which may have substituent(s)" mentioned as the substituent on the ring A described hereinbefore.

$R^1$ and $R^2$ as well as $R^3$ and $R^4$ each independently may be taken together with the adjacent nitrogen atom(s) to form an N-containing heterocyclic ring which may have substituent(s). The "N-containing heterocyclic ring" includes, for example, a mono-cyclic or multi-cyclic heterocyclic ring which may contain 1-6 of heteroatom(s) selected from nitrogen, oxygen and sulfur in addition to the above nitrogen atom.

Examples of the "N-containing heterocyclic ring" include a "3-15 membered N-containing unsaturated mono-cyclic or multi-cyclic heterocyclic ring", "3-15 membered N-containing saturated mono-cyclic or multi-cyclic heterocyclic ring" and the like.

As examples of the "3-15 membered N-containing unsaturated mono-cyclic or multi-cyclic heterocyclic ring", there are mentioned pyrrole, imidazole, triazole, tetrazole, pyrazole, azepine, diazepine, indole, isoindole, indazole, purine, benzimidazole, benzazepine, benzodiazepine, benzotriazole, carbazole, β-carboline, phenothiazine, phenoxazine, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazane, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, dihydroacridine, tetrahydroacridine, hexahydroazocine, hexahydroazonine, hexahydrodiazocine, hexahydrodiazonine, octahydroazecine, octahydrodiazecine ring and the like. Examples of the "3-15 membered N-containing saturated mono-cyclic or multi-cyclic heterocyclic ring" include aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, tetrahydrooxazole (oxazolidine), tetrahydroisoxazole (isooxazolidine), tetrahydrothiazole (thiazolidine), tetrahydroisothiazole (isothiazolidine), tetrahydrofurazane, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, tetrahydrothiazepine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine, perhydroazonine, perhydroazecine, azaundecane, azadodecane, azatridecane, azatetradecane, azapentadecane, perhydrodiazocine, perhydrodiazonine, perhydrodiazecine, diazaundecane, diazadodecane, diazatridecane, diazatetradecane, diazapentadecane, perhydroindole, perhydroisoindole, perhydro-β-carboline, perhydrophenazine, perhydrophenothiazine, perhydrophenoxazine, perhydrophenanthridine, perhydrophenanthroline, perhydroperimidine, azabicyclo[3.2.2]nonane, azabicyclo[3.3.2]decane, azabicyclo[2.2.2]octane, azabicyclo[3.3.3]undecane, azabicyclo[4.3.3]dodecane, azabicyclo[4.4.3]tridecane, azabicyclo[4.4.4]tetradecane, 1,4-dioxa-8-azaspiro[4.5]decane, etc. The said "N-containing heterocyclic ring" may be substituted with 1-5 of arbitrary substituents, and examples of the "substituents" include the same as the substituents on the ring A described hereinbefore.

The "substituent" represented by $R^{11}$ has the same meaning as the "substituent(s)" on the "carbocyclic group which may have substituent(s)" mentioned as the substituent of the above ring A.

$R^1$ is preferably a hydrocarbon group which may have substituent(s), and more preferably, C1-8 alkyl which may have substituent(s) or a benzene ring which may have substituent(s).

$R^2$ is preferably a hydrocarbon group which may have substituent(s) or a heterocyclic ring which may have substituent(s), etc., more preferably C1-8 alkyl which may have substituent(s) or a benzene ring which may have substituent(s), and most preferably methyl or ethyl.

And $R^1$ and $R^2$ may prefereably be taken together with the adjacent nitrogen atom to form an N-containing heterocyclic ring group, and the said N-containing heterocyclic ring group includes preferably, for example, piperidine, pyrrolidine, morpholine, piperazine, indoline, tetrahydroquinoline and tetrahydroisoquinoline rings, and more preferably, piperidine, piperazine or indoline ring.

$R^3$ is preferably hydrogen, a hydrocarbon group which may have substituent(s) or a heterocyclic ring group which may have substituent(s) and the like, and more preferably, a benzene ring which may have substituent(s) or a pyridine ring which may have substituent(s), and most preferably, a benzene ring which is substituted with 1-2 of trifluoromethyl or halogen.

$R^4$ is preferably hydrogen, a hydrocarbon group which may have substituent(s) or a heterocyclic ring group which may have substituent(s), and more preferably, hydrogen.

$R^5$ is preferably a benzene ring which may have substituent(s) or a methyl group, etc.

$R^{11}$ is preferably halogen or C1-8 alkyl which may have substituent(s), and more preferably, chlorine, trifluoromethyl, etc.

n is preferably 0 or an integer of 1 to 2, and more preferably 2.

Referring specifically to the compound of the present invention of the formula (I), preferred are the compounds represented by
the formula (I-1):

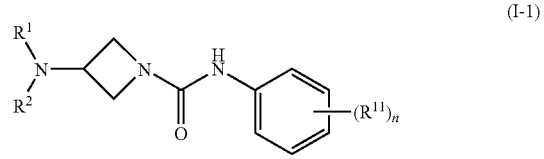

(I-1)

wherein all the symbols have the same meanings as described hereinbefore;

the formula (I-2):

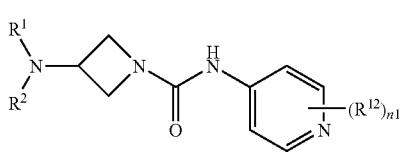

(I-2)

wherein $R^{12}$ has the same meaning as $R^{11}$, n1 is 0 or an integer of 1-4, and when n1 is 2 or more, the plural $R^{12}$s may be the same or different, while other symbols have the same meanings as described hereinbefore;

the formula (I-3):

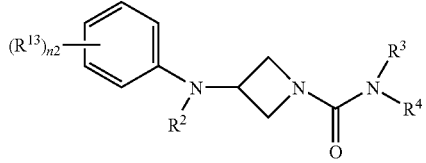

(I-3)

wherein $R^{13}$ has the same meaning as $R^{11}$, n2 is 0 or an integer of 1-5, and when n2 is 2 or more, the plural $R^{13}$s may be the same or different, while other symbols have the same meanings as described hereinbefore;

the formula (I-4):

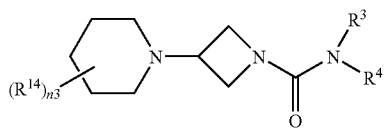

(I-4)

wherein $R^{14}$ has the same meaning as $R^{11}$, n3 is 0 or an integer of 1-5, and when n3 is 2 or more, the plural $R^{14}$s may be the same or different, while other symbols have the same meanings as described hereinbefore;

the formula (I-5):

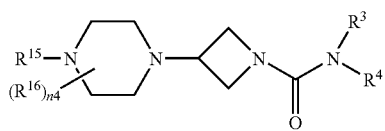

(I-5)

wherein $R^{15}$ and $R^{16}$ have each independently the same meanings as $R^{11}$, n4 is 0 or an integer of 1-4, and when n4 is 2 or more, the plural $R^{16}$s may be the same or different, while other symbols have the same meanings as described hereinbefore;

the formula (I-6):

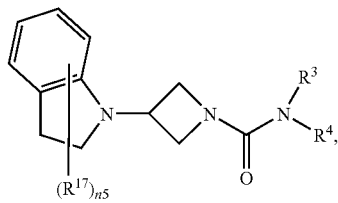

(I-6)

wherein $R^{17}$ has the same meaning as $R^{11}$, n5 is 0 or an integer of 1-6, and when n5 is 2 or more, the plural $R^{17}$s may be the same or different, while the other symbols have the same meanings as described hereinbefore; and the formula (I-7):

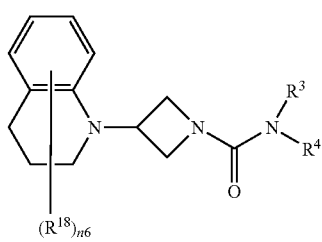

(I-7)

wherein $R^{18}$ has the same meaning as $R^{11}$, n6 is 0 or an integer of 1-7, and when n6 is 2 or more, the plural $R^{18}$s may be the same or different, while the other symbols have the same meanings as described hereinbefore, a salt thereof, an N-oxide thereof, a solvate thereof, a prodrug thereof and the like. In particular, more preferred are the compounds represented by the formula (I-1-1):

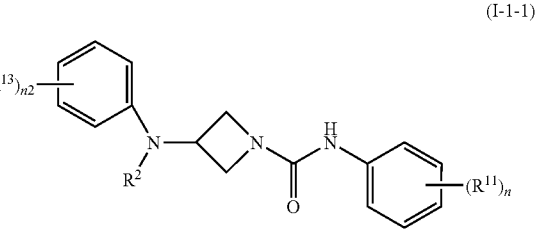

(I-1-1)

wherein all the symbols have the same meanings as described hereinbefore;

the formula (I-1-2):

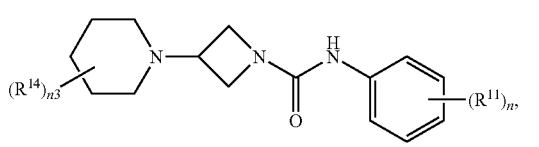

(I-1-2)

wherein all the symbols have the same meanings as described hereinbefore; and the formula (I-1-3):

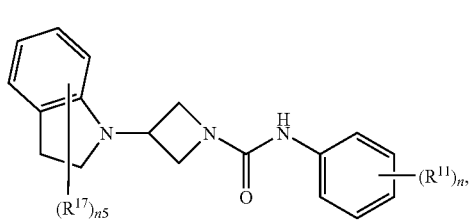

(I-1-3)

wherein all the symbols have the same meanings as described hereinbefore, a salt thereof, an N-oxide, a solvate thereof or a prodrug thereof and the like.

The specific examples of the compound according to the present invention include N-[3,5-bis(trifluoromethyl)phenyl]-3-[isobutyl(3-methoxyphenyl)amino]-N,2,2-trimethylazetidine-1-carboxamide, methyl 4-[[2-(hydroxymethyl)-1-({[3-(2-methylphenoxy)phenyl]amino}carbonothioyl)azetidin-3-yl](2-phenoxyethyl)amino]-benzoate, N-[1-[[butyl(3,4-difluorophenyl)amino](imino)methyl]-3-(4-chlorophenyl)-azetidin-3-yl]-N-[4-(methylsulfonyl)phenyl]-β-alanine, 3-[(2-chlorophenyl)-(phenylsulfonyl)amino]-1-[[(2-cyano-4-nitrophenyl)amino](methoxyimino)methyl]-azetidin-2-carboxylic acid, N-{1-[(benzylimino)(morpholine-4-yl)methyl]-3-fluoroazetidin-3-yl}-N-[3-(trifluoromethyl)phenyl]ethanesulfonamide, 3-methyl-N-(1-{[4-(methylsulfonyl)piperazin-1-yl]carbonyl}-2-pyridin-2-ylazetidin-3-yl)-N-phenylbutanamide, N-benzyl-3-{[(benzylamino)carbonyl]amino}-N-(2,6-dichloropyridin-4-yl)-3-(3,6-dihydro-2H-pyran-4-yl)azetidine-1-carboxamide, isopropyl {1-[(cyanoimino)(4-methylpiperazin-1-yl)methyl]azetidin-3-yl}(2-cyanophenyl)carbamate, N,N-dimethyl-N'-(3-nitrophenyl)-N'-[1-(2,3,4,7-tetrahydro-1H-azepin-1-ylcarbonyl)-azetidin-3-yl]sulfamide, (4-{[[1-(2,3-dihydro-1H-indol-1-ylcarbonyl)azetidin-3-yl](morpholin-4-ylcarbonyl)amino]methyl}phenyl)boronic acid, 3-[{{2-isobutyl-3-[(4-methyl-1,3-thiazol-2-yl)(2-morpholin-4-ylethyl)amino]azetidin-1-yl}[(phenyl-sulfonyl)-imino]methyl}(tetrahydro-2H-pyran-4-ylmethyl)amino]benzoic acid, N-[3-(cyclopentylmethyl)-1-(pyrrolidin-1-ylcarbonyl)azetidin-3-yl]-N',N'-dimethyl-N-(1-phenylazepan-2-yl)propan-1,3-diamine, methyl 4-[(3-{benzyl[3-(methylamino)-3-oxopropyl]amino}azetidin-1-yl)carbonyl]piperazin-1-carboxylate, 2-[(3-biphenyl-3-yl-1-{[4-(3-chlorobenzoyl)piperazin-1-yl]carbonyl}azetidin-3-yl)(cyclohexyl)-amino]ethanol, 3-[[1-[(6-methoxy-3,4-dihydroisoquinolin-2(1H)-yl)carbonyl]-2-(3-thienyl)azetidin-3-yl](1-naphthyl)amino]propanenitrile, {1-({[2-(1-naphthyl)ethyl]-amino}carbonyl)-3-[(2-phenylethyl)(4-pyridin-2-ylphenyl)amino]azetidin-3-yl}-phosphonic acid, 2-[amino(imino)methyl]-3-[1H-indol-5-yl(phenyl)amino]-N-(tetrahydro-2H-pyran-4-yl)azetidine-1-carboxamide, N-[2-chloro-6-(pentyloxy)-pyridin-4-yl]-3-[isopropyl(pyridin-2-yl)amino]azetidine-1-carboxamide, N-(3,5-difluorophenyl)-3-(2,6-dimethylmorpholin-4-yl)azetidine-1-carboxamide, 3-(3,5-dimethylthiomorpholin-4-yl)-N-(4-methyl-1,3-thiazole-2-yl)azetidine-1-carboxamide, N-(6-methylpyrazin-2-yl)-3-{2-[3-(methylthio)phenyl]-1,3-thiazolidin-3-yl}-azetidine-1-carboxamide, $N^{3'},N^{3'}$-diethyl-$N^{1'}$-[3-fluoro-5-(trifluoromethyl)phenyl]-3-hydroxy-1,3'-biazetidin-1',3'-dicarboxamide, N-[2-(cyclohexyloxy)pyrimidin-4-yl]-3-(3,4-dihydro-1,6-naphthyridine-1(2H)-yl)azetidine-1-carboxamide, N-(3-butoxy-5-chlorophenyl)-3-[(1,3-dimethyl-1H-pyrazole-5-yl)(propyl)amino]azetidine-1-carboxamide, 3-[(5-cyanopyridin-2-yl)(cyclopropyl)amino]-N-[3-(tetrahydro-2H-pyran-4-yloxy)-5-(trifluoromethyl)phenyl]azetidine-1-carboxamide, 3-(5-acetyl-2,3-dihydro-1H-indol-1-yl)-N-[3-chloro-5-(methylthio)phenyl]azetidine-1-carboxamide, methyl 2-[(1-{[(6-chloropyridazine-4-yl)amino]carbonyl}azetidin-3-yl)(isobutyl)-amino]-1-methyl-1H-imidazole-4-carboxylate, 3-[(5-chloro-2-methoxypyrimidin-4-yl)(isopropyl)amino]-N'-cyano-N-(3,5-dimethylphenyl)azetidine-1-carboximidamide, 3-{cyclopentyl[3-(trifluoromethyl)phenyl]amino}-N-[6-(phenylthio)pyridin-2-yl]-azetidine-1-carboxamide, or N-(3-chloro-5-fluorophenyl)-3-cyano-3-(5-fluoro-3,3-dimethyl-2,3-dihydro-1H-indol-1-yl)azetidine-1-carboxamide and the like.

Those compounds described in the below-mentioned Examples are all preferred.

As the more preferable compounds, there are mentioned, for example, N-(3,5-dichlorophenyl)-3-(4-phenylpiperidin-1-yl)azetidine-1-carboxamide, 3-(2,3-dihydro-1H-indol-1-yl)-N-[3-(trifluoromethyl)phenyl]azetidine-1-carboxamide, N-(3,5-dichlorophenyl)-3-(2,3-dihydro-1H-indol-1-yl)azetidine-1-carboxamide, N-[3,5-bis(trifluoromethyl)phenyl]-3-(2,3-dihydro-1H-indol-1-yl)azetidine-1-carboxamide, 3-(2,3-dihydro-1H-indol-1-yl)-N-(3-phenoxyphenyl)azetidine-1-carboxamide, N-[3,5-bis(trifluoromethyl)phenyl]-3-[methyl(phenyl)amino]azetidine-1-carboxamide and N-[3,5-bis(trifluoromethyl)phenyl]-3-[ethyl(phenyl)amino]azetidine-1-carboxamide, and the like.

In the present invention, as may be easily understood by those skilled in the art and unless otherwise specified particularly, the symbol: ⋯⋯ is understood to indicate that the substituent is linked in such an orientation as may go into the sheet of paper (α-configuration);

the symbol: ◢ is understood to indicate that the substituent is linked in such an orientation as may come out of the sheet of paper (β-configuration);

the symbol: ⁓ is understood to indicate that the substituent is linked either in the α-configuration, β-configuration or any combined configurations thereof at arbitrary ratios; and the symbol: ╱ is understood to indicate that the substituent is linked in any combined configurations of the α-configuration and β-configuration at arbitrary ratios.

The present invention is understood to encompass and include all of the isomers, unless otherwise specified particularly. Whenever reference is made to alkyl, alkenyl, alkynyl, alkoxy, alkylthio, alkylene, alkenylene and alkynylene, for example, such terms should be understood to include both of the straight-chain and branched ones. Moreover, the present invention is intended to encompass any isomers existing with respect to the presence of a double bond, ring or fused ring (namely, E, Z, and cis- and trans-isomers), any isomers existing with respect to the presence of the asymmetric carbon atom, etc. (namely, R-and S-isomers, α- and β-configurations, enantiomers and diastereomers), any optically active compounds having optical rotation (namely, D-, L-, d-, and l-isomers), any polar compounds by chromatographic separation (namely, highly polar or weakly polar), any equilibrium compounds, any rotational isomers, and any mixtures thereof in arbitrary ratios and racemic mixtures thereof.

[Salts]

The salts of the compound of the formula (I) include non-toxic salts, pharmacologically acceptable salts and any other salts. Such pharmacologically acceptable salts are preferably non-toxic and water-soluble ones. Appropriate salts of the compound of the formula (I) include, for example, salts with alkali metals (e.g. potassium, sodium and lithium salts), salts with alkaline-earth metals (e.g. calcium, magnesium and the like), ammonium salts (e.g. tetramethylammonium salt, tetrabutyl-ammonium salt and the like), organic-amine salts (e.g. salts with triethylamine, methylamine, dimethylamine, cyclopentylamine, benzylamine, phenethylamine, piperidine, monoethanolamine, diethanolamine, tris(hydroxymethyl)methylamine, lysine, arguinine, N-methyl-D-glucamine and the like), or acid-addition salts [inorganic acid salts (e.g. hydrochloride, hydrobromate, hydroiodate, sulfate, phosphate, nitrate and the like), organic acid salts (e.g. acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate and the like) and the like]. The salts of the compound of the present invention include solvates, or solvates of the above-mentioned alkali metal salts, alkaline-earth metal salts, ammonium salts, organic-amine salts or acid-addition salts and the like. The solvates are preferably non-toxic and water-soluble ones. Appropriate solvates include, for example, solvates with water or alcoholic solvents (e.g. ethanol and the like). The compound of the present invention may be converted to non-toxic salts or pharmacologically acceptable salts by the known methods.

And the salts include quaternary ammonium salts. The quaternary ammonium salts refer to any compounds of the formula (I) wherein the nitrogen atom is quaternized by $R^0$ group (wherein $R^0$ is C1-8 alkyl or C1-8 alkyl substituted with a phenyl group).

The compound of the present invention may be converted to an N-oxide by arbitrary methods. An N-oxide means a compound whose nitrogen atom is oxidized in the compound of the formula (I).

The prodrugs of the compound of the formula (I) refer to the compounds being convertible in vivo into the compound of the formula (I) by the reactions with the enzymes, gastric acid and the like. As the prodrugs of the compound of the formula (I), for example, there are mentioned the compounds of the formula (I) wherein when the compound of the formula (I) has an amino group, such amino group is acylated, alkylated or phosphorylated (e.g. the compounds having the amino group of the compound of the formula (I) which are eicosanoylated, alanylated, pentylaminocarbonylated, (5-methyl-2-oxo-1,3-dioxolene-4-yl)methoxycarbonylated, tetrahydrofuranylated,. pyrrolidylmethylated, pivaloyloxymethylated, acetoxymethylated or tert-butylated); the compounds of the formula (I) wherein when the compound of the formula (I) has a hydroxy group, such hydroxy group is acylated, alkylated, phosphorylated or borated (e.g. the compounds having the hydroxy group of the compound of the formula (I) which are acetylated, palmitoylated, propanoylated, pivaloylated, succinylated, fumarylated, alanylated, dimethylaminomethyl or carbonylated); the compounds of the formula (I) wherein when the compound of the formula (I) has an carboxyl group, such carboxyl group is esterified or amidated (e.g. the compounds having the carboxyl group of the compound of the formula (I) which are ethylesterified, phenylesterified, carboxymethylesterified, dimethylaminomethyl-esterified, pivaloyloxymethylesterified, ethoxycarbonyloxyethylesterified, phthalidylesterified, (5-methyl-2-oxo-1,3-dioxolene-4-yl)methylesterified, cyclohexyloxycarbonylethylesterified or methylamidated); and the like. These compounds can be manufactured by the conventional methods. In addition, the prodrugs of the compounds of the formula (I) may be either of solvates and non-solvates. The prodrugs of the compound of the formula (I) may be the ones which are converted to the compound of the formula (I) under physiological conditions as described in Development of Pharmaceutical Products, Vol. 7 "Molecular Design", 163-198, 1990, published by Hirokawa Shoten of Japan. And the compound of the formula (I) may be labeled with isotopes (e.g. $^3$H, $^{14}$C, $^{35}$S, $^{125}$I and the like), etc.

[The Method for Preparation of the Compound of the Present Invention]

The compound of the formula (I) of the present invention may be prepared by the below-described processes, the processes as delineated in Examples or the known processes, such as the processes described in Comprehensive Organic Transformations: A Guide to Functional Group Preparations, 2nd Edition (Richard C. Larock, John Wiley & Sons Inc, 1999), after being suitably modified and combined. It is to be added that the starting compound may be used as a salt in each of the below-mentioned production processes, wherein use can be made of salts mentioned in the above as the salts of the formula (I).

The compounds of the formula (I) wherein X is oxygen or sulfur and $R^4$ is hydrogen may be prepared by the below-described two processes:

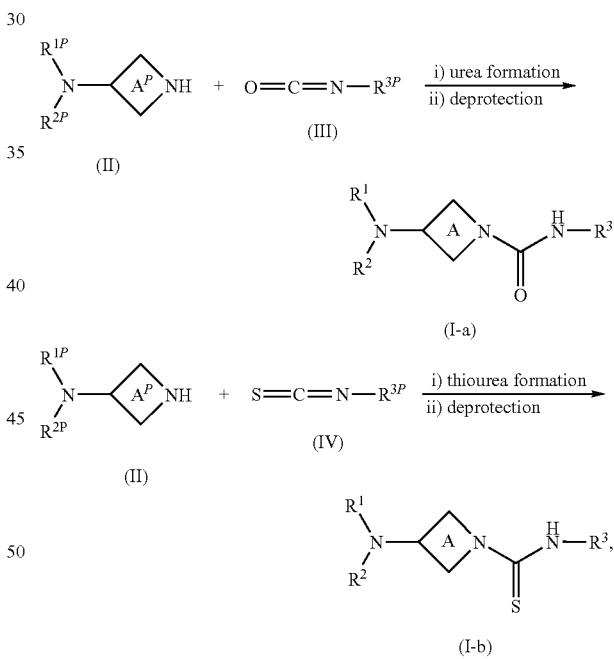

wherein the rings $A^P$, $R^{1P}$, $R^{2P}$ and $R^{3P}$ have each the same meanings as the rings A, $R^1$, $R^2$ and $R^3$ respectively, with the proviso that the carboxy, hydroxy, amino and mercapto groups included in the group represented by A, $R^1$, $R^2$ or $R^3$ are protected if necessary, and other symbols have the same meanings as described hereinbefore.

These urea- and thiourea-formation reactions are known and, for example, can be carried out in an organic solvent (e.g. toluene, benzene, xylene, tetrahydrofuran, dichloromethane, diethyl ether, 1,2-dichloroethane, N,N-dimethylformamide and the like), in the presence or absence of a base (e.g.

triethylamine, pyridine, diisopropylethyl-amine and the like), at a temperature of about 0° C. to the the refluxing temperature.

These reactions may preferably be carried out under the atmosphere of an inert gas and under anhydrous conditions.

The deprotection reaction of protective groups is conducted according to the known procedures, for example, those described in Protective Groups in Organic Synthesis (T. W. Greene, Wiley, New York, 1999) or those similar thereto. For example, the deprotection reaction of a protective group for carboxy, hydroxy, amino or mercapto is well known, and as the deprotection reaction, for example, there are mentioned (1) a deprotection reaction by alkaline hydrolysis, (2) a deprotection reaction under acidic conditions, (3) a deprotection reaction by hydrogenolysis, (4) a deprotection reaction by use of a silyl group, (5) a deprotection reaction using metals, (6) a deprotection reaction using metal complexes, and the like.

These procedures are to be explained more particularly in the following:

(1) The deprotection reaction by alkaline hydrolysis is carried out, for example, in an organic solvent (e.g. methanol, tetrahydrofuran, or dioxane and the like) using an alkali metal hydroxide (e.g. sodium hydroxide, potassium hydroxide, or lithium hydroxide and the like), an alkaline-earth metal hydroxide (e.g. barium hydroxide, or calcium hydroxide and the like), their carbonate (e.g. sodium carbonate or potassium carbonate and the like), an aqueous solution thereof, or a mixture thereof at a temperature of about 0 to 40° C.

(2) The deprotection reaction under acidic conditions is carried out, for example, in an organic solvent (e.g. dichloromethane, chloroform, 1,4-dioxane, ethyl acetate, anisole and the like) in the presence of an organic acid (e.g. acetic acid, trifluoroacetic acid, methanesulfonic acid, p-toluenesulfonic acid and the like), an inorganic acid (e.g. hydrochloric acid, sulfuric acid and the like) or a mixture thereof (e.g. hydrogen bromide/acetic acid and the like) at a temperature of about 0 to 100° C.

(3) The deprotection reaction by hydrogenolysis is carried out, for example, in. a solvent (e.g. ethers (e.g. tetrahydrofuran, 1,4-dioxane, dimethoxyethane, diethyl ether and the like), alcohols (e.g. methanol, ethanol and the like), benzenes (e.g. benzene, toluene and the like), ketones (e.g. acetone, methyl ethyl ketone and the like), nitriles (e.g. actetonitrile and the like), amides (e.g. dimethylformamide and the like), water, ethyl acetate, acetic acid, or solvent mixtures of at least two thereof and the like) in the presence of a catalyst (e.g. palladium-carbon, palladium black, palladium hydroxide, platinum oxide, Raney nickel and the like) under the atmosphere of hydrogen at atmospheric or suitably applied pressure or in the presence of ammonium formate at a temperature of about 0 to 200° C.

(4) The deprotection reaction for a silyl group is carried out, for example, in a water-miscible organic solvent (e.g. tetrahydrofuran, acetonitrile and the like) using a fluoride (e.g. tetrabutylammonium fluoride, potassium fluoride, hydrogen fluoride and the like) at a temperature of about 0 to 40° C.

(5) The deprotection reaction using metals is carried out, for example, in an acidic solvent (e.g. acetic acid, buffer solution at a pH value of about 4.2-7.2, or a mixture of such solutions with an organic solvent, e.g. tetrahydrofuran, and the like) in the presence of zinc powder, with sonication if necessary, at a temperature of about 0 to 40° C.

(6) The deprotection reaction using metal complexes is carried out, for example, in an organic solvent (e.g. dichloromethane, N,N-dimethylformamide, tetrahydrofuran, ethyl acetate, acetonitrile, 1,4-dioxane, ethanol and the like), water, or mixtures thereof, in the presence of a trap reagent (e.g. tributyltin hydride, triethylsilane, dimedone, morpholine, diethylamine, pyrrolidine and the like), an organic acid (e.g. acetic acid, formic acid, 2-ethylhexanoic acid and the like) and/or organic acid salts (e.g. sodium 2-ethylhexanoate, potassium 2-ethylhexanoate and the like), in the presence or absence of a phosphine reagent (e.g. triphenylphosphine and the like), using metal complexes [e.g. tetrakistriphenylphosphinepalladium(0), dichlorobis(triphenylphosphine)palladium(II), palladium acetate(II), tris(triphenylphosphine) rhodium(II) chloride and the like] at a temperature of about 0 to 40° C.

As may easily be understood by those skilled in the art, properly selected use can be made of these deprotection reactions to produce easily the objective compounds of the present invention.

The protective groups for carboxy include, for example, methyl, ethyl, allyl, tert-butyl, trichloroethyl, benzyl (Bn), phenacyl and the like, while the protective groups for hydroxy may be exemplified by methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), or 2,2,2-trichloroethoxycarbonyl (Troc) and the like. As the protective groups for amino, there is mentioned, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenyl-methoxycarbonyl, benzyl (Bn), p-methoxybenzyl, benzyloxymethyl (BOM), or 2-(trimethylsilyl)-ethoxymethyl (SEM). The protective groups for mercapto include, for example, benzyl, methoxybenzyl, methoxymethyl (MOM), 2-tetrahydropyranyl (THP), diphenylmethyl, or acetyl (Ac). The protective groups for carboxy, hydroxy, amino or mercapto are not limited particularly to the above-mentioned ones, only if they can be easily and selectively eliminated. For example, those described in Protective Groups in Organic Synthesis, (T. W. Greene, Wiley, New York, 1999) are usable.

The compound of the formula (I) wherein X is oxygen and $R^4$ is any atoms or groups other than hydrogen, i.e. the compound of the formula (I-c):

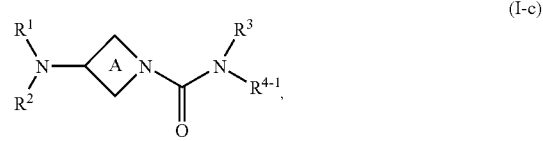

wherein $R^{4-1}$ is a hydrocarbon group which may have substituent(s), $-SO_2R^5$ or a heterocyclic ring group which may have substituent(s) and the other symbols have the same meanings as described hereinbefore, may be prepared by subjecting the compound of the formula (I-a) and the compound of the formula (V):

wherein $R^{4-1P}$ has the same meaning as $R^{4-1}$ and T is a leaving group (e.g. halogen, p-toluenesulfonyloxy, methanesulfonyloxy, trifluoromethanesulfonyloxy and the like), with the proviso that the carboxy, hydroxy, amino and mercapto groups contained in the group represented by $R^{4-1}$ are protected if necessary, to a reaction, optionally followed by a deprotection reaction.

The reaction is known and can be carried out, for example, in an organic solvent (e.g. tetrahydrofuran, N,N-dimethylformamide, 1,4-dioxane and the like) in the presence or absence of a phosphine reagent [e.g. triphenylphosphine, tri(o-tolyl) phosphine, tri-tert-butylphosphine, di-tert-butylphosphino-2-biphenyl and the like] and in the presence or absence of a metal complex [e.g. tetrakistriphenylphosphine palladium (0), dichlorobis(triphenyl-phosphine)palladium (II), palladium acetate (II), chlorotris(triphenylphosphine)rhodium (I) and the like] at a temperature of about 0° C. to the refluxing temperature, using a base (e.g. sodium hydride, potassium hydride, sodium hydroxide, potassium hydroxide, potassium carbonate, sodium carbonate, cesium carbonate, potassium phosphate, potassium tert-butoxide, sodium tert-butoxide and the like).

The deprotection reaction may be carried out by the same method as described hereinbefore.

And the compound of the formula (I-c) may be prepared by subjecting the compound of the formula (VI)

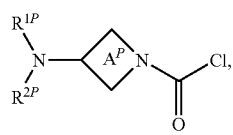

(VI)

wherein all the symbols have the same meanings as described hereinbefore, which is prepared by reacting the compound of the formula (II) with phosgene or triphosgene in the presence of a base (e.g. pyridine, triethylamine, diisopropylethylamine, potassium carbonate, sodium bicarbonate and the like), and the compound of the formula (VII):

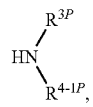

(VII)

wherein all the symbols have the same meanings as described hereinbefore, to a reaction, optionally followed by a deprotection reaction.

The compound of the formula (I-c) may be prepared by subjecting the compound of the formula (VI):

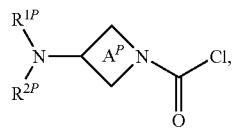

(VI)

wherein all the symbols have the same meanings as described hereinbefore, which is prepared by reacting the compound of the formula (II) with phosgene or triphosgene in the presence of a base (e.g. pyridine, triethylamine, diisopropylethylamine, potassium carbonate, sodium bicarbonate and the like), and the compound of the formula (VII):

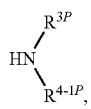

(VII)

wherein all the symbols have the same meanings as described hereinbefore, to a reaction, optionally followed by a deprotection reaction.

This reaction is known and is carried out, for example, in an organic solvent (e.g. dichloromethane, tetrahydrofuran, N,N-dimethylformamide and the like) in the presence of a base (e.g. pyridine, triethylamine, diisopropylethylamine, potassium carbonate, sodium bicarbonate and the like) at a temperature of about −78° C. to the refluxing temperature.

The compound of the formula (I) wherein $R^4$ is hydrogen and X is nitrogen which may be substituted, i.e. the compound of the formula (I-d):

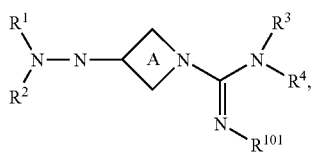

(I-d)

wherein all symbols have the same meanings as described hereinbefore, is prepared by subjecting the isothiourea compound, which is given by reacting the compound of the formula (I-b) with a halogenated alkyl (e.g. methyl iodide and the like), and the compound of the formula (VIII)

$$H_2N-R^{101P}$$ (VIII), wherein $R^{101P}$ has the same meaning as $R^{101}$, with the proviso that the carboxy, hydroxy, amino or mercapto group contained in the group represented by $R^{101}$ is protected if necessary, to a reaction, optionally followed by a deprotection reaction.

This reaction is known and is carried out, for example, in an organic solvent (e.g. methanol, ethanol, isopropanol, N,N-dimethylformamide and the like) at a temperature ranging from room temperature to the refluxing temperature, using a base (e.g. triethylamine and the like).

The deprotection reaction is carried out by the same method as described hereinbefore.

The compound of the formula (I) in which $R^1$ and $R^2$ are taken together with the adjacent nitrogen atom to form a piperazine ring, i.e. the compound of the formula (I-e):

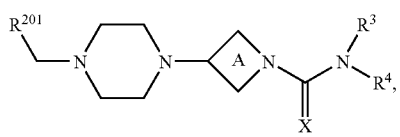

(I-e)

wherein $R^{201}$ is a hydrocarbon group which may have substituent(s) or arbitrary substituents and the other symbols have the same meanings as described hereinbefore, may be prepared by subjecting the compound of the formula (I-f):

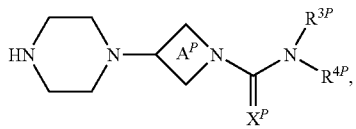
(I-f)

wherein $X^P$ has the same meaning as X, with the proviso that the carboxy, hydroxy, amino or mercapto in X is protected if necessary and the other symbols have the same meanings as described hereinbefore, which is prepared by the method described hereinbefore and the compound of the formula (IX):

$$R^{201P}\text{—CHO} \qquad (IX),$$

wherein $R^{201P}$ has the same meaning as $R^{201}$, with the proviso that the carboxy, hydroxy, amino or mercapto in $R^{201}$ is protected if necessary, to a reductive amination reaction, optionally followed by a deprotection reaction.

This reductive amination reaction is known and is carried out, for example, in an organic solvent (e.g. dichloroethane, dichloromethane, N,N-dimethylformamide and the like) in the presence of a reducing agent (e.g. sodium triacetoxyborohydride, sodium cyanoborohydride and the like) at a temperature of about 0 to 40° C., with or without use of a tertiary amine (e.g. triethylamine, diisopropylethylamine and the like) and/or an acid (e.g. acetic acid and the like).

The deprotection reaction may be carried out by the same method as described hereinbefore.

The compound of the formula (I) wherein. $R^1$ is a hydrocarbon group which may be substituted, i.e. the compound of the formula (I-g):

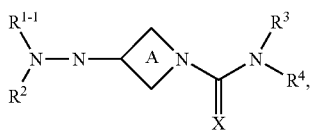
(I-g)

wherein $R^{1-1}$ is a hydrocarbon group which may be substituted, and the other symbols have the same meanings as described hereinbefore, may be prepared by subjecting the compound of the formula (I-h):

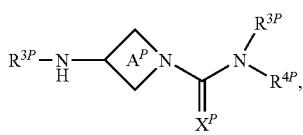
(I-h)

wherein all the symbols have the same meanings as described hereinbefore, which is prepared by the method described hereinbefore, and the compound of the formula (X):

$$R^{1-1P}\text{-T} \qquad (X),$$

wherein $R^{1-1P}$ has the same meaning as $R^{1-1}$, with the proviso that the carboxy, hydroxy, amino or mercapto in $R^{1-1}$ is protected if necessary, and the other symbols have the same meanings as described hereinbefore, to an alkylation reaction, optionally followed by a deprotection reaction.

This alkylation reaction is known and is carried out, for example, in an organic solvent (e.g. N,N-dimethylformamide, dimethylsulfoxide, chloroform, dichloromethane, diethyl ether, tetrahydrofuran and the like) in the presence or absence of a base (e.g. triethylamine, diisopropylamine, cesium carbonate, sodium carbonate, potassium carbonate and the like) at a temperature of about 0 to 40° C., using halogenated (C1-6)alkyl or halogenated benzyl.

The deprotection reaction for the protective groups may be carried out by the same method as described hereinbefore.

The compound of the formula (I) wherein $R^1$ is —$SO_2R^5$, i.e. the compound of the formula (I-i):

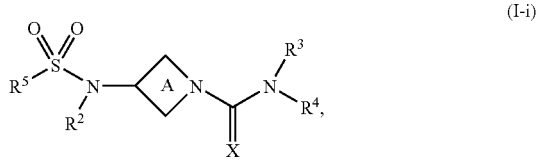
(I-i)

wherein all the symbols have the same meanings as described hereinbefore, may be prepared by subjecting the compound of the formula (I-h) as described hereinbefore and the compound of the formula (XI):

(XI)

wherein $R^{5P}$ has the same meaning as $R^5$, with the proviso that the carboxy, hydroxy, amino or mercapto group contained in the group represented by $R^5$ is protected if necessary, to a sulfonamidation reaction, optionally followed by a deprotection reaction.

This sulfonamidation reaction is known and is carried out, for example, by reacting a sulfonic acid with an acid halide (e.g. oxalyl chloride, thionyl chloride, phosphorous pentachloride, phosphorous trichloride and the like) in an organic solvent (e.g. chloroform, dichloromethane, dichloroethane, diethyl ether, tetrahydrofuran, tert-butyl methyl ether and the like) or without a solvent at a temperature of about −20° C. to the refluxing temperature, and the resultant sulfonyl halide is subjected to a reaction with an amine in an organic solvent (e.g. chloroform, dichloromethane, dichloroethane, diethyl ether, tetrahydrofuran and the like) in the presence of a base [e.g. diisopropylethylamine, pyridine, triethylamine, N,N-dimethylaniline, 4-(dimethylamino)pyridine and the like] at a temperature of about 0 to 40° C.

The deprotection reaction of the protective groups may be carried out as described hereinbefore.

The compound of the formula (I) wherein $R^1$ is the compound of the formula (I-j):

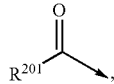

wherein $R^{201}$ has the same meaning as described hereinbefore, i.e. the compound of the formula (I-j):

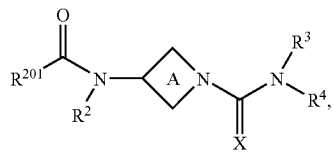

(I-j)

wherein all the symbols have the same meanings as described hereinbefore, may be prepared by subjecting the above-mentioned compound of the formula (I-h) and the compound of the formula (XII):

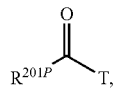

(XII)

wherein $R^{201P}$ has the same meaning as $R^{201}$, with the proviso that the carboxy, hydroxy, amino or mercapto group in the group represented by $R^{201}$ is protected if necessary and the other symbols have the same meanings as described hereinbefore, to an acylation reaction, optionally followed by a deprotection reaction.

This acylation reaction is known and is carried out, for example, in an organic solvent (e.g. dichloromethane, dichloroethane, tetrahydrofuran, N,N-dimethylformamide and the like) in the presence of a base (e.g. pyridine, triethylamine, diisopropylethylamine and the like) at a temperature of about −78° C. to the refluxing temperature.

The deprotection reaction of the protective groups may be carried out by the same procedure as described hereinbefore.

The compound of the formula (I) wherein $R^1$ is the compound of the formula:

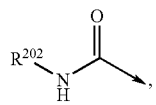

wherein $R^{202}$ is hydrogen or a hydrocarbon group which may have substituent(s), i.e. the compound of the formula (I-k):

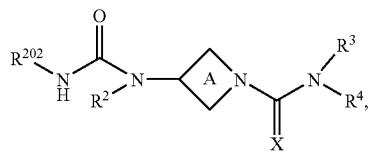

(I-k)

wherein all the symbols have the same meanings as described hereinbefore, may be prepared by subjecting the above-mentioned compound of the formula (I-h) and the compound of the formula (XIII):

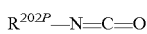

(XIII), wherein $R^{202P}$ has the same meaning as $R^{202}$, with the proviso that the carboxy, hydroxy, amino or mercapto group contained in the group represented by $R^{202}$ is protected if necessary and the other symbols have the same meanings as described hereinbefore, to a urea-formation reaction, optionally followed by a deprotection reaction.

This urea-formation reaction and the deprotection reaction for the protective group may be carried out by the method as described hereinbefore.

The compounds of the formulae (II) to (XIII) which are used as starting materials or reagents may be known per se or may be prepared easily by suitably modifying or combining the known methods, e.g. the methods as described in Comprehensive Organic Transformations : A Guide to Functional Group Preparations, 2nd Edition (Richard C. Larock, John Wiley & Sons Inc, 1999) or in the specification of U.S. Pat. No. 5,968,923.

For example, the compound of the formula (II) may be prepared by the following reaction scheme:

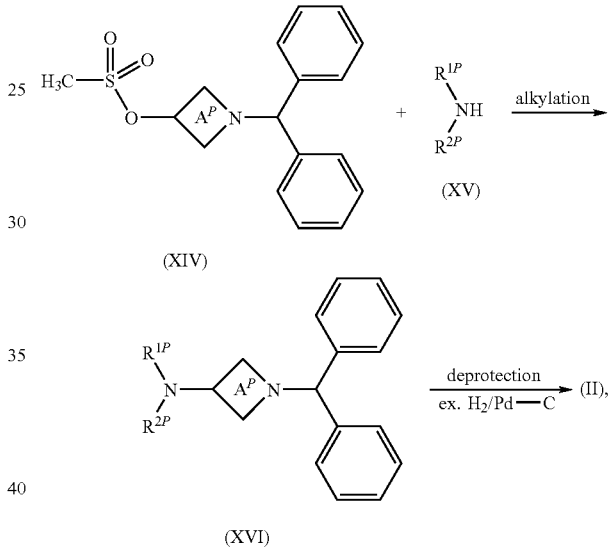

In the reaction steps, all the symbols have the same meanings as described hereinbefore.

In each of the reactions described in the present specification, the heating-involving reaction can be conducted using a water bath, an oil bath, a sand bath or microwave radiation, as is evident to those skilled in the art.

In each of the reactions described in the present specification, solid-phase supported reagents on high molecular polymers (e.g. polystyrene, polyacrylamide, polypropylene, polyethyleneglycol and the like) may be appropriately used.

In each of the reactions described in the present specification, the reaction products may be purified by the ordinarily employed purification techniques, e.g. atmospheric or vacuum distillation, high performance liquid chromatography on silica gel or magnesium silicate, thin layer chromatography, ion exchange resin, scavenger resin or column chromatography, washing, recrystallization and the like. Purification may be carried out at each reaction or after completion of several reactions.

[Toxicity]

The compound of the formula (I), a salt thereof, an N-oxide thereof, a solvate thereof or a prodrug thereof (hereafter from time to time referred to briefly as Compound of the Present Invention) exhibits extremely lowered toxicity, and is therefore safe enough to allow the use as pharmaceuticals.

[Application to Pharmaceuticals]

The Compound of the Present Invention exerts an antagonistic effect against EDG-5, and is useful for the prevention and/or treatment of the EDG-5-mediated diseases, for example, the diseases caused by blood vessel contraction (e.g. cerebrovascular spasmodic diseases, cardiovascular spasmodic diseases, coronary artery spasm, hypertension, pulmonary hypertension, renal diseases, cardiac infarction, angina pectoris, arrhythmia, portal hypertension, varicosity and the like), arteriosclerosis, pulmonary fibrosis, hepatic fibrosis, renal fibrosis, respiratory diseases (e.g. bronchial asthma, chronic obstructive pulmonary disease and the like), nephropathy, diabetes, hyperlipidemia and the like.

The Compound of the Present Invention may be administered as a concomitant drug preparation in combination with other drugs for the purpose of; (1) supplementation and/or enhancement of the preventive and/or therapeutic effect of the said Compound of the Present Invention, (2) improvement of the dynamic and absorption of, and lowering of the dose of, the said Compound of the Present Invention, and/or (3) alleviation of side effects of the said Compound of the Present Invention.

The concomitant drug preparations of the Compound of the Present Invention with other drugs may be administered either in the form of a combination drug having a plurality of the drug substances formulated in one pharmaceutical preparation or in the form of separate pharmaceutical preparations individually comprising a plurality of drug substances. Administration in the form of such separate pharmaceutical preparations is understood to include both the simultaneous administration and the intermittent time-lag administration. On the occasion of the intermittent time-lag administration, the Compound of the Present Invention may be administered firstly, followed by other drugs, and vice versa, whereby the individual methods of administration may be the same or different.

Said other drugs may be low-molecular compounds, high-molecular proteins, polypeptides, polynucleotides (DNA, RNA, genes), anti-senses, decoys, antibodies, or vaccines and the like. The other drugs include, for example, a calcium antagonist, endothelin antagonist, a vasodilating agent, an Rho kinase inhibitor, a nitrate drug, a xanthine derivative, prostaglandins, an angiotensin II antagonist, a diuretic, an angiotensin converting enzyme inhibitor, a prostacyclin preparation, a β-blocker, a β-adrenergic agent, an anticholinergic agent, a thrombolytic agent, a thromboxane synthase inhibitor, a thromboxane A2 receptor antagonist, an antioxidant, a radical scavenger, a poly-ADP ribose polymerase (PARP) inhibitor, an astrocyte-function improvement agent, a phosphodiesterase 4 inhibitor, a steroidal agent, an aldsterone antagonist, a leukotriene receptor antagonist, a mediator liberation inhibitor, an anti-histamine agent, a cytokine inhibitor, a Forskolin prepration, an elastase inhibitor, a metalloprotease inhibitor, an expectorant drug, an antibiotic agent and the like, but are not limited thereto. And these other drugs may preferably be suitably selected according to the disease to which the compound of the present invention is applied.

The dose of the other drugs may be suitably selected in relation to the clinically used doses as a reference. The ratio of the Compound of the Present Invention to the other drugs may be suitably selected depending upon the age and weight of an subject to be administered, route of administration, time of administration, targeted disease, symptom or drug combination and the like. For example, approximately 0.01 to 100 parts by weight of the other drugs may be used against 1 part of the Compound of the Present Invention. The other drugs may be administered in combination of one or not less than two being arbitrarily selected from the above-indicated groups of the similar and different types.

The diseases, against which the above-mentioned concomitant drug preparations can produce the preventive and/or therapeutic effects, are not particularly limited and may be any diseases so long as they can attain the supplementation and/or enhancement of the preventive and/or therapeutic effects of the Compound of the Present Invention.

Examples of the other drugs for supplementation and/or enhancement of the preventive and/or therapeutic effects on cerebrovascular spasm diseases and cardiovascular spasm diseases include a calcium antagonist, a thrombolytic agent, a thromboxane synthase inhibitor, an endothelin antagonist, an antioxidant agent, a radical scavenger, a PARP inhibitor, an astrocyte-function improvement agent, a vasodilating agent, an Rho kinase inhibitor and the like. Examples of the other drugs for supplementation and/or enhancement of the preventive and/or therapeutic effects on hypertension include a calcium antagonist, an angiotensin II antagonist, an angiotensin converting enzyme inhibitor, a diuretic, a phosphodiesterase 4 inhibitor, prostaglandins (hereinafter from time to time referred to briefly as PG or PGs), an aldosterone antagonist and the like. Examples of the other drugs for supplementation and/or enhancement of the preventive and/or therapeutic effects on pulmonary hypertension include an endothelin antagonist, a prostacyclin prearation and the like.

Examples of the other drugs for supplementation and/or enhancement of the preventive and/or therapeutic effects on angina pectoris include a nitrate drug, a β-blocker, a calcium antagonist and a vasodialator and the like.

Examples of the other drugs for supplementation and/or enhancement of the preventive and/or therapeutic effects on bronchial asthma or chronic obstructive pulmonary disease include a phosphodiesterase 4 inhibitor, a steroidal drug, a β-adrenergic agent, a leukotriene receptor antagonist, a thromboxane synthase inhibitor, a thromboxane A2 receptor antagonist, a mediator liberation inhibitor, an anti-histamine drug, a xanthine derivative, an anti-cholinergic agent, a cytokine inhibitor, prostaglandins, a Forskolin preparation, an elastase inhibitor, a metalloprotease inhibitor, an expectorant drug and an antibiotic agent and the like.

Examples of the calcium antagonists include nifedipine, benidipine hydrochloride, diltiazem hydrochloride, verapamil hydrochloride, nisoldipine, nitrendipine, bepridil hydrochloride, amlodipine besilate, lomerizine hydrochloride and efonidipine hydrochloride and the like.

Examples of the thrombolytic drugs include alteprase, urokinase, tisokinase, nasaruplase, nateplase, tissue plasminogen activator, pamiteplase and monteplase and the like.

Examples of the thromboxane synthase inhibitors include ozagrel hydrochloride, and imitrodast sodium and the like.

Examples of the radical scavengers include radicut and the like.

Examples of the PARP inhibitors include, 3-aminobenzamide or 1,3,7-trimethylxanthine (caffeine), PD-141076 and PD-141703 and the like.

Examples of the astrocyte-function improvement agents include ONO-2506 and the like.

Examples of the Rho kinase inhibitors include fasudil hydrochloride and the like.

Examples of the angiotensin II antagonists include losartan, candesartan, valsartan, irbesartan, olmesartan and telmesartan and the like.

Examples of the angiotensin converting enzyme inhibitors include alacepril, imidapril hydrochloride, quinapril hydrochloride, temocapril hydrochloride, delapril hydrochloride, benazepril hydrochloride, captopril, trandolapril, perindopril erubumine, enalapril maleate and lisinopril and the like.

Examples of the diuretics include mannitol, furosemide, acetazolamide, diclofenamide, methazolamide, trichlormethiazide, mefruside, spironolactone and aminophylline and the like.

Examples of the phospodiesterase 4 inhibitor include rolipram, cilomilast, Bay19-8004, NIK-616, roflumilast (BY-217), cipamfylline (BRL-61063), atizoram (CP-80633), SCH-351591, YM-976, V-11294A, PD-168787, D-4396 and IC-485 and the like.

Examples of the PGs include a PG receptor agonist and PG receptor antagonist and the like.

Examples of the PG receptors include PGE receptors (EP1, EP2, EP3, EP4), a PGD receptor (DP, CRTH2), PGF receptor (FP), PGI receptor (IP) and TX receptor (TP) and the like.

Examples of the aldosterone antagonists include drospirenon, metyrapone, potassium canrenoate, canrenone, eplerenone and ZK-91857 and the like.

Examples of the prostacyclin preparations include treprostinil sodium, epoprestenol sodium and beraprost sodium and the like.

Examples of the nitrate drugs include amyl nitrite, nitroglycerine, isosorbide dinitrate and the like.

Examples of the β-blockers include, bupranolol hydrochloride, bufetolol hydrochloride, oxprenolol hydrochloride, atenolol, bisoprolol fumarate, betaxolol hydrochloride, bevantolol hydrochloride, metoprolol tartrate, acebutolol hydrochloride, celiprolol hydrochloride, nipradilol, tilisolol hydrochloride, nadolol, propranolol hydrochloride, indenolol hydrochloride, carteolol hydrochloride, pindolol, bunitrolol hydrochloride, arotinolol hydrochloride and carvedilol hydrochloride and the like.

Examples of the vasodilating agents include diltiazem hydrochloride, trimetazidine hydrochloride, dipyridamole, ethanofen hydrochloride, dilazep hydrochloride, trapidil, nicorandil and the like.

Examples of the steroidal drugs include, in the form of a preparation for internal use or an injectable solution, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like. Examples of the steroidal drugs include, in the form of an inhalant, beclomethasone propionate, fluticasone propionate, budesonide, flunisolide, triamcinolone, ST-126P, ciclesonide, dexamethasone palomitionate, mometasone furancarbonate, prasterone sulfonate, deflazacort, methyl prednisolone sreptanate, methyl prednisolone sodium succinate and the like.

Examples of the β-adrenergic agonists include fenoterol hydrobromide, salbutamol sulfate, terbutaline sulfate, formoterol fumarate, salmeterol xinafoate, isoproterenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamin hydrochloride, meradrin tartrate, AR-C68397, levosalbutamol, R,R-formoterol, KUR-1246, KUL-7211, AR-C89855, S-1319 and the like.

Examples of the leukotriene receptor antagonists include pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057 and the like.

Examples of the thromboxane A2 receptor antagonists include seratrodast, ramatroban, domitroban calcium hydrate, KT-2-962 and the like.

Examples of the mediator liberation inhibitors include tranilast, sodium cromoglycate, amlexanox, repirinast, ibudilast, dazanolast, potassium pemirolast and the like.

Examples of the anti-histamine drugs include ketotifen fumarate, mequitazine, azelastine hydrochloride, oxatomide terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, auranofin, acrivastin and the like.

Examples of the xanthine derivatives include aminophylline, theophylline, doxofyllin, cipamphylline, diprophylline and the like.

Examples of the anticholinergic agents include ipratropium bromide, oxitropium bromide, futropium bromide, simetropium bromide, temiverine, thiotropium bromide, revatropate (UK-112166) and the like.

Examples of the cytokine inhibitors include suplatast tosylate (Brand Name: IPD) and the like.

Examples of the elastase inhibitors include ONO-5046, ONO-6818, MR-889, PBI-1101, EPI-HNE-4, R-665 and the like.

Examples of the expectorant drugs include carbocysteine, ambroxol hydrochloride, controlled release preparation of ambroxol hydrochloride, methylcysteine hydrochloride, acetyl cysteine, L-ethylcysteine hydrochloride, tyloxapol and the like.

Examples of the endothelin antagonists include BE-18257B, BQ-123, FR139317, bosentan, SB209670 and the like.

Examples of the metalloprotease inhibitors include KB-R7785, S-3536 and the like.

Examples of the antibiotic drugs include cefuroxime sodium, meropenem trihydrate, netilmicin sulfate, sisomicin sulfate, ceftibuten, PA-1806, IB-367, tobramycin, PA-1420, doxorubicin, astromicin sulfate, cefetamet pivoxil hydrochloride and the like. Examples of the inhalant antibiotic drugs include PA-1806, IB-367, tobramycin, PA-1420, doxorubicin, astromicin sulfate, cefetamet pivoxil hydrochloride and the like.

Other drugs which act to supplement and/or enhance the preventive and/or therapeutic effects of the Compound of the Present Invention include the drugs which not only have already been found out in the past, but also are to be found out in the future, to exhibit such activities on the basis of the above-described mechanism.

The Compound of the Present Invention or the concomitant drug preparation thereof with other drugs, when used for the above-described purposes, is ordinarily administered systemically or topically in the form of oral or parenteral preparation.

The Compound of the Present Invention, whose dosage may vary depending upon the age, body weight and symptom of a patient to be treated, the intended therapeutic effect, administration route and duration of the treatment, etc., preferably is generally administered to a human adult orally in a dose ranging from about 100 μg to about 1000 mg once to several times a day, to a human adult parenterally in a dose of ranging from 50 μg to about 500 mg once to several times a day, or to a human adult through sustained intravenous infusion over the period of time ranging from about 1 hour to 24 hours a day.

As has been described in the above, naturally, the dosage may change with a variety of conditions. Consequently, the Compound of the Present Invention in some instances can produce the intended effect satisfactorily even in doses lower than the above-mentioned doses and is in other instances required to be administered in doses in excess of the above dose ranges.

The Compound of the Present Invention or the concomitant drug preparation thereof with other drugs is administered as used in the dosage forms of solid pharmaceutical preparation or liquid solution for internal use for the purpose of oral administration, or in the dosage forms of an injectable solution, a topical preparation, a suppository, an ophthalmic solution, an inhalant, etc. for the purpose of parenteral administration.

The solid pharmaceutical preparation for internal use for the purpose of oral administration includes, for example, a tablet, a pill, a capsule, powders, granules, etc. As the capsule, there may be mentioned, for example, a hard capsule and a soft capsule.

In such a solid pharmaceutical preparation for internal use, one or more of the active substances is/are used as such or by mixing them with, for example, an excipient (e.g. lactose, mannnitol, glucose, microcrystalline cellulose, starch and the like), a binder (e.g. hydroxypropyl cellulose, polyvinyl pyrrolidone, magnesium metasilicate aluminate and the like), a disintegrating agent (e.g. cellulose calcium glycolate and the like), a lubricating agent (e.g. magnesium stearate and the like), a stabilizer and a dissolving adjuvant (e.g. glutamic acid, asparatic acid and the like), followed by processing into the prearation by the conventional procedures. The solid pharmaceutical preparation, if necessary, may be covered with a coating agent (e.g. sugar, gelatin, hydroxypropyl cellulose, hydroxypropyl cellulose phthalate and the like) or with two or more layers. A capsule consisting of a bioabsorbable material, such as gelatin, is also included.

The liquid solution for internal use includes, for example, a pharmaceutically acceptable aqueous solution, a suspension, an emulsion, syrup, elixir and the like. In such a liquid solution, one or more active compound(s) is/are dissolved, suspended or emulsified in an ordinarily used diluent (e.g. purified water, ethanol or a mixture thereof and the like). Furthermore, such liquid solution may also contain a wetting agent, a suspending agent, an emulsifying agent, a sweetening agent, a flavoring agent, a perfuming (aromatic) agent, a buffering agent, a preservative, a buffering agent and the like.

The topical preparation for external use for the purpose of parenteral administration includes, for example, an ointment, gel, cream, poultice, patch, liniment, nebula, inhalant, spray, aerosol, an ophthalmic solution or collunarium and the like. These contain one or more active substances and are prepared by the known methods or in accordance with the usually employed formulations.

The ointment is prepared by the known methods or in accordance with the usually employed formulations. For example, it is prepared by mixing with, or melting in, a base one or more active substances. The ointment base is selected from the bases which are known or are normally used: it is used by mixing one or not less than two of the bases being selected from higher fatty acids or higher fatty acid esters (e.g. adipic acid, myristic acid, palmitic acid, stearic acid, oleic acid, adipates, myristates, palmitates, stearares, oleates and the like), waxes (e.g. beeswax, whale wax, ceresin and the like), sufactants (e.g. polyoxyethylenealkylether phosphate and the like), higher alcohols (e.g. cetyl alcohol, stearyl alcohol, cetostearyl alcohol and the like), silicon oils (e.g. dimethylpolysiloxane and the like), hydrocarbons (e.g. hydrophilic vaseline, white vaseline, purified lanolin, liquid petrolatum and the like), glycols (e.g. ethyleneglycol, diethyleneglycol, propyleneglycol, polyethyleneglycol, macrogol and the like), vegetable oils (e.g. castor oil, oliveoil, sesame oil, turpentine and the like), animal oils (e.g. mink oil, yolk oil, squalane, squalene and the like), water, absorption promoters, protectives for skin eruption and the like. Furthermore, it may contain ahumectant and emollient, preservative, stabilizer, antioxidant, flavoring agentand the like.

The gel is prepared by the known methods or in accordance with the usually employed formulations. For example, the gel is prepared by melting one or more of the active substance(s) in the base. The gel base is selected from those which are known or are ordinarily used, such as lower alcohols (e.g. ethanol, isopropyl alcohol and the like), gelling agents (e.g. carboxymethyl-cellulose, hydroxyethylcellulose, hydroxypropylcellulose, ethylcellulose and the like), acid-neutralizing agents (e.g. triethanolamine, diisopropanolamine and the like), surfactants (e.g. polyoxyethylene glycol stearate and the like), gums, water, absorption promoters, protectives against skin eruption and the like. and is used alone or as an admixture of two or more thereof. Furthermore, such gel base may include a preservative, an antioxidant, a flavoring agent and the like.

The cream is prepared by the known methods or in accordance with the usually employed formulations, and is prepared, for example, by melting or emulsifying one or more active substances in a base. The cream base is selected from those which are known or are ordinarily used, such as higher fatty acid esters, lower alcohols, hydrocarbons, polyhydric alcohols (e.g. propylene glycol, 1,3-butylene glycol and the like), higher alcohols (e.g. 2-hexyldecanol, cetyl alcohol and the like), emulsifying agents (e.g. polyoxyethylenated alkylethers, fatty acid esters and the like), water, absorption promoters, protectives against skin eruption and the like, and is used alone or as an admixture of two or more thereof. Furthermore, such cream base may include a preservative, an antioxidant, a flavoring agent and the like.

The poultice is prepared by the known methods or in accordance with the usually employed formulations, and is prepared, for example, by melting one or more active substances in a base and spreading for application the mixture on a supporting material. The poultice base is selected from those which are known or are ordinarily used, such as thickeners (e.g. polyacrylic acid, polyvinyl pyrrolidone, gum arabic, starch, gelatin, methylcellulose and the like), humectants and emollients (e.g. urea, glycerin, propylene grycol and the like), filler S (e.g. kaolin, zinc oxide, talc, calcium carbonate, magnesium carbonate and the like), water, solubilizing agents, tackifiers, protective for skin eruption and the like, and is used alone or as an admixture of two or more thereof.

Furthermore, such poultice base may include a preservative, an antioxidant, a flavoring agent and the like.

The patch is prepared by the known methods or in accordance with the usually employed formulations, and is prepared by melting one or more of the active substance(s) in a base and spreading for application the mixture on a supporting material. The patch base is selected from those which are known or are normally used, such as polymer bases, oils and fats, higher fatty acids, tackifiers, protectives for skin eruption and the like, and is used alone or an admixture of two or more thereof. Furthermore, such patch base may include a preservative agent, an antioxidant, a flavoring agent and the like.

The liniment is prepared by the known methods or in accordance with the usually employed formulations, and is prepared, for example, by dissolving, suspending or emulsifying one or more of active substances in a base consisting of one or more member(s) selected from water, alcohols (e.g. ethanol, polyethylene glycol and the like), higher fatty acids, glycerin, soaps, emulsifiers, suspending agents and the like.

The nebula, inhalant or spray preparation may contain, in addition to the generally used diluents, a stabilizer such as sodium bisulfite, an isotonizing buffer and an isotonic agent such as sodium chloride, sodium citrate or citric acid. The manufacturing process for spray preparations is described in detail, for example, in U.S. Pat. Nos. 2,868,691 and 3,095,355.

Examples of the injectable solution for the purpose of parenteral administration include solutions, suspensions, emulsions and solid injections to be applied by dissolving or suspending in a solvent on the occasion of use. The injectable solutions are used by dissolving, suspending or emulsifying one or more of the active substances in a solvent. Examples of the solvent include distilled water for injection, saline solution, vegetable oils, propylene glycol, polyethylene glycol, alcohols (e.g. ethanol and the like) and combinations thereof.

Such injectable solutions may additionally contain a stabilizer, a solubilizer (e.g. glutamic acid, aspartic acid, Polysorbate 80 (the registered trademark) and the like), a suspending agent, emulsifyer, pain-soothing agent, a buffering agent, a preservative and the like. These are prepared by sterilization in the final processing step or by the aseptic manipulation. Alternatively, such injectable solutions can be utilized by preparing a sterile solid, such as freeze-dried product and dissolving, prior to use, the same in sterilized or sterile distilled water for injection.

The ophthalmic solution for the purpose of parenteral administration include, for example, ophthalmic solution, suspension-type ophthalmic solution, emulsion-type ophthalmic solution, ophthalmic solution for dissolution on the occasion of use or ophthalmic ointment and the like.

These ophthalmic solutions are prepared by following the known procedures.

For example, use is made by dissolving, suspending or emulsifying one or more of the active substances in the solvent. The solvent for ophthalmic solution includes, for example, sterile purified water, saline solution, other aqueous solvents or non-aqueous solvents for injection (e.g. vegetable oils and the like), and combinations thereof. The ophthalmic solutions may contain an isotonic agent (e.g. sodium chloride, concentrated glycerin and the like), buffering agent (e.g. sodium phosphate, sodium acetate and the like), sufactant (e.g. Polysorbate 80 (the registered trademark), polyoxyl stearate 40, polyoxyethylenated hardened castor oil and the like), stabilizer (e.g. sodium citrate, edentate sodium and the like), preservative (e.g. benzalkonium chloride, paraben and the like) and the like, which are suitably selected as the case may be.

These are prepared by sterilization in the final processing step or by the aseptic manipulation. And, such ophthalmic solutions may be utilized by preparing a sterile solid, such as freeze-dried or lyophilized product and dissolving, prior to use, the same in sterilized or sterile purified water or other solvents.

The inhalant for the purpose of parenteral administration includes an aerosol agent, powder for inhalation or liquid for inhalation, and such liquid for inhalation may be formulated into such a dosage form as may be used by dissolving or suspending, on the occasion of use, the same in water or other suitable media.

These inhalants are prepared by the known methods.

The liquid for inhalation is prepared for example by suitably selecting, as the case may be, a preservative (e.g. benzalkonium chloride, parabens and the like), coloring agent, buffering agent (e.g. sodium phosphate, sodium acetate and the like), isotonic agent (e.g. sodium chloride, concentrated glycerin and the like), thickener (e.g. carboxy vinyl polymer and the like), absorption promoter and the like.

The dry powder for inhalation is prepared by suitably selecting, as the case may be, a lubricant (e.g. stearic acid and salt thereof and the like), binder (e.g. starch, dextrin and the like), coloring agent, preservative (e.g. benzalkonium chloride, parabens and the like), absorption promoter and the like.

On the occasion of administration of the liquid for inhalation, the spraying devices (e.g. atomizer, nebulizer and the like) are usually used, while in the case of administration of the dry powder for inhalation, the inhalation-administering devices for dry powders are generally employed.

Other compositions for parenteral administration include a suppository for intrarectal application and pessary for intravaginal administration which comprises one or more of the active substances and may be processed by the conventional methods.

The present invention is to be illustrated below in detail by way of Examples, but the present invention shall not be limited thereto.

The parenthesized solvents, which are described under the chromatographic separatory and TLC procedures, are understood to designate the eluting or developing solvents, with the ratios being expressed on a volume basis.

The NMR data denote the data of $^1$H-NMR, unless otherwise specified.

The parenthesized solvents, which are indicated under NMR measurements, are understood to signify the solvents used for the measurements.

MS, unless otherwise specified, was conducted using ESI (electron spray ion) method to detect the positive ions (pos.) alone.

The conditions for HPLC are as follows:

(A) Condition A (Analysis)

Equipment used: Waters LC/MS

Column: Xterra (the registered trade mark) MS $C_{18}$ 5 μm, 4.6×50 mm I.D.

Flow rate: 3 mL/min

Eluting solvent:

Solvent A: 0.1% aqueous trifuloroacetic acid solution

Solvent B: 0.1% trifuloroacetic acid-acetonitrile solution (A time-course change of the eluting solvent composition in vol. % is shown below)

| Time (min) | solvent A | solvent B |
|---|---|---|
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

(2) Condition B (Analysis)
Epuipment used: Waters LC/MS
Column: Xterra (the registered trademark) MS $C_{18}$ 5 μm, 4.6×50 mm I.D.
Flow rate: 3 mL/min
Eluting solvent:
Solvent A: 10 mM aqueous ammonium carbonate solution
Solvent B: acetonitrile

| Time (min) | solvent A | solvent B |
|---|---|---|
| 0 | 95 | 5 |
| 0.5 | 95 | 5 |
| 3 | 0 | 100 |
| 3.5 | 0 | 100 |
| 3.51 | 95 | 5 |
| 7 | 95 | 5 |

In the HPLC, all the measurements were performed under Condition A, unless the conditions were otherwise specified particularly.

The compounds described in the present specification were named by use of ACD/Name or ACD/Name Batch (both are the registered trademarks, manufactured by Advanced Chemistry Development Inc.) or in accordance with the IUPAC nomenclature. For example, the compound of the formula:

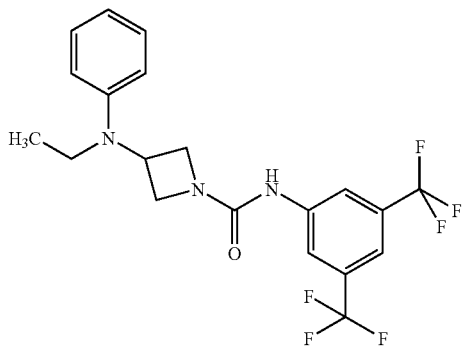

was named N-[3,5-bis(trifluoromethyl)phenyl]-3-[ethyl(phenyl)amino]azetidine-1-carboxamide.

EXAMPLE 1

Tert-butyl 4-[1-(diphenylmethyl)azetidin-3-yl]piperazine-1-carboxylate

Potassium carbonate (26 g) was added to a solution of tert-butyl piperazine-1-carboxylate (7.7 g) in acetonitrile (100 ML), to which a suspension of 1-(diphenylmethyl)azetidin-3-yl methanesulfonate (12.05 g) in tetrahydrofuran (30 mL) was added at room temperature, and the mixture was stirred for 4 hours at 100° C., and then concentrated. To the resulting residue was added water, and the mixture was extracted with ethyl acetate twice. The extract was dried over anhydrous magnesium sulfate and concentrated. The obtained residue was subjected to column chromatography on silica gel (hexane:ethyl acetate=3:1→1:2), and the product was washed with tert-butyl methyl ether and collected by filtration to give the title compound (10.68 g) having the following physical data.

TLC:Rf 0.55 (hexane:ethyl acetate=1:1).

EXAMPLE 2

Tert-butyl 4-azetidin-3-ylpiperazine-1-carboxylate

Under atmosphere of argon, a solution of the compound, prepared in Example 1 (8.68 g), in methanol (50 ml)/acetic acid (8.5 mL) was added to a suspension of 20% palladium hydroxide (1.74 g, wet) in methanol (5 mL). The mixture was stirred for 5 hours under atmosphere of hydrogen at 5 atm. The reaction solution was filtered and concentrated. To the residue was added tert-butyl methyl ether, and the mixture was extracted with water. To the aqueous layer was added 5N aqueous solution of sodium hydroxide, and the solution was extracted with dichloromethane. The organic layer was dried over anhydrous magnesium sulfate and concentrated to give the title compound (5.1 g) having the following physical data.

TLC:Rf 0.41 (ethyl acetate:acetic acid:water=3:1:1).

EXAMPLE 3

Tert-butyl 4-[1-({[3,5-bis(trifluoromethyl)phenyl]amino}carbonyl)azetidin-3-yl]piperazine-1-carboxylate

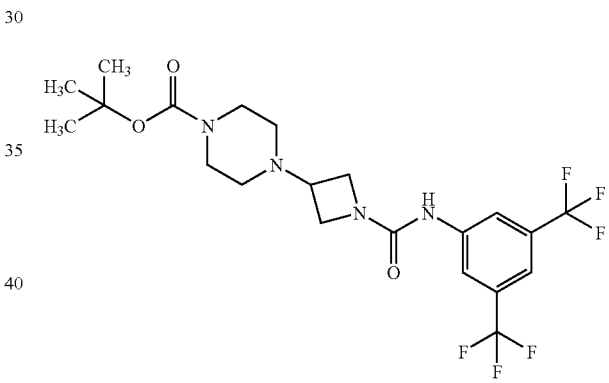

To a solution of the compound prepared in Example 2 (986 mg) in tetrahydrofuran (12 mL) was dropwise added 1-isocyanato-3,5-bis(trifluoromethyl)benzene (0.85 mL), and the mixture was stirred for 30 minutes. The reaction solution was concentrated. The residue was purified by column chromatography on silica gel (hexane:ethyl acetate=1:1) to give the compound of the present invention (1.413 g) having the following physical data.

TLC:Rf 0.21 (hexane:ethyl acetate=1:1);
NMR (CDCl$_3$):δ 1.47 (s, 9H), 2.34 (m, 4H), 3.24 (m, 1H), 3.47 (m, 4H), 3.98 (dd, J=8.00, 5.50 Hz, 2H), 4.11 (t, J=8.00 Hz, 2H), 6.26 (s, 1H), 7.51 (s, 1H), 7.91 (s, 2H).

EXAMPLES 3(1) to 3(809)

Each of the following compounds of the present invention was prepared from an azetidine derivative corresponding to the compound prepared in Example 2 and an isocyanate derivative corresponding to 1-isocyanato-3,5-bis(trifluoromethyl)benzene using a procedure analogous to that described for Example 3.

EXAMPLE 3(1)

N-[3,5-Bis(trifluoromethyl)phenyl]-3-(4-phenylpiperazin-1-yl)azetidine-1-carboxamide

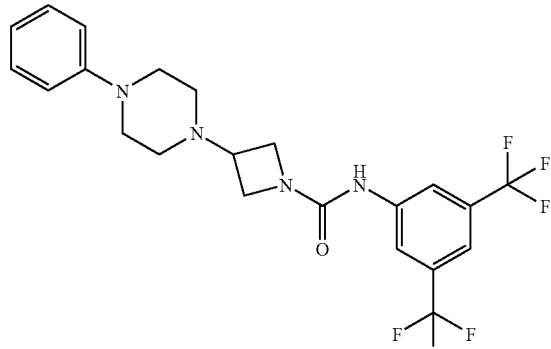

TLC:Rf 0.30 (hexane:ethyl acetate=1:1);
NMR (CDCl$_3$): δ 2.58 (m, 4H), 3.24 (m, 4H), 3.33 (m, 1H), 4.04 (dd, J=8.00, 5.00 Hz, 2H), 4.15 (t, J=8.00 Hz, 2H), 6.25 (s, 1H), 6.93 (m, 3H), 7.28 (m, 2H), 7.51 (s, 1H), 7.92 (s, 2H).

EXAMPLE 3(2)

N-[3,5-Bis(trifluoromethyl)phenyl]-3-[4-(2-methoxyphenyl)piperazin-1-yl]azetidine-1-carboxamide TLC:Rf 0.22 (hexane:ethyl acetate=1:1);
NMR (CDCl$_3$): δ 2.62 (m, 4H), 3.14 (m, 4H), 3.36 (m, 1H), 3.87 (s, 3H), 4.04 (dd, J=8.00, 5.00 Hz, 2H), 4.14 (t, J=8.00 Hz, 2H), 6.32 (s, 1H), 6.88 (d, J=7.50 Hz, 1H), 6.94 (m, 2H), 7.03 (m, 1H), 7.51 (s, 1H), 7.93 (s, 2H).

EXAMPLE 3(3)

N-[3,5-Bis(trifluoromethyl)phenyl]-3-[4-(3-methoxyphenyl)piperazin-1-yl]azetidine-1-carboxamide TLC:Rf 0.29 (hexane:ethyl acetate=1:1);
NMR (CDCl$_3$): δ 2.55 (m, 4H), 3.23 (m, 4H), 3.30 (m, 1H), 3.80 (s, 3H), 4.02 (dd, J=8.00, 5.00 Hz, 2H), 4.13 (t, J=8.00 Hz, 2H), 6.45 (m, 3H), 6.55 (m, 1H), 7.19 (t, J=8.00 Hz, 1H), 7.51 (s, 1H), 7.92 (s, 2H).

EXAMPLE 3(4)

N-[3,5-Bis(trifluoromethyl)phenyl]-3-[4-(4-methoxyphenyl)piperazin-1-yl]azetidine-1-carboxamide TLC:Rf 0.17 (hexane:ethyl acetate=1:1);
NMR (CDCl$_3$): δ 2.58 (m, 4H), 3.13 (m, 4H), 3.32 (m, 1H), 3.77 (s, 3H), 4.03 (dd, J=8.00, 5.00 Hz, 2H), 4.14 (t, J=8.00 Hz, 2H), 6.28 (s, 1H), 6.85 (d, J=9.00 Hz, 2H), 6.91 (d, J=9.00 Hz, 2H), 7.51 (s, 1H), 7.92 (s, 2H).

EXAMPLE 3(5)

N-[3,5-Bis(trifluoromethyl)phenyl]-3-{4-[3-(trifluoromethoxy)phenyl]piperazine-1-yl}azetidine-1-carboxamide TLC:Rf 0.39 (hexane:ethyl acetate=1:1);
NMR (CDCl$_3$): δ 2.56 (m, 4H), 3.25 (m, 4H), 3.32 (m, 1H), 4.03 (dd, J=8.00, 5.00 Hz, 2H), 4.15 (t, J=8.00 Hz, 2H), 6.22 (s, 1H), 6.71 (m, 2H), 6.82 (m, 1H), 7.26 (m, 1H), 7.51 (s, 1H), 7.92 (s, 2H).

EXAMPLE 3(6)

N-(2-Ethylphenyl)-3-(4-methylpiperazin-1-yl)azetidine-1-carboxamide

TLC:Rf 0.26 (ethyl acetate:methanol:triethylamine=10:1:2);
NMR (CDCl$_3$): δ 1.24 (t, J=7.50 Hz, 3H), 2.33 (s, 3H), 2.56 (m, 10H), 3.21 (m, 1H), 3.89 (dd, J=8.00, 5.50 Hz, 2H), 4.00 (t, J=8.00 Hz, 2H), 5.84 (s, 1H), 7.06 (m, 1H), 7.19 (m, 2H), 7.69 (d, J=8.00 Hz, 1H).

EXAMPLE 3(7)

N-(2,4-Dimethylphenyl)-3-(4-methylpiperazin-1-yl)azetidine-1-carboxamide

TLC:Rf 0.23 (ethyl acetate:methanol:triethylamine=10:1:2);
NMR (CDCl$_3$): δ 2.20 (s, 3H), 2.27 (s, 3H), 2.31 (s, 3H), 2.43 (m, 8H), 3.18 (m, 1H), 3.87 (dd, J=8.00, 5.50 Hz, 2H), 3.97 (t, J=8.00 Hz, 2H), 5.69 (s, 1H), 6.97 (m, 2H), 7.47 (d, J=8.00 Hz, 1H).

EXAMPLE 3(8)

3-(4-Methylpiperazin-1-yl)-N-[3-(trifluoromethyl)phenyl]azetidine-1-carboxamide

TLC:Rf 0.21 (ethyl acetate:methanol:triethylamine=10:1:2);
NMR (CDCl$_3$): δ 2.32 (s, 3H), 2.47 (m, 8H), 3.25 (m, 1H), 3.96 (dd, J=8.00, 5.50 Hz, 2H), 4.08 (t, J=8.00 Hz, 2H), 6.07 (s, 1H), 7.26 (m, 1H), 7.39 (t, J=8.00 Hz, 1H), 7.64 (m, 2H).

EXAMPLE 3(9)

N-(3,5-Dimethylphenyl)-3-(4-methylpiperazin-1-yl)azetidine-1-carboxamide

TLC:Rf 0.21 (ethyl acetate:methanol:triethylamine=10:1:2);
NMR (CDCl$_3$): δ 2.27 (s, 6H), 2.32 (s, 3H), 2.46 (m, 8H), 3.22 (m, 1H), 3.92 (dd, J=8.00, 5.50 Hz, 2H), 4.03 (t, J=8.00 Hz, 2H), 5.85 (s, 1H), 6.68 (s, 1H), 7.00 (s, 2H).

EXAMPLE 3(10)

Methyl 3-({[3-(4-methylpiperazin-1-yl)azetidin-1-yl]carbonyl}amino)benzoate

TLC:Rf 0.16 (ethyl acetate:methanol:triethylamine=10:1:2);
NMR (CDl₃): δ 2.35 (s, 3H), 2.51 (m, 8H), 3.26 (m, 1H), 3.90 (s, 3H), 3.96 (dd, J=8.00, 5.00 Hz, 2H), 4.08 (t, J=8.00 Hz, 2H), 6.05 (s, 1H), 7.36 (t, J=8.00 Hz, 1H), 7.70 (m, 1H), 7.80 (m, 1H), 7.86 (m, 1H).

EXAMPLE 3(11)

N-(2,4-Dimethylphenyl)-3-pyrrolidin-1-ylazetidine-1-carboxamide

TLC:Rf 0.68 (ethyl acetate:methanol:triethylamine=10:1:2);
NMR (CDCl₃): δ 1.83 (m, 4H), 2.20 (s, 3H), 2.27 (s, 3H), 2.50 (m, 4H), 3.31 (m, 1H), 3.90 (dd, J=8.00, 5.00 Hz, 2H), 4.02 (t, J=8.00 Hz, 2H), 5.69 (s, 1H), 6.98 (m, 2H), 7.49 (d, J=8.00 Hz, 1H).

EXAMPLE 3(12)

N-(3,5-Dichlorophenyl)-3-(4-phenylpiperidin-1-yl)azetidine-1-carboxamide

TLC:Rf 0.37 (hexane:ethyl acetate=1:1);
NMR (CDCl₃): δ 1.82 (m, 6H), 2.52 (m, 1H), 2.91 (m, 2H), 3.17 (m, 1H), 3.95 (dd, J=8.24, 7.87 Hz, 2H), 4.06 (t, J=7.87 Hz, 2H), 6.61 (s, 1H), 6.98 (t, J=1.83 Hz, 1H), 7.20 (m, 3H), 7.30 (m, 2H), 7.39 (d, J=1.83 Hz, 2H).

EXAMPLE 3(13)

3-(2,3-Dihydro-1H-indol-1-yl)-N-[3-(trifluoromethyl)phenyl]azetidine-1-carboxamide TLC:Rf 0.61 (hexane:ethyl acetate=1:1);
NMR (CDl₃): δ 3.00 (t, J=8.24 Hz, 2H), 3.43 (t, J=8.24 Hz, 2H), 4.28 (m, 5H), 6.29 (s, 1H), 6.39 (d, J=7.69 Hz, 1H), 6.75 (m, 1H), 7.07 (t, J=7.69 Hz, 1H), 7.12 (d, J=7.87 Hz, 1H), 7.26 (m, 1H), 7.38 (t, J=8.06 Hz, 1H), 7.63 (d, J=8.06 Hz, 1H), 7.68 (s, 1H).

EXAMPLE 3(14)

N-(3,5-Dichlorophenyl)-3-(2,3-dihydro-1H-indol-1-yl)azetidine-1-carboxamide

TLC:Rf 0.73 (hexane:ethyl acetate=1:1);
NMR (CDCl₃): δ 3.01 (t, J=8.24 Hz, 2H), 3.43 (t, J=8.24 Hz, 2H), 4.25 (m, 5H), 6.12 (s, 1H), 6.38 (d, J=7.88 Hz, 1H), 6.75 (m, 1H), 7.01 (t, J=1.83 Hz, 1H), 7.07 (t, J=7.88 Hz, 1H), 7.13 (d, J=7.32 Hz, 1H), 7.38 (d, J=1.83 Hz, 2H).

EXAMPLE 3(15)

N-[3,5-Bis(trifluoromethyl)phenyl]-3-(2,3-dihydro-1H-indol-1-yl)azetidine-1-carboxamide TLC:Rf 0.82 (hexane:ethyl acetate=1:1);
NMR (CDCl₃): δ 3.02 (t, J=8.05 Hz, 2H), 3.45 (t, J=8.05 Hz, 2H), 4.31 (m, 5H), 6.35 (s, 1H), 6.40 (d, J=7.69 Hz, 1H), 6.76 (m, 1H), 7.07 (m, 1H), 7.13 (d, J=7.32 Hz, 1H), 7.52 (s, 1H), 7.93 (s, 2H).

EXAMPLE 3(16)

3-(2,3-Dihydro-1H-indol-1-yl)-N-(3-phenoxyphenyl)azetidine-1-carboxamide

TLC:Rf 0.59 (hexane:ethyl acetate=1:1);
NMR (CDCl₃): δ 2.99 (t, J=8.06 Hz, 2H), 3.42 (t, J=8.06 Hz, 2H), 4.22 (m, 5H), 6.10 (s, 1H), 6.38 (d, J=7.69 Hz, 1H), 6.68 (m, 1H), 6.74 (m, 1H), 7.01 (m, 2H), 7.11 (m, 5H), 7.21 (m, 1H), 7.32 (m, 2H).

EXAMPLE 3(17)

N-[3,5-Bis(trifluoromethyl)phenyl]-3-[methyl(phenyl)amino]azetidine-1-carboxamide TLC:Rf 0.82 (hexane:ethyl acetate=1:1);
NMR (CDCl₃): δ 2.91 (s, 3H), 4.09 (m, 2H), 4.31 (t, J=7.50 Hz, 2H), 4.42 (m, 1H), 6.50 (m, 1H), 6.76 (d, J=7.87 Hz, 2H), 6.89 (m, 1H), 7.27 (m, 2H), 7.50 (s, 1H), 7.91 (s, 2H).

EXAMPLE 3(18)

N-[3,5-Bis(trifluoromethyl)phenyl]-3-[ethyl(phenyl)amino]azetidine-1-carboxamide TLC:Rf 0.86 (hexane:ethyl acetate=1:1);
NMR (CDCl₃): δ 1.05 (t, J=7.14 Hz, 3H), 3.35 (q, J=7.14 Hz, 2H), 3.98 (m, 2H), 4.29 (t, J=7.69 Hz, 2H), 4.40 (m, 1H), 6.42 (s, 1H), 6.75 (d, J=7.32 Hz, 2H), 6.90 (t, J=7.32 Hz, 1H), 7.26 (m, 2H), 7.49 (s, 1H), 7.90 (s, 2H).

EXAMPLE 3(19)

3-{4-[4-(Trifluoromethoxy)phenyl]piperazin-1-yl}-N-[3-(trifluoromethyl)phenyl]azetidine-1-carboxamide TLC:Rf 0.60 (chloroform:methanol=10:1);
NMR (CDCl₃): δ 2.54 (m, 4H), 3.21 (m, 4H), 3.30 (m, 1H), 4.00 (dd, J=7.69, 5.31 Hz, 2H), 4.12 (t, J=7.69 Hz, 2H), 6.19 (s, 1H), 6.89 (d, J=8.42 Hz, 2H), 7.12 (d, J=8.42 Hz, 2H), 7.29 (d, J=7.87 Hz, 1H), 7.39 (t, J=7.87 Hz, 1H), 7.64 (d, J=7.87 Hz, 1H), 7.66 (s, 1H).

EXAMPLE 3(20)

N-(3,5-Dimethylphenyl)-3-{4-[4-(trifluoromethoxy)phenyl]piperazin-1-yl}azetidine-1-carboxamide TLC:Rf 0.64 (chloroform:methanol=10:1);
NMR (CDCl₃): δ 2.27 (s, 6H), 2.55 (m, 4H), 3.21 (m, 4H), 3.27 (m, 1H), 3.96 (dd, J=8.06, 5.31 Hz, 2H), 4.07 (t, J=8.06 Hz, 2H), 5.92 (s, 1H), 6.68 (s, 1H), 6.89 (d, J=8.24 Hz, 2H), 7.02 (s, 2H), 7.12 (d, J=8.24 Hz, 2H).

EXAMPLE 3(21)

N-[3,5-Bis(trifluoromethyl)phenyl]-3-{4-[4-(trifluoromethoxy)phenyl]piperazin-1-yl}azetidine-1-carboxamide TLC:Rf 0.48 (hexane: ethyl acetate=3:7);
NMR (CDCl₃): δ 2.56 (t, J=4.95 Hz, 4H), 3.21 (t, J=4.95 Hz, 4H), 3.32 (m, 1H), 4.03 (dd, J=8.32, 5.13 Hz, 2H), 4.14 (t, J=8.32 Hz, 2H), 6.37 (s, 1H), 67.89 (d, J=9.15 Hz, 2H), 7.12 (d, J=9.15 Hz, 2H), 7.51 (s, 1H), 7.92 (s, 2H).

EXAMPLE 3(22)

N-Phenyl-3-{4-[4-(trifluoromethoxy)phenyl]piperazin-1-yl}azetidine-1-carboxamide HPLC retention time (min.):3.36; MS:421 (M+H)$^+$.

EXAMPLE 3(23)

N-Butyl-3-{4-[4-(trifluoromethoxy)phenyl]piperazin-1-yl}azetidine-1-carboxamide

HPLC retention time (min.):3.31; MS:401 (M+H)$^+$.

EXAMPLE 3(24)

N-(4-Chlorophenyl)-3-{4-[4-(trifluoromethoxy)phenyl]piperazin-1-yl}azetidine-1-carboxamide HPLC retention time (min.):3.44; MS:457, 455 (M+H)$^+$.

EXAMPLE 3(25)

N-(3-Chlorophenyl)-3-{4-[4-(trifluoromethoxy)phenyl]piperazin-1-yl}azetidine-1-carboxamide HPLC retention time (min.):3.44; MS:457, 455 (M+H)$^+$.

EXAMPLE 3(26)

N-Cyclohexyl-3-{4-[4-(trifluoromethoxy)phenyl]piperazin-1-yl}azetidine-1-carboxamide HPLC retention time (min.):3.34; MS:427 (M+H)$^+$.

EXAMPLE 3(27)

N-(2-Chlorophenyl)-3-{4-[4-(trifluoromethoxy)phenyl]piperazin-1-yl}azetidine-1-carboxamide HPLC retention time (min.):3.38; MS:457, 455 (M+H)$^+$.

EXAMPLE 3(28)

N-(3,4-Dichlorophenyl)-3-{4-[4-(trifluoromethoxy)phenyl]piperazin-1-yl}azetidine-1-carboxamide HPLC retention time (min.):3.53; MS:491, 489 (M+H)$^+$.

EXAMPLE 3(29)

3-{4-[4-(Trifluoromethoxy)phenyl]piperazin-1-yl}-N-[3-(trifluoromethyl)phenyl]azetidine-1-carboxamide HPLC retention time (min.):3.51; MS:489 (M+H)$^+$.

EXAMPLE 3(30)

N-(2-Methoxyphenyl)-3-{4-[4-(trifluoromethoxy)phenyl]piperazin-1-yl}azetidine-1-carboxamide HPLC retention time (min.):3.34; MS:451 (M+H)$^+$.

EXAMPLE 3(31)

N-Hexyl-3-{4-[4-(trifluoromethoxy)phenyl]piperazin-1-yl}azetidine-1-carboxamide

HPLC retention time (min.):3.45; MS:429 (M+H)$^+$.

EXAMPLE 3(32)

N-(3-Methoxyphenyl)-3-{4-[4-(trifluoromethoxy)phenyl]piperazin-1-yl}azetidine-1-carboxamide HPLC retention time (min.):3.36; MS:452 (M+H)$^+$.

EXAMPLE 3(33)

N-(4-Methoxyphenyl)-3-{4-[4-(trifluoromethoxy)phenyl]piperazin-1-yl}azetidine-1-carboxamide HPLC retention time (min.):3.34; MS:451 (M+H)$^+$.

EXAMPLE 3(34)

3-{4-[4-(Trifluoromethoxy)phenyl]piperazin-1-yl}-N-[2-(trifluoromethyl)phenyl]azetidine-1-carboxamide HPLC retention time (min.):3.42; MS:489 (M+H)$^+$.

EXAMPLE 3(35)

N-(2,4-Dichlorophenyl)-3-{4-[4-(trifluoromethoxy)phenyl]piperazin-1-yl}azetidine-1-carboxamide HPLC retention time (min.):3.47; MS:491, 489 (M+H)$^+$.

EXAMPLE 3(36)

Ethyl N-[(3-{4-[4-(trifluoromethoxy)phenyl]piperazin-1-yl}azetidine-1-yl)carbonyl]glycinate HPLC retention time (min.):3.22; MS:431 (M+H)$^+$.

EXAMPLE 3(37)

N-(2-Fluorophenyl)-3-{4-[4-(trifluoromethoxy)phenyl]piperazin-1-yl}azetidine-1-carboxamide HPLC retention time (min.):3.34; MS:439 (M+H)$^+$.

EXAMPLE 3(38)

N-(3-Fluorophenyl)-3-{4-[4-(trifluoromethoxy)phenyl]piperazin-1-yl}azetidine-1-carboxamide HPLC retention time (min.):3.38; MS:439 (M+H)$^+$.

EXAMPLE 3(39)

N-Benzyl-3-{4-[4-(trifluoromethoxy)phenyl]piperazin-1-yl}azetidine-1-carboxamide HPLC retention time (min.):3.34; MS:435 (M+H)$^+$.

EXAMPLE 3(40)

N-(4-Fluorophenyl)-3-{4-[4-(trifluoromethoxy)phenyl]piperazin-1-yl}azetidine-1-carboxamide HPLC retention time (min.):3.38; MS:439 (M+H)$^+$.

EXAMPLE 3(41)

3-{4-[4-(Trifluoromethoxy)phenyl]piperazin-1-yl}-N-[4-(trifluoromethyl)phenyl]azetidine-1-carboxamide HPLC retention time (min.):3.53; MS:489 (M+H)$^+$.

EXAMPLE 3(42)

N-(3,5-Dichlorophenyl)-3-{4-[4-(trifluoromethoxy)phenyl]piperazin-1-yl}azetidine-1-carboxamide HPLC retention time (min.):3.56; MS:491, 489 (M+H)$^+$.

EXAMPLE 3(43)

N-(2,5-Dichlorophenyl)-3-{4-[4-(trifluoromethoxy)phenyl]piperazin-1-yl}azetidine-1-carboxamide HPLC retention time (min.):3.47; MS:491, 489 (M+H)$^+$.

EXAMPLE 3(44)

N-Pentyl-3-{4-[4-(trifluoromethoxy)phenyl]piperazin-1-yl}azetidine-1-carboxamide HPLC retention time (min.):3.38; MS:415 (M+H)$^+$.

EXAMPLE 3(45)

N-(2,6-Dichlorophenyl)-3-{4-[4-(trifluoromethoxy)phenyl]piperazin-1-yl}azetidine-1-carboxamide HPLC retention time (min.):3.34; MS:491, 489 (M+H)$^+$.

EXAMPLE 3(46)

N-(2-Phenylethyl)-3-{4-[4-(trifluoromethoxy)phenyl]piperazin-1-yl}azetidine-1-carboxamide HPLC retention time (min.):3.38; MS:449 (M+H)$^+$.

EXAMPLE 3(47)

N-(2,3-Dichlorophenyl)-3-{4-[4-(trifluoromethoxy)phenyl]piperazin-1-yl}azetidine-1-carboxamide HPLC retention time (min.):3.47; MS:491, 489 (M+H)$^+$.

EXAMPLE 3(48)

N-(3-Cyanophenyl)-3-{4-[4-(trifluoromethoxy)phenyl]piperazin-1-yl}azetidine-1-carboxamide HPLC retention time (min.):3.36; MS:446 (M+H)$^+$.

EXAMPLE 3(49)

Ethyl 4-{[(3-{4-[4-(trifluoromethoxy)phenyl]piperazin-1-yl}azetidine-1-yl]carbonyl]amino}benzoate HPLC retention time (min.):3.44; MS:493 (M+H)$^+$.

EXAMPLE 3(50)

N-(4-Phenoxyphenyl)-3-{4-[4-(trifluoromethoxy)phenyl]piperazin-1-yl}azetidine-1-carboxamide HPLC retention time (min.):3.56; MS:513 (M+H)$^+$.

EXAMPLE 3(51)

Ethyl 3-{[(3-{4-[4-(trifluoromethoxy)phenyl]piperazin-1-yl}azetidine-1-yl)carbonyl]amino}benzoate HPLC retention time (min.):3.44; MS:493 (M+H)$^+$.

EXAMPLE 3(52)

N-Isopropyl-3-{4-[4-(trifluoromethoxy)phenyl]piperazin-1-yl}azetidine-1-carboxamide HPLC retention time (min.):3.23; MS:387 (M+H)$^+$.

EXAMPLE 3(53)

N-(3-Phenoxyphenyl)-3-{4-[4-(trifluoromethoxy)phenyl]piperazin-1-yl}azetidine-1-carboxamide HPLC retention time (min.):3.60; MS:513 (M+H)$^+$.

EXAMPLE 3(54)

N-(4-Cyanophenyl)-3-{4-[4-(trifluoromethoxy)phenyl]piperazin-1-yl}azetidine-1-carboxamide HPLC retention time (min.):3.34; MS:446 (M+H)$^+$.

EXAMPLE 3(55)

N-(3,5-Difluorophenyl)-3-{4-[4-(trifluoromethoxy)phenyl]piperazin-1-yl}azetidine-1-carboxamide HPLC retention time (min.):3.44; MS:457 (M+H)$^+$.

EXAMPLE 3(56)

N-[3,5-Bis(trifluoromethyl)phenyl]-3-{4-[4-(trifluoromethoxy)phenyl]piperazin-1-yl}azetidine-1-carboxamide HPLC retention time (min.):3.67; MS:557 (M+H)$^+$.

EXAMPLE 3(57)

N-[3-Fluoro-5-(trifluoromethyl)phenyl]-3-{4-[4-(trifluoromethoxy)phenyl]piperazin-1-yl}azetidine-1-carboxamide HPLC retention time (min.):3.56; MS:534, 507 (M+H)$^+$.

EXAMPLE 3(58)

N-(3-Chloro-5-fluorophenyl)-3-{4-[4-(trifluoromethoxy)phenyl]piperazin-1-yl}azetidine-1-carboxamide HPLC retention time (min.):3.51; MS:475, 473 (M+H)$^+$.

EXAMPLE 3(59)

N-[3-(Cyclopentyloxy)phenyl]-3-{4-[4-(trifluoromethoxy)phenyl]piperazin-1-yl}azetidine-1-carboxamide HPLC retention time (min.):3.58; MS:505 (M+H)$^+$.

EXAMPLE 3(60)

N-[3-(Cyclohexyloxy)phenyl]-3-{4-[4-(trifluoromethoxy)phenyl]piperazin-1-yl}azetidine-1-carboxamide HPLC retention time (min.):3.64; MS:519 (M+H)$^+$.

EXAMPLE 3(61)

N-(2,6-Dichloropyridin-4-yl)-3-{4-[4-(trifluoromethoxy)phenyl]piperazin-1-yl}azetidine-1-carboxamide HPLC retention time (min.):3.44; MS:492, 490 (M+H)$^+$.

EXAMPLE 3(62)

3-(Dimethylamino)-N-hexylazetidine-1-carboxamide

HPLC retention time (min.):2.98; MS:228 (M+H)$^+$.

EXAMPLE 3(63)

3-(Dimethylamino)-N-(4-fluorophenyl)azetidine-1-carboxamide

HPLC retention time (min.):3.05(condition B); MS:238 (M+H)$^+$.

EXAMPLE 3(64)

3-(Dimethylamino)-N-(3-methylphenyl)azetidine-1-carboxamide

HPLC retention time (min.):2.84; MS:234 (M+H)$^+$.

EXAMPLE 3(65)

3-(Dimethylamino)-N-(2-thien-2-ylethyl)azetidine-1-carboxamide

HPLC retention time (min.):2.66; MS:254 (M+H)$^+$.

EXAMPLE 3(66)

3-(Dimethylamino)-N-(4-isopropylphenyl)azetidine-1-carboxamide

HPLC retention time (min.):3.13; MS:523 (2M+H)$^+$, 262 (M+H)$^+$.

EXAMPLE 3(67)

N-(3-Chlorophenyl)-3-(dimethylamino)azetidine-1-carboxamide

HPLC retention time (min.):2.96; MS:256, 254 (M+H)$^+$.

EXAMPLE 3(68)

3-(Dimethylamino)-N-(2,5-dimethylphenyl)azetidine-1-carboxamide

HPLC retention time (min.):2.85; MS:248 (M+H)$^+$.

EXAMPLE 3(69)

N-(4-Chlorophenyl)-3-(dimethylamino)azetidine-1-carboxamide

HPLC retention time (min.):2.94; MS:256, 254 (M+H)$^+$.

EXAMPLE 3(70)

N-Benzyl-3-(dimethylamino)azetidine-1-carboxamide

HPLC retention time (min.):3.01(condition B); MS:234 (M+H)$^+$.

EXAMPLE 3(71)

3-(Dimethylamino)-N-(1-naphthyl)azetidine-1-carboxamide

HPLC retention time (min.):2.91; MS:539 (2M+H)$^+$, 27.0 (M+H)$^+$.

EXAMPLE 3(72)

3-(Dimethylamino)-N-(2-naphthyl)azetidine-1-carboxamide

HPLC retention time (min.):3.06; MS:539 (2M+H)$^+$, 270 (M+H)$^+$.

EXAMPLE 3(73)

3-(Dimethylamino)-N-[1-(l-naphthyl)ethyl]azetidine-1-carboxamide

HPLC retention time (min.):3.10; MS:595 (2M+H)$^+$, 298 (M+H)$^+$, 144.

EXAMPLE 3(74)

3-(Dimethylamino)-N-(3,4-dimethylphenyl)azetidine-1-carboxamide

HPLC retention time (min.):2.96; MS:495 (2M+H)$^+$, 248 (M+H)$^+$.

EXAMPLE 3(75)

3-(Dimethylamino)-N-(4-methylphenyl)azetidine-1-carboxamide

HPLC retention time (min.):2.83; MS:234 (M+H)$^+$.

EXAMPLE 3(76)

N-Cyclohexyl-3-(dimethylamino)azetidine-1-carboxamide

HPLC retention time (min.):2.67; MS:226 (M+H)$^+$.

EXAMPLE 3(77)

3-(Dimethylamino)-N-(2,6-dimethylphenyl)azetidine-1-carboxamide

HPLC retention time (min.):3.05(condition B); MS:495 (2M+H)$^+$, 248 (M+H)$^+$.

EXAMPLE 3(78)

3-(Dimethylamino)-N-(2-ethoxyphenyl)azetidine-1-carboxamide

HPLC retention time (min.):2.89; MS:264 (M+H)$^+$.

EXAMPLE 3(79)

3-(Dimethylamino)-N-(4-ethoxyphenyl)azetidine-1-carboxamide

HPLC retention time (min.):2.86; MS:264 (M+H)$^+$.

EXAMPLE 3(80)

3-(Dimethylamino)-N-(2-phenylethyl)azetidine-1-carboxamide

HPLC retention time (min.):2.83; MS:248 (M+H)$^+$.

EXAMPLE 3(81)

3-(Dimethylamino)-N-[3-(trifluoromethyl)phenyl]azetidine-1-carboxamide

HPLC retention time (min.):3.07; MS:575 (2M+H)$^+$, 288 (M+H)$^+$.

EXAMPLE 3(82)

N-Cyclopentyl-3-(dimethylamino)azetidine-1-carboxamide

HPLC retention time (min.):2.93(condition B); MS:212 (M+H)$^+$.

EXAMPLE 3(83)

3-(Dimethylamino)-N-(2,4-dimethylphenyl)azetidine-1-carboxamide

HPLC retention time (min.):2.86; MS:248 (M+H)$^+$.

EXAMPLE 3(84)

N-(3,5-Dichlorophenyl)-3-(dimethylamino)azetidine-1-carboxamide

HPLC retention time (min.):3.15; MS:577, 575 (2M+H)$^+$, 290, 288 (M+H)$^+$.

EXAMPLE 3(85)

N-[3,5-Bis(trifluoromethyl)phenyl]-3-(dimethylamino)azetidine-1-carboxamide

HPLC retention time (min.):3.30; MS:356 (M+H)$^+$.

EXAMPLE 3(86)

3-(Dimethylamino)-N-(3-phenoxyphenyl)azetidine-1-carboxamide

HPLC retention time (min.):3.21; MS:623 (2M+H)$^+$, 312 (M+H)$^+$.

EXAMPLE 3(87)

N-(3,5-Difluorophenyl)-3-(dimethylamino)azetidine-1-carboxamide

HPLC retention time (min.):2.93; MS:256 (M+H)$^+$.

EXAMPLE 3(88)

3-(Dimethylamino)-N-(4-methoxyphenyl)azetidine-1-carboxamide

HPLC retention time (min.):3.00(condition B); MS:499 (2M+H)$^+$, 250 (M+H)$^+$.

EXAMPLE 3(89)

3-(Dimethylamino)-N-(3,5-dimethylphenyl)azetidine-1-carboxamide

HPLC retention time (min.):3.00; MS:495 (2M+H)$^+$, 248 (M+H)$^+$.

EXAMPLE 3(90)

3-(Dimethylamino)-N-(3-fluorophenyl)azetidine-1-carboxamide

HPLC retention time (min.):2.72; MS:238 (M+H)$^+$.

EXAMPLE 3(91)

Methyl 3-({[3-(dimethylamino)azetidin-1-yl]carbonyl}amino)benzoate

HPLC retention time (min.):2.87; MS:555 (2M+H)$^+$, 278 (M+H)$^+$.

EXAMPLE 3(92)

3-(Dimethylamino)-N-[3-(methylsulfanyl)phenyl]azetidine-1-carboxamide

HPLC retention time (min.):2.96; MS:531 (2M+H)$^+$, 266 (M+H)$^+$.

EXAMPLE 3(93)

3-(Diethylamino)-N-propylazetidine-1-carboxamide

HPLC retention time (min.):3.00(condition B); MS:214 (M+H)$^+$.

EXAMPLE 3(94)

Ethyl N-{[3-(diethylamino)azetidin-1-yl]carbonyl}glycinate

HPLC retention time (min.):2.93(condition B); MS:258 (M+H)$^+$.

EXAMPLE 3(95)

3-(Diethylamino)-N-hexylazetidine-1-carboxamide

HPLC retention time (min.):3.05; MS:256 (M+H)$^+$.

EXAMPLE 3(96)

3-(Diethylamino)-N-(4-fluorophenyl)azetidine-1-carboxamide

HPLC retention time (min.):2.78; MS:266 (M+H)$^+$.

EXAMPLE 3(97)

3-(Diethylamino)-N-(3-methylphenyl)azetidine-1-carboxamide

HPLC retention time (min.):2.93; MS:523 (2M+H)$^+$, 262 (M+H)$^+$.

EXAMPLE 3(98)

3-(Diethylamino)-N-(2-thien-2-ylethyl)azetidine-1-carboxamide

HPLC retention time (min.):2.83; MS:282 (M+H)$^+$.

EXAMPLE 3(99)

3-(Diethylamino)-N-(4-isopropylphenyl)azetidine-1-carboxamide

HPLC retention time (min.):3.18; MS:579 (2M+H)$^+$, 290 (M+H)$^+$.

EXAMPLE 3(100)

N-(3-Chlorophenyl)-3-(diethylamino)azetidine-1-carboxamide

HPLC retention time (min.):3.01; MS:563 (2M+H)$^+$, 284, 282 (M+H)$^+$.

EXAMPLE 3(101)

3-(Diethylamino)-N-(2,5-dimethylphenyl)azetidine-1-carboxamide

HPLC retention time (min.):2.94; MS:551 (2M+H)$^+$, 276 (M+H)$^+$.

EXAMPLE 3(102)

N-(4-Chlorophenyl)-3-(diethylamino)azetidine-1-carboxamide

HPLC retention time (min.):3.02; MS:284, 282 (M+H)$^+$.

EXAMPLE 3(103)

N-Benzyl-3-(diethylamino)azetidine-1-carboxamide

HPLC retention time (min.):2.73; MS:262 (M+H)$^+$.

EXAMPLE 3(104)

3-(Diethylamino)-N-(1-naphthyl)azetidine-1-carboxamide

HPLC retention time (min.):2.98; MS:595 (2M+H)$^+$, 298 (M+H)$^+$.

EXAMPLE 3(105)

3-(Diethylamino)-N-(2-naphthyl)azetidine-1-carboxamide

HPLC retention time (min.):3.11; MS:595 (2M+H)$^+$, 298 (M+H)$^+$.

EXAMPLE 3(106)

3-(Diethylamino)-N-[1-(1-naphthyl)ethyl]azetidine-1-carboxamide

HPLC retention time (min.):3.15; MS:651 (2M+H)$^+$, 326 (M+H)$^+$, 172.

EXAMPLE 3(107)

3-(Diethylamino)-N-(3,4-dimethylphenyl)azetidine-1-carboxamide

HPLC retention time (min.):3.03; MS:551 (2M+H)$^+$, 276 (M+H)$^+$.

EXAMPLE 3(108)

3-(Diethylamino)-N-(4-methylphenyl)azetidine-1-carboxamide

HPLC retention time (min.):2.91; MS:262 (M+H)$^+$.

EXAMPLE 3(109)

N-Cyclohexyl-3-(diethylamino)azetidine-1-carboxamide

HPLC retention time (min.):2.82; MS:254 (M+H)$^+$.

EXAMPLE 3(110)

3-(Diethylamino)-N-(2,6-dimethylphenyl)azetidine-1-carboxamide

HPLC retention time (min.):2.78; MS:276 (M+H)$^+$.

EXAMPLE 3(111)

3-(Diethylamino)-N-(2-ethoxyphenyl)azetidine-1-carboxamide

HPLC retention time (min.):2.97; MS:583 (2M+H)$^+$, 292 (M+H)$^+$.

EXAMPLE 3(112)

3-(Diethylamino)-N-(2-ethylphenyl)azetidine-1-carboxamide

HPLC retention time (min.):2.90; MS:551 (2M+H)$^+$, 276 (M+H)$^+$.

EXAMPLE 3(113)

3-(Diethylamino)-N-(4-ethoxyphenyl)azetidine-1-carboxamide

HPLC retention time (min.):2.93; MS:583 (2M+H)$^+$, 292 (M+H)$^+$.

EXAMPLE 3(114)

3-(Diethylamino)-N-(2-phenylethyl)azetidine-1-carboxamide

HPLC retention time (min.):2.92; MS:276 (M+H)$^+$.

EXAMPLE 3(115)

3-(Diethylamino)-N-phenylazetidine-1-carboxamide

HPLC retention time (min.):3.23(condition B); MS:495 (2M+H)$^+$, 248 (M+H)$^+$.

EXAMPLE 3(116)

N-(2-Chlorophenyl)-3-(diethylamino)azetidine-1-carboxamide

HPLC retention time (min.):2.81; MS:282 (M+H)$^+$.

EXAMPLE 3(117)

3-(Diethylamino)-N-(2-fluorophenyl)azetidine-1-carboxamide

HPLC retention time (min.):3.24(condition B); MS:266 (M+H)$^+$.

EXAMPLE 3(118)

3-(Diethylamino)-N-[3-(trifluoromethyl)phenyl]azetidine-1-carboxamide

HPLC retention time (min.):3.13; MS:316 (M+H)$^+$.

EXAMPLE 3(119)

N-Cyclopentyl-3-(diethylamino)azetidine-1-carboxamide

HPLC retention time (min.):3.14(condition B); MS:240 (M+H)$^+$.

EXAMPLE 3(120)

3-(Diethylamino)-N-(2,4-dimethylphenyl)azetidine-1-carboxamide

HPLC retention time (min.):2.93; MS:551 (2M+H)$^+$, 276 (M+H)$^+$.

EXAMPLE 3(121)

N-(3,5-Dichlorophenyl)-3-(diethylamino)azetidine-1-carboxamide

HPLC retention time (min.):3.21; MS:633, 631 (2M+H)$^+$, 318, 316 (M+H)$^+$.

EXAMPLE 3(122)

N-[3,5-Bis(trifluoromethyl)phenyl]-3-(diethylamino)azetidine-1-carboxamide

HPLC retention time (min.):3.38; MS:384 (M+H)$^+$.

EXAMPLE 3(123)

3-(Diethylamino)-N-(3-phenoxyphenyl)azetidine-1-carboxamide

HPLC retention time (min.):3.26; MS:679 (2M+H)$^+$, 340 (M+H)$^+$.

EXAMPLE 3(124)

3-(Diethylamino)-N-(3,5-difluorophenyl)azetidine-1-carboxamide

HPLC retention time (min.):3.00; MS:284 (M+H)$^+$.

EXAMPLE 3(125)

3-(Diethylamino)-N-(4-methoxyphenyl)azetidine-1-carboxamide

HPLC retention time (min.):2.74; MS:278 (M+H)$^+$.

EXAMPLE 3(126)

3-(Diethylamino)-N-(3,5-dimethylphenyl)azetidine-1-carboxamide

HPLC retention time (min.):3.05; MS:551 (2M+H)$^+$, 276 (M+H)$^+$.

EXAMPLE 3(127)

3-(Diethylamino)-N-(3-fluorophenyl)azetidine-1-carboxamide

HPLC retention time (min.):2.87; MS:266 (M+H)$^+$.

EXAMPLE 3(128)

Methyl 3-({[3-(diethylamino)azetidin-1-yl]carbonyl}amino)benzoate

HPLC retention time (min.):2.93; MS:611 (2M+H)$^+$, 306 (M+H)$^+$.

EXAMPLE 3(129)

3-(Diethylamino)-N-[3-(methylsulfanyl)phenyl]azetidine-1-carboxamide

HPLC retention time (min.):3.01; MS:587 (2M+H)$^+$, 294 (M+H)$^+$.

EXAMPLE 3(130)

3-(Diethylamino)-N-(2-methylphenyl)azetidine-1-carboxamide

HPLC retention time (min.):2.65; MS:262 (M+H)$^+$.

EXAMPLE 3(131)

3-(Diisopropylamino)-N-propylazetidine-1-carboxamide

HPLC retention time (min.):3.37(condition B); MS:242 (M+H)$^+$.

EXAMPLE 3(132)

Ethyl N-{[3-(diisopropylamino)azetidin-1-yl]carbonyl}glycinate

HPLC retention time (min.):3.31(condition B); MS:286 (M+H)$^+$.

EXAMPLE 3(133)

3-(Diisopropylamino)-N-hexylazetidine-1-carboxamide

HPLC retention time (min.):3.11; MS:284 (M+H)$^+$.

EXAMPLE 3(134)

3-(Diisopropylamino)-N-(4-fluorophenyl)azetidine-1-carboxamide

HPLC retention time (min.):2.93; MS:294 (M+H)$^+$.

EXAMPLE 3(135)

3-(Diisopropylamino)-N-(3-methylphenyl)azetidine-1-carboxamide

HPLC retention time (min.):3.01; MS:290 (M+H)$^+$.

EXAMPLE 3(136)

3-(Diisopropylamino)-N-(2-thien-2-ylethyl)azetidine-1-carboxamide

HPLC retention time (min.):2.95; MS:310 (M+H)$^+$.

EXAMPLE 3(137)

3-(Diisopropylamino)-N-(4-isopropylphenyl)azetidine-1-carboxamide

HPLC retention time (min.):3.24; MS:635 (2M+H)$^+$, 318 (M+H)$^+$.

EXAMPLE 3(138)

N-(3-Chlorophenyl)-3-(diisopropylamino)azetidine-1-carboxamide

HPLC retention time (min.):3.08; MS:312, 310 (M+H)$^+$.

EXAMPLE 3(139)

3-(Diisopropylamino)-N-(2,5-dimethylphenyl)azetidine-1-carboxamide

HPLC retention time (min.):3.02; MS:304 (M+H)$^+$.

EXAMPLE 3(140)

N-(4-Chlorophenyl)-3-(diisopropylamino)azetidine-1-carboxamide

HPLC retention time (min.):3.09; MS:312, 310 (M+H)$^+$.

EXAMPLE 3(141)

N-Benzyl-3-(diisopropylamino)azetidine-1-carboxamide

HPLC retention time (min.):2.89; MS:290 (M+H)$^+$.

EXAMPLE 3(142)

3-(Diisopropylamino)-N-(1-naphthyl)azetidine-1-carboxamide

HPLC retention time (min.):3.06; MS:651 (2M+H)$^+$, 326 (M+H)$^+$.

EXAMPLE 3(143)

3-(Diisopropylamino)-N-(2-naphthyl)azetidine-1-carboxamide

HPLC retention time (min.):3.16; MS:651 (2M+H)$^+$, 326 (M+H)$^+$.

EXAMPLE 3(144)

3-(Diisopropylamino)-N-[1-(1-naphthyl)ethyl]azetidine-1-carboxamide

HPLC retention time (min.):3.22; MS:354 (M+H)$^+$.

EXAMPLE 3(145)

3-(Diisopropylamino)-N-(3,4-dimethylphenyl)azetidine-1-carboxamide

HPLC retention time (min.):3.10; MS:607 (2M+H)$^+$, 304 (M+H)$^+$.

EXAMPLE 3(146)

3-(Diisopropylamino)-N-(4-methylphenyl)azetidine-1-carboxamide

HPLC retention time (min.):3.02; MS:579 (2M+H)$^+$, 290 (M+H)$^+$.

EXAMPLE 3(147)

N-Cyclohexyl-3-(diisopropylamino)azetidine-1-carboxamide

HPLC retention time (min.):2.94; MS:282 (M+H)$^+$.

EXAMPLE 3(148)

3-(Diisopropylamino)-N-(2,6-dimethylphenyl)azetidine-1-carboxamide

HPLC retention time (min.):2.91; MS:304 (M+H)$^+$.

EXAMPLE 3(149)

3-(Diisopropylamino)-N-(2-ethoxyphenyl)azetidine-1-carboxamide

HPLC retention time (min.):3.04; MS:320 (M+H)$^+$.

EXAMPLE 3(150)

3-(Diisopropylamino)-N-(2-ethylphenyl)azetidine-1-carboxamide

HPLC retention time (min.):2.98; MS:607 (2M+H)$^+$, 304 (M+H)$^+$.

EXAMPLE 3(151)

3-(Diisopropylamino)-N-(4-ethoxyphenyl)azetidine-1-carboxamide

HPLC retention time (min.):3.03; MS:639 (2M+H)$^+$, 320 (M+H)$^+$.

EXAMPLE 3(152)

3-(Diisopropylamino)-N-(2-phenylethyl)azetidine-1-carboxamide

HPLC retention time (min.):3.01; MS:304 (M+H)$^+$.

EXAMPLE 3(153)

3-(Diisopropylamino)-N-phenylazetidine-1-carboxamide

HPLC retention time (min.):2.86; MS:276 (M+H)$^+$.

EXAMPLE 3(154)

N-(2-Chlorophenyl)-3-(diisopropylamino)azetidine-1-carboxamide

HPLC retention time (min.):2.94; MS:312, 310 (M+H)$^+$.

EXAMPLE 3(155)

3-(Diisopropylamino)-N-(2-fluorophenyl)azetidine-1-carboxamide

HPLC retention time (min.):2.81; MS:294 (M+H)$^+$.

EXAMPLE 3(156)

3-(Diisopropylamino)-N-[3-(trifluoromethyl)phenyl]azetidine-1-carboxamide

HPLC retention time (min.):3.32; MS:344 (M+H)$^+$.

EXAMPLE 3(157)

N-Cyclopentyl-3-(diisopropylamino)azetidine-1-carboxamide

HPLC retention time (min.):2.79; MS:268 (M+H)$^+$.

EXAMPLE 3(158)

3-(Diisopropylamino)-N-(2,4-dimethylphenyl)azetidine-1-carboxamide

HPLC retention time (min.):3.03; MS:607 (2M+H)$^+$, 304 (M+H)$^+$.

EXAMPLE 3(159)

N-(3,5-Dichlorophenyl)-3-(diisopropylamino)azetidine-1-carboxamide

HPLC retention time (min.):3.27; MS:346, 344 (M+H)$^+$.

EXAMPLE 3(160)

N-[3,5-Bis(trifluoromethyl)phenyl]-3-(diisopropylamino)azetidine-1-carboxamide

HPLC retention time (min.):3.43; MS:412 (M+H)$^+$.

EXAMPLE 3(161)

3-(Diisopropylamino)-N-(3-phenoxyphenyl)azetidine-1-carboxamide

HPLC retention time (min.):3.32; MS:735 (2M+H)$^+$, 368 (M+H)$^+$.

EXAMPLE 3(162)

N-(3,5-Difluorophenyl)-3-(diisopropylamino)azetidine-1-carboxamide

HPLC retention time (min.):3.07; MS:312 (M+H)$^+$.

EXAMPLE 3(163)

3-(Diisopropylamino)-N-(4-methoxyphenyl)azetidine-1-carboxamide

HPLC retention time (min.):2.88; MS:611 (2M+H)$^+$, 306 (M+H)$^+$.

EXAMPLE 3(164)

3-(Diisopropylamino)-N-(3,5-dimethylphenyl)azetidine-1-carboxamide

HPLC retention time (min.):3.13; MS:607 (2M+H)$^+$, 304 (M+H)$^+$.

EXAMPLE 3(165)

3-(Diisopropylamino)-N-(3-fluorophenyl)azetidine-1-carboxamide

HPLC retention time (min.):2.99; MS:294 (M+H)$^+$.

EXAMPLE 3(166)

Methyl 3-({[3-(diisopropylamino)azetidin-1-yl]carbonyl}amino)benzoate

HPLC retention time (min.):3.00; MS:667 (2M+H)$^+$, 334 (M+H)$^+$.

EXAMPLE 3(167)

3-(Diisopropylamino)-N-[3-(methylsulfanyl)phenyl]azetidine-1-carboxamide

HPLC retention time (min.):3.09; MS:643 (2M+H)$^+$, 322 (M+H)$^+$.

EXAMPLE 3(168)

3-(Diisopropylamino)-N-(2-methylphenyl)azetidine-1-carboxamide

HPLC retention time (min.):2.88; MS:290 (M+H)$^+$.

EXAMPLE 3(169)

3-(Dipropylamino)-N-propylazetidine-1-carboxamide

HPLC retention time (min.):3.36(condition B); MS:242 (M+H)$^+$.

EXAMPLE 3(170)

Ethyl N-{[3-(dipropylamino)azetidin-1-yl]carbonyl}glycinate

HPLC retention time (min.):3.29(condition B); MS:286 (M+H)$^+$.

EXAMPLE 3(171)

3-(Dipropylamino)-N-hexylazetidine-1-carboxamide

HPLC retention time (min.):3.17; MS:284 (M+H)$^+$.

EXAMPLE 3(172)

3-(Dipropylamino)-N-(4-fluorophenyl)azetidine-1-carboxamide

HPLC retention time (min.):3.00; MS:294 (M+H)$^+$.

EXAMPLE 3(173)

3-(Dipropylamino)-N-(3-methylphenyl)azetidine-1-carboxamide

HPLC retention time (min.):3.07; MS:579 (2M+H)$^+$, 2.90 (M+H)$^+$.

EXAMPLE 3(174)

3-(Dipropylamino)-N-(2-thien-2-ylethyl)azetidine-1-carboxamide

HPLC retention time (min.):3.01; MS:310 (M+H)$^+$.

EXAMPLE 3(175)

3-(Dipropylamino)-N-(4-isopropylphenyl)azetidine-1-carboxamide

HPLC retention time (min.):3.29; MS:635 (2M+H)$^+$, 318 (M+H)$^+$.

EXAMPLE 3(176)

N-(3-Chlorophenyl)-3-(dipropylamino)azetidine-1-carboxamide

HPLC retention time (min.): 3.15; MS: 312, 310 (M+H)$^+$.

EXAMPLE 3(177)

N-(2,5-Dimethylphenyl)-3-(dipropylamino)azetidine-1-carboxamide

HPLC retention time (min.): 3.08; MS: 607 (2M+H)$^+$, 304 (M+H)$^+$.

EXAMPLE 3(178)

N-(4-Chlorophenyl)-3-(dipropylamino)azetidine-1-carboxamide

HPLC retention time (min.): 3.14; MS: 312, 310 (M+H)$^+$.

EXAMPLE 3(179)

N-Benzyl-3-(dipropylamino)azetidine-1-carboxamide

HPLC retention time (min.): 2.96; MS: 290 (M+H)$^+$.

EXAMPLE 3(180)

3-(Dipropylamino)-N-(1-naphthyl)azetidine-1-carboxamide

HPLC retention time (min.): 3.11; MS: 651 (2M+H)$^+$, 326 (M+H)$^+$.

EXAMPLE 3(181)

3-(Dipropylamino)-N-(2-naphthyl)azetidine-1-carboxamide

HPLC retention time (min.): 3.21; MS: 651 (2M+H)$^+$, 326 (M+H)$^+$.

EXAMPLE 3(182)

3-(Dipropylamino)-N-[1-(1-naphthyl)ethyl]azetidine-1-carboxamide

HPLC retention time (min.): 3.26; MS: 707 (2M+H)$^+$, 354 (M+H)$^+$.

EXAMPLE 3(183)

N-(3,4-Dimethylphenyl)-3-(dipropylamino)azetidine-1-carboxamide

HPLC retention time (min.): 3.15; MS: 607 (2M+H)$^+$, 304 (M+H)$^+$.

EXAMPLE 3(184)

3-(Dipropylamino)-N-(4-methylphenyl)azetidine-1-carboxamide

HPLC retention time (min.): 3.07; MS: 579 (2M+H)$^+$, 290 (M+H)$^+$.

EXAMPLE 3(185)

N-Cyclohexyl-3-(dipropylamino)azetidine-1-carboxamide

HPLC retention time (min.): 3.00; MS: 282 (M+H)$^+$.

EXAMPLE 3(186)

N-(2,6-Dimethylphenyl)-3-(dipropylamino)azetidine-1-carboxamide

HPLC retention time (min.): 2.98; MS: 607 (2M+H)$^+$, 304 (M+H)$^+$.

EXAMPLE 3(187)

3-(Dipropylamino)-N-(2-ethoxyphenyl)azetidine-1-carboxamide

HPLC retention time (min.): 3.11; MS: 320 (M+H)+.

EXAMPLE 3(188)

3-(Dipropylamino)-N-(2-ethylphenyl)azetidine-1-carboxamide

HPLC retention time (min.): 3.06; MS: 607 (2M+H)+, 304 (M+H)+.

EXAMPLE 3(189)

3-(Dipropylamino)-N-(4-ethoxyphenyl)azetidine-1-carboxamide

HPLC retention time (min.): 3.06; MS: 639 (2M+H)+, 320 (M+H)+.

EXAMPLE 3(190)

3-(Dipropylamino)-N-(2-phenylethyl)azetidine-1-carboxamide

HPLC retention time (min.): 3.06; MS: 304 (M+H)+.

EXAMPLE 3(191)

3-(Dipropylamino)-N-phenylazetidine-1-carboxamide

HPLC retention time (min.): 2.95; MS: 276 (M+H)+.

EXAMPLE 3(192)

N-(2-Chlorophenyl)-3-(dipropylamino)azetidine-1-carboxamide

HPLC retention time (min.): 3.02; MS: 312, 310 (M+H)+.

EXAMPLE 3(193)

3-(Dipropylamino)-N-(2-fluorophenyl)azetidine-1-carboxamide

HPLC retention time (min.): 2.91; MS: 294 (M+H)+.

EXAMPLE 3(194)

3-(Dipropylamino)-N-[3-(trifluoromethyl)phenyl]azetidine-1-carboxamide

HPLC retention time (min.): 3.26; MS: 344 (M+H)+.

EXAMPLE 3(195)

N-Cyclopentyl-3-(dipropylamino)azetidine-1-carboxamide

HPLC retention time (min.): 2.88; MS: 268 (M+H)+.

EXAMPLE 3(196)

N-(2,4-Dimethylphenyl)-3-(dipropylamino)azetidine-1-carboxamide

HPLC retention time (min.): 3.09; MS: 607 (2M+H)+, 304 (M+H)+.

EXAMPLE 3(197)

N-(3,5-Dichlorophenyl)-3-(dipropylamino)azetidine-1-carboxamide

HPLC retention time (min.): 3.33; MS: 346, 344 (M+H)+.

EXAMPLE 3(198)

N-[3,5-Bis(trifluoromethyl)phenyl]-3-(dipropylamino)azetidine-1-carboxamide

HPLC retention time (min.): 3.47; MS: 412 (M+H)+.

EXAMPLE 3(199)

3-(Dipropylamino)-N-(3-phenoxyphenyl)azetidine-1-carboxamide

HPLC retention time (min.): 3.37; MS: 735 (2M+H)+, 368 (M+H)+.

EXAMPLE 3(200)

N-(3,5-Difluorophenyl)-3-(dipropylamino)azetidine-1-carboxamide

HPLC retention time (min.): 3.15; MS: 312 (M+H)+.

EXAMPLE 3(201)

3-(Dipropylamino)-N-(4-methoxyphenyl)azetidine-1-carboxamide

HPLC retention time (min.): 2.96; MS: 611 (2M+H)+, 306 (M+H)+.

EXAMPLE 3(202)

N-(3,5-Dimethylphenyl)-3-(dipropylamino)azetidine-1-carboxamide

HPLC retention time (min.): 3.18; MS: 607 (2M+H)+, 304 (M+H)+.

EXAMPLE 3(203)

3-(Dipropylamino)-N-(3-fluorophenyl)azetidine-1-carboxamide

HPLC retention time (min.): 3.05; MS: 294 (M+H)+.

EXAMPLE 3(204)

Methyl 3-({[3-(dipropylamino)azetidin-1-yl]carbonyl}amino)benzoate

HPLC retention time (min.): 3.04; MS: 667 (2M+H)+, 334 (M+H)+.

EXAMPLE 3(205)

3-(Dipropylamino)-N-[3-(methylsulfanyl)phenyl]azetidine-1-carboxamide

HPLC retention time (min.): 3.14; MS: 643 (2M+H)+, 322 (M+H)+.

EXAMPLE 3(206)

3-(Dipropylamino)-N-(2-methylphenyl)azetidine-1-carboxamide

HPLC retention time (min.): 2.95; MS: 579 (2M+H)$^+$, 290 (M+H)$^+$.

EXAMPLE 3(207)

3-[Bis(2-hydroxyethyl)amino]-N-hexylazetidine-1-carboxamide

HPLC retention time (min.): 2.97; MS: 575 (2M+H)$^+$, 288 (M+H)$^+$.

EXAMPLE 3(208)

3-[Bis(2-hydroxyethyl)amino]-N-(4-fluorophenyl)azetidine-1-carboxamide

HPLC retention time (min.): 2.91(condition B); MS: 595 (2M+H)$^+$, 298 (M+H)$^+$.

EXAMPLE 3(209)

3-[Bis(2-hydroxyethyl)amino]-N-(3-methylphenyl)azetidine-1-carboxamide

HPLC retention time (min.): 2.83; MS: 587 (2M+H)$^+$, 294 (M+H)$^+$.

EXAMPLE 3(210)

3-[Bis(2-hydroxyethyl)amino]-N-(4-isopropylphenyl)azetidine-1-carboxamide

HPLC retention time (min.): 3.10; MS: 643 (2M+H)$^+$, 322 (M+H)$^+$.

EXAMPLE 3(211)

3-[Bis(2-hydroxyethyl)amino]-N-(3-chlorophenyl)azetidine-1-carboxamide

HPLC retention time (min.): 2.95; MS: 627 (2M+H)$^+$, 316, 314 (M+H)$^+$.

EXAMPLE 3(212)

3-[Bis(2-hydroxyethyl)amino]-N-(2,5-dimethylphenyl)azetidine-1-carboxamide

HPLC retention time (min.): 2.83; MS: 615 (2M+H)$^+$, 308 (M+H)$^+$.

EXAMPLE 3(213)

3-[Bis(2-hydroxyethyl)amino]-N-(4-chlorophenyl)azetidine-1-carboxamide

HPLC retention time (min.): 2.95; MS: 316, 314 (M+H)$^+$.

EXAMPLE 3(214)

3-[Bis(2-hydroxyethyl)amino]-N-(1-naphthyl)azetidine-1-carboxamide

HPLC retention time (min.): 2.90; MS: 659 (2M+H)$^+$, 330 (M+H)$^+$.

EXAMPLE 3(215)

3-[Bis(2-hydroxyethyl)amino]-N-(2-naphthyl)azetidine-1-carboxamide

HPLC retention time (min.): 3.03; MS: 659 (2M+H)$^+$, 330 (M+H)$^+$.

EXAMPLE 3(216)

3-[Bis(2-hydroxyethyl)amino]-N-[1-(1-naphthyl)ethyl]azetidine-1-carboxamide

HPLC retention time (min.): 3.07; MS: 715 (2M+H)$^+$, 358 (M+H)$^+$, 204.

EXAMPLE 3(217)

3-[Bis(2-hydroxyethyl)amino]-N-(3,4-dimethylphenyl)azetidine-1-carboxamide

HPLC retention time (min.): 2.96; MS: 615 (2M+H)$^+$, 308 (M+H)$^+$.

EXAMPLE 3(218)

3-[Bis(2-hydroxyethyl)amino]-N-(4-methylphenyl)azetidine-1-carboxamide

HPLC retention time (min.): 2.81; MS: 587 (2M+H)$^+$, 294 (M+H)$^+$.

EXAMPLE 3(219)

3-[Bis(2-hydroxyethyl)amino]-N-cyclohexylazetidine-1-carboxamide

HPLC retention time (min.): 2.92(condition B); MS: 571 (2M+H)$^+$, 286 (M+H)$^+$.

EXAMPLE 3(220)

3-[Bis(2-hydroxyethyl)amino]-N-(2,6-dimethylphenyl)azetidine-1-carboxamide

HPLC retention time (min.): 2.90(condition B); MS: 615 (2M+H)$^+$, 308 (M+H)$^+$.

EXAMPLE 3(221)

3-[Bis(2-hydroxyethyl)amino]-N-(2-ethoxyphenyl)azetidine-1-carboxamide

HPLC retention time (min.): 2.88; MS: 647 (2M+H)$^+$, 324 (M+H)$^+$.

EXAMPLE 3(222)

3-[Bis(2-hydroxyethyl)amino]-N-(2-ethylphenyl)azetidine-1-carboxamide

HPLC retention time (min.): 2.78; MS: 615 (2M+H)$^+$, 308 (M+H)$^+$.

EXAMPLE 3(223)

3-[Bis(2-hydroxyethyl)amino]-N-(4-ethoxyphenyl)azetidine-1-carboxamide

HPLC retention time (min.): 2.85; MS: 647 (2M+H)$^+$, 324 (M+H)$^+$.

EXAMPLE 3(224)

3-[Bis(2-hydroxyethyl)amino]-N-(2-phenylethyl)azetidine-1-carboxamide

HPLC retention time (min.): 2.83; MS: 615 (2M+H)$^+$, 308 (M+H)$^+$.

EXAMPLE 3(225)

3-[Bis(2-hydroxyethyl)amino]-N-phenylazetidine-1-carboxamide

HPLC retention time (min.): 2.87(condition B); MS: 559 (2M+H)$^+$, 280 (M+H)$^+$.

EXAMPLE 3(226)

3-[Bis(2-hydroxyethyl)amino]-N-(2-chlorophenyl)azetidine-1-carboxamide

HPLC retention time (min.): 2.97(condition B); MS: 627 (2M+H)$^+$, 316, 314 (M+H)$^+$.

EXAMPLE 3(227)

3-[Bis(2-hydroxyethyl)amino]-N-(2-fluorophenyl)azetidine-1-carboxamide

HPLC retention time (min.): 2.84(condition B); MS: 595 (2M+H)$^+$, 298 (M+H)$^+$.

EXAMPLE 3(228) 3-[Bis(2-hydroxyethyl)amino]-N-[3-(trifluoromethyl)phenyl]azetidine-1-carboxamide HPLC retention time (min.): 3.06; MS: 348 (M+H)$^+$.

EXAMPLE 3(229)

3-[Bis(2-hydroxyethyl)amino]-N-cyclopentylazetidine-1-carboxamide

HPLC retention time (min.): 2.80(condition B); MS: 543 (2M+H)$^+$, 272 (M+H)$^+$.

EXAMPLE 3(230)

3-[Bis(2-hydroxyethyl)amino]-N-(2,4-dimethylphenyl)azetidine-1-carboxamide

HPLC retention time (min.): 2.85; MS: 308 (M+H)$^+$.

EXAMPLE 3(231)

3-[Bis(2-hydroxyethyl)amino]-N-(3,5-dichlorophenyl)azetidine-1-carboxamide

HPLC retention time (min.): 3.13; MS: 697, 695 (2M+H)$^+$, 350, 348 (M+H)$^+$.

EXAMPLE 3(232)

3-[Bis(2-hydroxyethyl)amino]-N-[3,5-bis(trifluoromethyl)phenyl]azetidine-1-carboxamide HPLC retention time (min.): 3.28; MS: 831 (2M+H)$^+$, 416 (M+H)$^+$.

EXAMPLE 3(233)

3-[Bis(2-hydroxyethyl)amino]-N-(3-phenoxyphenyl)azetidine-1-carboxamide

HPLC retention time (min.): 3.18; MS: 743 (2M+H)$^+$, 372 (M+H)$^+$.

EXAMPLE 3(234)

3-[Bis(2-hydroxyethyl)amino]-N-(3,5-difluorophenyl)azetidine-1-carboxamide

HPLC retention time (min.): 2.92; MS: 631 (2M+H)$^+$, 316 (M+H)$^+$.

EXAMPLE 3(235)

3-[Bis(2-hydroxyethyl)amino]-N-(4-methoxyphenyl)azetidine-1-carboxamide

HPLC retention time (min.): 2.87(condition B); MS: 619 (2M+H)$^+$, 310 (M+H)$^+$.

EXAMPLE 3(236)

3-[Bis(2-hydroxyethyl)amino]-N-(3,5-dimethylphenyl)azetidine-1-carboxamide

HPLC retention time (min.): 2.98; MS: 615 (2M+H)$^+$, 308 (M+H)$^+$.

EXAMPLE 3(237)

3-[Bis(2-hydroxyethyl)amino]-N-(3-fluorophenyl)azetidine-1-carboxamide

HPLC retention time (min.): 2.71; MS: 595 (2M+H)$^+$, 298 (M+H)$^+$.

EXAMPLE 3(238)

Methyl 3-[({3-[bis(2-hydroxyethyl)amino]azetidin-1-yl}carbonyl)amino]benzoate

HPLC retention time (min.): 2.85; MS: 675 (2M+H)$^+$, 338 (M+H)$^+$.

EXAMPLE 3(239)

3-[Bis(2-hydroxyethyl)amino]-N-[3-(methylsulfanyl)phenyl]azetidine-1-carboxamide HPLC retention time (min.): 2.95; MS: 651 (2M+H)$^+$, 326 (M+H)$^+$.

EXAMPLE 3(240)

N-Ethyl-3-[methyl(phenyl)amino]azetidine-1-carboxamide

HPLC retention time (min.): 2.73; MS: 234 (M+H)$^+$, 146.

EXAMPLE 3(241)

3-[Methyl(phenyl)amino]-N-propylazetidine-1-carboxamide

HPLC retention time (min.): 2.95; MS: 248 (M+H)$^+$.

EXAMPLE 3(242)

Ethyl N-({3-[methyl(phenyl)amino]azetidin-1-yl}carbonyl)glycinate

HPLC retention time (min.): 2.91; MS: 292 (M+H)$^+$.

EXAMPLE 3(243)

N-Hexyl-3-[methyl(phenyl)amino]azetidine-1-carboxamide

HPLC retention time (min.): 3.46; MS: 290 (M+H)$^+$.

EXAMPLE 3(244)

N-(4-Fluorophenyl)-3-[methyl(phenyl)amino]azetidine-1-carboxamide

HPLC retention time (min.): 3.33; MS: 300 (M+H)$^+$.

EXAMPLE 3(245)

N-(3-Methylphenyl)-3-[methyl(phenyl)amino]azetidine-1-carboxamide

HPLC retention time (min.): 3.38; MS: 591 (2M+H)$^+$, 296 (M+H)$^+$.

EXAMPLE 3(246)

3-[Methyl(phenyl)amino]-N-(2-thien-2-ylethyl)azetidine-1-carboxamide

HPLC retention time (min.): 3.27; MS: 316 (M+H)$^+$.

EXAMPLE 3(247)

N-(4-Isopropylphenyl)-3-[methyl(phenyl)amino]azetidine-1-carboxamide

HPLC retention time (min.): 3.62; MS: 647 (2M+H)$^+$, 324 (M+H)$^+$.

EXAMPLE 3(248)

N-(3-Chlorophenyl)-3-[methyl(phenyl)amino]azetidine-1-carboxamide

HPLC retention time (min.): 3.52; MS: 318, 316 (M+H)$^+$.

EXAMPLE 3(249)

N-(2,5-Dimethylphenyl)-3-[methyl(phenyl)amino]azetidine-1-carboxamide

HPLC retention time (min.): 3.40; MS: 619 (2M+H)$^+$, 310 (M+H)$^+$.

EXAMPLE 3(250)

N-(4-Chlorophenyl)-3-[methyl(phenyl)amino]azetidine-1-carboxamide

HPLC retention time (min.): 3.49; MS: 318, 316 (M+H)$^+$.

EXAMPLE 3(251)

N-Benzyl-3-[methyl(phenyl)amino]azetidine-1-carboxamide

HPLC retention time (min.): 3.22; MS: 296 (M+H)$^+$.

EXAMPLE 3(252)

3-[Methyl(phenyl)amino]-N-(1-naphthyl)azetidine-1-carboxamide

HPLC retention time (min.): 3.43; MS: 663 (2M+H)$^+$, 332 (M+H)$^+$.

EXAMPLE 3(253)

3-[Methyl(phenyl)amino]-N-(2-naphthyl)azetidine-1-carboxamide

HPLC retention time (min.): 3.55; MS: 663 (2M+H)$^+$, 332 (M+H)$^+$.

EXAMPLE 3(254)

3-[Methyl(phenyl)amino]-N-[1-(1-naphthyl)ethyl]azetidine-1-carboxamide

HPLC retention time (min.): 3.56; MS: 719 (2M+H)$^+$, 360 (M+H)$^+$, 206.

EXAMPLE 3(255)

N-(3,4-Dimethylphenyl)-3-[methyl(phenyl)amino]azetidine-1-carboxamide

HPLC retention time (min.): 3.47; MS: 619 (2M+H)$^+$, 310 (M+H)$^+$.

EXAMPLE 3(256)

N-(4-Methylphenyl)-3-[methyl(phenyl)amino]azetidine-1-carboxamide

HPLC retention time (min.): 3.38; MS: 591 (2M+H)$^+$, 296 (M+H)$^+$.

EXAMPLE 3(257)

N-Cyclohexyl-3-[methyl(phenyl)amino]azetidine-1-carboxamide

HPLC retention time (min.): 3.27; MS: 288 (M+H)$^+$.

EXAMPLE 3(258)

N-(2,6-Dimethylphenyl)-3-[methyl(phenyl)amino]azetidine-1-carboxamide

HPLC retention time (min.): 3.30; MS: 619 (2M+H)$^+$, 310 (M+H)$^+$.

EXAMPLE 3(259)

N-(2-Ethoxyphenyl)-3-[methyl(phenyl)amino]azetidine-1-carboxamide

HPLC retention time (min.): 3.55; MS: 651 (2M+H)$^+$, 326 (M+H)$^+$.

EXAMPLE 3(260)

N-(2-Ethylphenyl)-3-[methyl(phenyl)amino]azetidine-1-carboxamide

HPLC retention time (min.): 3.39; MS: 619 (2M+H)$^+$, 310 (M+H)$^+$.

EXAMPLE 3(261)

N-(4-Ethoxyphenyl)-3-[methyl(phenyl)amino]azetidine-1-carboxamide

HPLC retention time (min.): 3.35; MS: 651 (2M+H)$^+$, 326 (M+H)$^+$.

EXAMPLE 3(262)

3-[Methyl(phenyl)amino]-N-(2-phenylethyl)azetidine-1-carboxamide

HPLC retention time (min.): 3.31; MS: 310 (M+H)$^+$.

EXAMPLE 3(263)

3-[Methyl(phenyl)amino]-N-phenylazetidine-1-carboxamide

HPLC retention time (min.): 3.25; MS: 563 (2M+H)$^+$, 282 (M+H)$^+$.

EXAMPLE 3(264)

N-(2-Chlorophenyl)-3-[methyl(phenyl)amino]azetidine-1-carboxamide

HPLC retention time (min.): 3.49; MS: 318, 316 (M+H)$^+$.

EXAMPLE 3(265)

N-(2-Fluorophenyl)-3-[methyl(phenyl)amino]azetidine-1-carboxamide

HPLC retention time (min.): 3.30; MS: 300 (M+H)$^+$.

EXAMPLE 3(266)

3-[Methyl(phenyl)amino]-N-[3-(trifluoromethyl)phenyl]azetidine-1-carboxamide

HPLC retention time (min.): 3.63; MS: 350 (M+H)$^+$.

EXAMPLE 3(267)

N-Cyclopentyl-3-[methyl(phenyl)amino]azetidine-1-carboxamide

HPLC retention time (min.): 3.15; MS: 274 (M+H)$^+$.

EXAMPLE 3(268)

N-(2,4-Dimethylphenyl)-3-[methyl(phenyl)amino]azetidine-1-carboxamide

HPLC retention time (min.): 3.39; MS: 619 (2M+H)$^+$, 310 (M+H)$^+$.

EXAMPLE 3(269)

N-(3,5-Dichlorophenyl)-3-[methyl(phenyl)amino]azetidine-1-carboxamide

HPLC retention time (min.): 3.78; MS: 352, 350 (M+H)$^+$.

EXAMPLE 3(270)

N-[3,5-Bis(trifluoromethyl)phenyl]-3-[methyl(phenyl)amino]azetidine-1-carboxamide HPLC retention time (min.): 3.94; MS: 418 (M+H)$^+$.

EXAMPLE 3(271)

3-[Methyl(phenyl)amino]-N-(3-phenoxyphenyl)azetidine-1-carboxamide

HPLC retention time (min.): 3.73; MS: 747 (2M+H)$^+$, 374 (M+H)$^+$.

EXAMPLE 3(272)

N-(3,5-Difluorophenyl)-3-[methyl(phenyl)amino]azetidine-1-carboxamide

HPLC retention time (min.): 3.53; MS: 318 (M+H)$^+$.

EXAMPLE 3(273)

N-(4-Methoxyphenyl)-3-[methyl(phenyl)amino]azetidine-1-carboxamide

HPLC retention time (min.): 3.23; MS: 623 (2M+H)$^+$, 312 (M+H)$^+$.

EXAMPLE 3(274)

N-(3,5-Dimethylphenyl)-3-[methyl(phenyl)amino]azetidine-1-carboxamide

HPLC retention time (min.): 3.49; MS: 619 (2M+H)$^+$, 310 (M+H)$^+$.

EXAMPLE 3(275)

N-(3-Fluorophenyl)-3-[methyl(phenyl)amino]azetidine-1-carboxamide

HPLC retention time (min.): 3.40; MS: 300 (M+H)$^+$.

EXAMPLE 3(276)

Methyl 3-[({3-[methyl(phenyl)amino]azetidin-1-yl}carbonyl)amino]benzoate

HPLC retention time (min.): 3.35; MS: 679 (2M+H)$^+$, 340 (M+H)$^+$.

EXAMPLE 3(277)

3-[Methyl(phenyl)amino]-N-[3-(methylsulfanyl)phenyl]azetidine-1-carboxamide

HPLC retention time (min.): 3.46; MS: 655 (2M+H)$^+$, 328 (M+H)$^+$.

EXAMPLE 3(278)

N-(2-Methylphenyl)-3-[methyl(phenyl)amino]azetidine-1-carboxamide

HPLC retention time (min.): 3.28; MS: 591 (2M+H)$^+$, 296 (M+H)$^+$.

EXAMPLE 3(279)

3-[Ethyl(phenyl)amino]-N-propylazetidine-1-carboxamide

HPLC retention time (min.): 2.87; MS: 262 (M+H)$^+$.

EXAMPLE 3(280)

Ethyl N-({3-[ethyl(phenyl)amino]azetidin-1-yl}carbonyl)glycinate

HPLC retention time (min.): 2.84; MS: 306 (M+H)$^+$.

EXAMPLE 3(281)

3-[Ethyl(phenyl)amino]-N-hexylazetidine-1-carboxamide

HPLC retention time (min.): 3.32; MS: 304 (M+H)$^+$.

EXAMPLE 3(282)

3-[Ethyl(phenyl)amino]-N-(4-fluorophenyl)azetidine-1-carboxamide

HPLC retention time (min.): 3.17; MS: 314 (M+H)$^+$.

EXAMPLE 3(283)

3-[Ethyl(phenyl)amino]-N-(3-methylphenyl)azetidine-1-carboxamide

HPLC retention time (min.): 3.24; MS: 619 (2M+H)$^+$, 310 (M+H)$^+$.

EXAMPLE 3(284)

3-[Ethyl(phenyl)amino]-N-(2-thien-2-ylethyl)azetidine-1-carboxamide

HPLC retention time (min.): 3.14; MS: 330 (M+H)$^+$.

EXAMPLE 3(285)

3-[Ethyl(phenyl)amino]-N-(4-isopropylphenyl)azetidine-1-carboxamide

HPLC retention time (min.): 3.47; MS: 675 (2M+H)$^+$, 338 (M+H)$^+$.

EXAMPLE 3(286)

N-(3-Chlorophenyl)-3-[ethyl(phenyl)amino]azetidine-1-carboxamide

HPLC retention time (min.): 3.34; MS: 332, 330 (M+H)$^+$.

EXAMPLE 3(287)

N-(2,5-Dimethylphenyl)-3-[ethyl(phenyl)amino]azetidine-1-carboxamide

HPLC retention time (min.): 3.25; MS: 647 (2M+H)$^+$, 324 (M+H)$^+$.

EXAMPLE 3(288)

N-(4-Chlorophenyl)-3-[ethyl(phenyl)amino]azetidine-1-carboxamide

HPLC retention time (min.): 3.32; MS: 332, 330 (M+H)$^+$.

EXAMPLE 3(289)

N-Benzyl-3-[ethyl(phenyl)amino]azetidine-1-carboxamide

HPLC retention time (min.): 3.13; MS: 310 (M+H)$^+$.

EXAMPLE 3(290)

3-[Ethyl(phenyl)amino]-N-(1-naphthyl)azetidine-1-carboxamide

HPLC retention time (min.): 3.28; MS: 691 (2M+H)$^+$, 346 (M+H)$^+$.

EXAMPLE 3(291)

3-[Ethyl(phenyl)amino]-N-(2-naphthyl)azetidine-1-carboxamide

HPLC retention time (min.): 3.39; MS: 691 (2M+H)$^+$, 346 (M+H)$^+$.

EXAMPLE 3(292)

3-[Ethyl(phenyl)amino]-N-[1-(1-naphthyl)ethyl]azetidine-1-carboxamide

HPLC retention time (min.): 3.41; MS: 747 (2M+H)$^+$, 374 (M+H)$^+$, 220.

EXAMPLE 3(293)

N-(3,4-Dimethylphenyl)-3-[ethyl(phenyl)amino]azetidine-1-carboxamide

HPLC retention time (min.): 3.31; MS: 647 (2M+H)$^+$, 324 (M+H)$^+$.

EXAMPLE 3(294)

3-[Ethyl(phenyl)amino]-N-(4-methylphenyl)azetidine-1-carboxamide

HPLC retention time (min.): 3.23; MS: 619 (2M+H)$^+$, 310 (M+H)$^+$.

EXAMPLE 3(295)

N-Cyclohexyl-3-[(ethyl(phenyl)amino]azetidine-1-carboxamide

HPLC retention time (min.): 3.15; MS: 302 (M+H)$^+$.

EXAMPLE 3(296)

N-(2,6-Dimethylphenyl)-3-[ethyl(phenyl)amino]azetidine-1-carboxamide

HPLC retention time (min.): 3.16; MS: 647 (2M+H)$^+$, 324 (M+H)$^+$.

EXAMPLE 3(297)

N-(2-Ethoxyphenyl)-3-[ethyl(phenyl)amino]azetidine-1-carboxamide

HPLC retention time (min.): 3.36; MS: 679 (2M+H)$^+$, 340 (M+H)$^+$.

EXAMPLE 3(298)

N-(2-Ethylphenyl)-3-[ethyl(phenyl)amino]azetidine-1-carboxamide

HPLC retention time (min.): 3.25; MS: 647 (2M+H)$^+$, 324 (M+H)$^+$.

EXAMPLE 3(299)

N-(4-Ethoxyphenyl)-3-[ethyl(phenyl)amino]azetidine-1-carboxamide

HPLC retention time (min.): 3.23; MS: 679 (2M+H)$^+$, 340 (M+H)$^+$.

EXAMPLE 3(300)

3-[Ethyl(phenyl)amino]-N-(2-phenylethyl)azetidine-1-carboxamide

HPLC retention time (min.): 3.19; MS: 324 (M+H)$^+$.

EXAMPLE 3(301)

3-[Ethyl(phenyl)amino]-N-phenylazetidine-1-carboxamide

HPLC retention time (min.): 3.12; MS: 296 (M+H)$^+$.

EXAMPLE 3(302)

N-(2-Chlorophenyl)-3-[ethyl(phenyl)amino]azetidine-1-carboxamide

HPLC retention time (min.): 3.30; MS: 332, 330 (M+H)$^+$.

EXAMPLE 3(303)

3-[Ethyl(phenyl)amino]-N-(2-fluorophenyl)azetidine-1-carboxamide

HPLC retention time (min.): 3.14; MS: 314 (M+H)$^+$.

EXAMPLE 3(304)

3-[Ethyl(phenyl)amino]-N-[3-(trifluoromethyl)phenyl]azetidine-1-carboxamide

HPLC retention time (min.): 3.46; MS: 364 (M+H)$^+$.

EXAMPLE 3(305)

N-Cyclopentyl-3-[ethyl(phenyl)amino]azetidine-1-carboxamide

HPLC retention time (min.): 3.06; MS: 288 (M+H)$^+$.

EXAMPLE 3(306)

N-(2,4-Dimethylphenyl)-3-[ethyl(phenyl)amino]azetidine-1-carboxamide

HPLC retention time (min.): 3.24; MS: 647 (2M+H)$^+$, 324 (M+H)$^+$.

EXAMPLE 3(307)

N-(3,5-Dichlorophenyl)-3-[ethyl(phenyl)aminol]azetidine-1-carboxamide

HPLC retention time (min.): 3.58; MS: 729, 727 (2M+H)$^+$, 366, 364 (M+H)$^+$.

EXAMPLE 3(308)

N-[3,5-Bis(trifluoromethyl)phenyl]-3-[ethyl(phenyl)amino]azetidine-1-carboxamide HPLC retention time (min.): 3.74; MS: 432 (M+H)$^+$.

EXAMPLE 3(309)

3-[Ethyl(phenyl)amino]-N-(3-phenoxyphenyl)azetidine-1-carboxamide

HPLC retention time (min.): 3.56; MS: 775 (2M+H)$^+$, 388 (M+H)$^+$.

EXAMPLE 3(310)

N-(3,5-Difluorophenyl)-3-[ethyl(phenyl)amino]azetidine-1-carboxamide

HPLC retention time (min.): 3.36; MS: 332 (M+H)$^+$.

EXAMPLE 3(311)

3-[Ethyl(phenyl)amino]-N-(4-methoxyphenyl)azetidine-1-carboxamide

HPLC retention time (min.): 3.11; MS: 651 (2M+H)$^+$, 326 (M+H)$^+$.

EXAMPLE 3(312)

N-(3,5-Dimethylphenyl)-3-[ethyl(phenyl)amino]azetidine-1-carboxamide

HPLC retention time (min.): 3.35; MS: 647 (2M+H)$^+$, 324 (M+H)$^+$.

EXAMPLE 3(313)

3-[Ethyl(phenyl)amino]-N-(3-fluorophenyl)azetidine-1-carboxamide

HPLC retention time (min.): 3.25; MS: 314 (M+H)+.

EXAMPLE 3(314)

Methyl 3-[({3-[ethyl(phenyl)amino]azetidin-1-yl}carbonyl)amino]benzoate

HPLC retention time (min.): 3.21; MS: 707 (2M+H)+, 354 (M+H)+.

EXAMPLE 3(315)

3-[Ethyl(phenyl)amino]-N-[3-(methylsulfanyl)phenyl]azetidine-1-carboxamide

HPLC retention time (min.): 3.32; MS: 683 (2M+H)+, 342 (M+H)+.

EXAMPLE 3(316)

3-[Ethyl(phenyl)amino]-N-(2-methylphenyl)azetidine-1-carboxamide

HPLC retention time (min.): 3.13; MS: 619 (2M+H)+, 310 (M+H)+.

EXAMPLE 3(317)

3-[Phenyl(propyl)amino]-N-propylazetidine-1-carboxamide

HPLC retention time (min.): 3.05; MS: 276 (M+H)+.

EXAMPLE 3(318)

Ethyl N-({3-[phenyl(propyl)amino]azetidin-1-yl}carbonyl)glycinate

HPLC retention time (min.): 3.02; MS: 320 (M+H)+.

EXAMPLE 3(319)

N-Hexyl-3-[phenyl(propyl)amino]azetidine-1-carboxamide

HPLC retention time (min.): 3.49; MS: 318 (M+H)+.

EXAMPLE 3(320)

N-(4-Fluorophenyl)-3-[phenyl(propyl)amino]azetidine-1-carboxamide

HPLC retention time (min.): 3.36; MS: 328 (M+H)+.

EXAMPLE 3(321)

N-(3-Methylphenyl)-3-[phenyl(propyl)amino]azetidine-1-carboxamide

HPLC retention time (min.): 3.41; MS: 324 (M+H)+.

EXAMPLE 3(322)

3-[Phenyl(propyl)amino]-N-(2-thien-2-ylethyl)azetidine-1-carboxamide

HPLC retention time (min.): 3.31; MS: 344 (M+H)+.

EXAMPLE 3(323)

N-(4-Isopropylphenyl)-3-[phenyl(propyl)amino]azetidine-1-carboxamide

HPLC retention time (min.): 3.63; MS: 703 (2M+H)+, 352 (M+H)+.

EXAMPLE 3(324)

N-(3-Chlorophenyl)-3-[phenyl(propyl)amino]azetidine-1-carboxamide

HPLC retention time (min.): 3.54; MS: 346, 344 (M+H)+.

EXAMPLE 3(325)

N-(2,5-Dimethylphenyl)-3-[phenyl(propyl)amino]azetidine-1-carboxamide

HPLC retention time (min.): 3.44; MS: 675 (2M+H)+, 338 (M+H)+.

EXAMPLE 3(326)

N-(4-Chlorophenyl)-3-[phenyl(propyl)amino]azetidine-1-carboxamide

HPLC retention time (min.): 3.52; MS: 346, 344 (M+H)+.

EXAMPLE 3(327)

N-Benzyl-3-[phenyl(propyl)amino]azetidine-1-carboxamide

HPLC retention time (min.): 3.27; MS: 324 (M+H)+.

EXAMPLE 3(328)

N-(1-Naphthyl)-3-[phenyl(propyl)amino]azetidine-1-carboxamide

HPLC retention time (min.): 3.45; MS: 719 (2M+H)+, 360 (M+H)+.

EXAMPLE 3(329)

N-(2-Naphthyl)-3-[phenyl(propyl)amino]azetidine-1-carboxamide

HPLC retention time (min.): 3.56; MS: 719 (2M+H)+, 360 (M+H)+.

EXAMPLE 3(330)

N-[1-(1-Naphthyl)ethyl]-3-[phenyl(propyl)amino]azetidine-1-carboxamide

HPLC retention time (min.): 3.56; MS: 775 (2M+H)+, 388 (M+H)+, 234.

EXAMPLE 3(331)

N-(3,4-Dimethylphenyl)-3-[phenyl(propyl)amino]azetidine-1-carboxamide

HPLC retention time (min.): 3.50; MS: 675 (2M+H)+, 338 (M+H)+.

EXAMPLE 3(332)

N-(4-Methylphenyl)-3-[phenyl(propyl)amino]azetidine-1-carboxamide

HPLC retention time (min.): 3.41; MS: 324 (M+H)$^+$.

EXAMPLE 3(333)

N-Cyclohexyl-3-[phenyl(propyl)amino]azetidine-1-carboxamide

HPLC retention time (min.): 3.31; MS: 316 (M+H)$^+$.

EXAMPLE 3(334)

N-(2,6-Dimethylphenyl)-3-[phenyl(propyl)amino]azetidine-1-carboxamide

HPLC retention time (min.): 3.34; MS: 675 (2M+H)$^+$, 338 (M+H)$^+$.

EXAMPLE 3(335)

N-(2-Ethoxyphenyl)-3-[phenyl(propyl)amino]azetidine-1-carboxamide

HPLC retention time (min.): 3.58; MS: 707 (2M+H)$^+$, 354 (M+H)$^+$.

EXAMPLE 3(336)

N-(2-Ethylphenyl)-3-[phenyl(propyl)amino]azetidine-1-carboxamide

HPLC retention time (min.): 3.42; MS: 675 (2M+H)$^+$, 338 (M+H)$^+$.

EXAMPLE 3(337)

N-(4-Ethoxyphenyl)-3-[phenyl(propyl)amino]azetidine-1-carboxamide

HPLC retention time (min.): 3.38; MS: 707 (2M+H)$^+$, 354 (M+H)$^+$.

EXAMPLE 3(338)

N-(2-Phenylethyl)-3-[phenyl(propyl)amino]azetidine-1-carboxamide

HPLC retention time (min.): 3.36; MS: 338 (M+H)$^+$.

EXAMPLE 3(339)

N-Phenyl-3-[phenyl(propyl)amino]azetidine-1-carboxamide

HPLC retention time (min.): 3.31; MS: 310 (M+H)$^+$.

EXAMPLE 3(340)

N-(2-Chlorophenyl)-3-[phenyl(propyl)amino]azetidine-1-carboxamide

HPLC retention time (min.): 3.53; MS: 346, 344 (M+H)$^+$.

EXAMPLE 3(341)

N-(2-Fluorophenyl)-3-[phenyl(propyl)amino]azetidine-1-carboxamide

HPLC retention time (min.): 3.34; MS: 328 (M+H)$^+$.

EXAMPLE 3(342)

3-[Phenyl(propyl)amino]-N-[3-(trifluoromethyl)phenyl]azetidine-1-carboxamide

HPLC retention time (min.): 3.65; MS: 378 (M+H)$^+$.

EXAMPLE 3(343)

N-Cyclopentyl-3-[phenyl(propyl)amino]azetidine-1-carboxamide

HPLC retention time (min.): 3.21; MS: 302 (M+H)$^+$.

EXAMPLE 3(344)

N-(2,4-Dimethylphenyl)-3-[phenyl(propyl)amino]azetidine-1-carboxamide

HPLC retention time (min.): 3.42; MS: 675 (2M+H)$^+$, 338 (M+H)$^+$.

EXAMPLE 3(345)

N-(3,5-Dichlorophenyl)-3-[phenyl(propyl)amino]azetidine-1-carboxamide

HPLC retention time (min.): 3.79; MS: 380, 378 (M+H)$^+$.

EXAMPLE 3(346)

N-[3,5-Bis(trifluoromethyl)phenyl]-3-[phenyl(propyl)amino]azetidine-1-carboxamide HPLC retention time (min.): 3.95; MS: 446 (M+H)$^+$.

EXAMPLE 3(347)

N-(3-Phenoxyphenyl)-3-[phenyl(propyl)amino]azetidine-1-carboxamide

HPLC retention time (min.): 3.73; MS: 803 (2M+H)$^+$, 402 (M+H)$^+$.

EXAMPLE 3(348)

N-(3,5-Difluorophenyl)-3-[phenyl(propyl)amino]azetidine-1-carboxamide

HPLC retention time (min.): 3.57; MS: 346 (M+H)$^+$.

EXAMPLE 3(349)

N-(4-Methoxyphenyl)-3-[phenyl(propyl)amino]azetidine-1-carboxamide

HPLC retention time (min.): 3.29; MS: 679 (2M+H)$^+$, 340 (M+H)$^+$.

EXAMPLE 3(350)

N-(3,5-Dimethylphenyl)-3-[phenyl(propyl)amino]
azetidine-1-carboxamide

HPLC retention time (min.): 3.52; MS: 675 (2M+H)$^+$, 338 (M+H)$^+$.

EXAMPLE 3(351)

N-(3-Fluorophenyl)-3-[phenyl(propyl)amino]azeti-
dine-1-carboxamide

HPLC retention time (min.): 3.43; MS: 328 (M+H)$^+$.

EXAMPLE 3(352)

Methyl 3-[({3-[phenyl(propyl)amino]azetidin-1-
yl}carbonyl)amino]benzoate

HPLC retention time (min.): 3.41; MS: 735 (2M+H)$^+$, 368 (M+H)$^+$.

EXAMPLE 3(353)

N-[3-(Methylsulfanyl)phenyl]-3-[phenyl(propyl)
amino]azetidine-1-carboxamide

HPLC retention time (min.): 3.50; MS: 711 (2M+H)$^+$, 356 (M+H)$^+$.

EXAMPLE 3(354)

N-(2-Methylphenyl)-3-[phenyl(propyl)amino]azeti-
dine-1-carboxamide

HPLC retention time (min.): 3.34; MS: 647 (2M+H)$^+$, 324 (M+H)$^+$.

EXAMPLE 3(355)

3-(1,4-Dioxa-8-azaspiro[4.5]dec-8-yl)-N-propylaze-
tidine-1-carboxamide

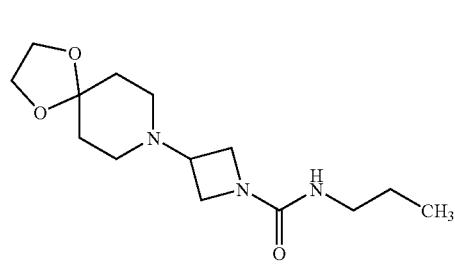

HPLC retention time (min.): 2.92(condition B); MS: 284 (M+H)$^+$.

EXAMPLE 3(356)

Ethyl N-{[3-(1,4-dioxa-8-azaspiro[4.5]dec-8-yl)aze-
tidin-1-yl]carbonyl}glycinate HPLC retention time (min.): 2.88(condition B); MS: 328 (M+H)$^+$.

EXAMPLE 3(357)

3-(1,4-Dioxa-8-azaspiro[4.5]dec-8-yl)-N-hexylazeti-
dine-1-carboxamide

HPLC retention time (min.): 3.08; MS: 326 (M+H)$^+$.

EXAMPLE 3(358)

3-(1,4-Dioxa-8-azaspiro[4.5]dec-8-yl)-N-(4-fluo-
rophenyl)azetidine-1-carboxamide HPLC retention time (min.): 2.89; MS: 671 (2M+H)$^+$, 336 (M+H)$^+$.

EXAMPLE 3(359)

3-(1,4-Dioxa-8-azaspiro[4.5]dec-8-yl)-N-(3-meth-
ylphenyl)azetidine-1-carboxamide HPLC retention time (min.): 2.97; MS: 663 (2M+H)$^+$, 332 (M+H)$^+$.

EXAMPLE 3(360)

3-(1,4-Dioxa-8-azaspiro[4.5]dec-8-yl)-N-(2-thien-2-
ylethyl)azetidine-1-carboxamide HPLC retention time (min.): 2.89; MS: 352 (M+H)$^+$.

EXAMPLE 3(361)

3-(1,4-Dioxa-8-azaspiro[4.5]dec-8-yl)-N-(4-isopro-
pylphenyl)azetidine-1-carboxamide HPLC retention time (min.): 3.20; MS: 719 (2M+H)$^+$, 360 (M+H)$^+$.

EXAMPLE 3(362)

N-(3-Chlorophenyl)-3-(1,4-dioxa-8-azaspiro[4.5]
dec-8-yl)azetidine-1-carboxamide HPLC retention time (min.): 3.05; MS: 703 (2M+H)$^+$, 354, 352 (M+H)$^+$.

EXAMPLE 3(363)

N-(2,5-Dimethylphenyl)-3-(1,4-dioxa-8-azaspiro
[4.5]dec-8-yl)azetidine-1-carboxamide HPLC retention time (min.): 2.98; MS: 691 (2M+H)$^+$, 346 (M+H)$^+$.

EXAMPLE 3(364)

N-(4-Chlorophenyl)-3-(1,4-dioxa-8-azaspiro[4.5]
dec-8-yl)azetidine-1-carboxamide HPLC retention time (min.): 3.06; MS: 703 (2M+H)$^+$, 354, 352 (M+H)$^+$.

EXAMPLE 3(365)

N-Benzyl-3-(1,4-dioxa-8-azaspiro[4.5]dec-8-yl)aze-
tidine-1-carboxamide

HPLC retention time (min.): 2.86; MS: 332 (M+H)$^+$.

EXAMPLE 3(366)

3-(1,4-Dioxa-8-azaspiro[4.5]dec-8-yl)-N-(1-naphthyl)azetidine-1-carboxamide

HPLC retention time (min.): 3.01; MS: 735 (2M+H)$^+$, 368 (M+H)$^+$.

EXAMPLE 3(367)

3-(1,4-Dioxa-8-azaspiro[4.5]dec-8-yl)-N-(2-naphthyl)azetidine-1-carboxamide

HPLC retention time (min.): 3.12; MS: 735 (2M+H)$^+$, 368 (M+H)$^+$.

EXAMPLE 3(368)

3-(1,4-Dioxa-8-azaspiro[4.5]dec-8-yl)-N-[1-(1-naphthyl)ethyl]azetidine-1-carboxamide HPLC retention time (min.): 3.16; MS: 791 (2M+H)$^+$, 396 (M+H)$^+$, 242.

EXAMPLE 3(369)

N-(3,4-Dimethylphenyl)-3-(1,4-dioxa-8-azaspiro[4.5]dec-8-yl)azetidine-1-carboxamide HPLC retention time (min.): 3.06; MS: 691 (2M+H)$^+$, 346 (M+H)$^+$.

EXAMPLE 3(370)

3-(1,4-Dioxa-8-azaspiro[4.5]dec-8-yl)-N-(4-methylphenyl)azetidine-1-carboxamide

HPLC retention time (min.): 2.97; MS: 663 (2M+H)$^+$, 332 (M+H)$^+$.

EXAMPLE 3(371)

N-Cyclohexyl-3-(1,4-dioxa-8-azaspiro[4.5]dec-8-yl)azetidine-1-carboxamide

HPLC retention time (min.): 2.91; MS: 647 (2M+H)$^+$, 324 (M+H)$^+$.

EXAMPLE 3(372)

N-(2,6-Dimethylphenyl)-3-(1,4-dioxa-8-azaspiro[4.5]dec-8-yl)azetidine-1-carboxamide HPLC retention time (min.): 2.90; MS: 691 (2M+H)$^+$, 346 (M+H)$^+$.

EXAMPLE 3(373)

3-(1,4-Dioxa-8-azaspiro[4.5]dec-8-yl)-N-(2-ethoxyphenyl)azetidine-1-carboxamide

HPLC retention time (min.): 3.00; MS: 723 (2M+H)$^+$, 362 (M+H)$^+$.

EXAMPLE 3(374)

3-(1,4-Dioxa-8-azaspiro[4.5]dec-8-yl)-N-(2-ethylphenyl)azetidine-1-carboxamide

HPLC retention time (min.): 2.96; MS: 691 (2M+H)$^+$, 346 (M+H)$^+$.

EXAMPLE 3(375)

3-(1,4-Dioxa-8-azaspiro[4.5]dec-8-yl)-N-(4-ethoxyphenyl)azetidine-1-carboxamide

HPLC retention time (min.): 2.98; MS: 723 (2M+H)$^+$, 362 (M+H)$^+$.

EXAMPLE 3(376)

3-(1,4-Dioxa-8-azaspiro[4.5]dec-8-yl)-N-(2-phenylethyl)azetidine-1-carboxamide

HPLC retention time (min.): 2.97; MS: 346 (M+H)$^+$.

EXAMPLE 3(377)

3-(1,4-Dioxa-8-azaspiro[4.5]dec-8-yl)-N-phenylazetidine-1-carboxamide

HPLC retention time (min.): 2.80; MS: 635 (2M+H)$^+$, 318 (M+H)$^+$.

EXAMPLE 3(378)

N-(2-Chlorophenyl)-3-(1,4-dioxa-8-azaspiro[4.5]dec-8-yl)azetidine-1-carboxamide

HPLC retention time (min.): 2.91; MS: 703 (2M+H)$^+$, 354, 352 (M+H)$^+$.

EXAMPLE 3(379)

3-(1,4-Dioxa-8-azaspiro[4.5]dec-8-yl)-N-(2-fluorophenyl)azetidine-1-carboxamide

HPLC retention time (min.): 2.76; MS: 336 (M+H)$^+$.

EXAMPLE 3(380)

3-(1,4-Dioxa-8-azaspiro[4.5]dec-8-yl)-N-[3-(trifluoromethyl)phenyl]azetidine-1-carboxamide HPLC retention time (min.): 3.16; MS: 771 (2M+H)$^+$, 386 (M+H)$^+$.

EXAMPLE 3(381)

N-Cyclopentyl-3-(1,4-dioxa-8-azaspiro[4.5]dec-8-yl)azetidine-1-carboxamide

HPLC retention time (min.): 2.74; MS: 310 (M+H)$^+$.

EXAMPLE 3(382)

N-(2,4-Dimethylphenyl)-3-(1,4-dioxa-8-azaspiro[4.5]dec-8-yl)azetidine-1-carboxamide HPLC retention time (min.): 2.97; MS: 691 (2M+H)$^+$, 346 (M+H)$^+$.

EXAMPLE 3(383)

N-(3,5-Dichlorophenyl)-3-(1,4-dioxa-8-azaspiro[4.5]dec-8-yl)azetidine-1-carboxamide HPLC retention time (min.): 3.23; MS: 773, 771 (2M+H)$^+$, 388, 386 (M+H)$^+$.

EXAMPLE 3(384)

N-[3,5-Bis(trifluoromethyl)phenyl]-3-(1,4-dioxa-8-azaspiro[4.5]dec-8-yl)azetidine-1-carboxamide HPLC retention time (min.): 3.39; MS: 907 (2M+H)$^+$, 454 (M+H)$^+$.

EXAMPLE 3(385)

3-(1,4-Dioxa-8-azaspiro[4.5]dec-8-yl)-N-(3-phenoxyphenyl)azetidine-1-carboxamide HPLC retention time (min.): 3.27; MS: 819 (2M+H)$^+$, 410 (M+H)$^+$.

EXAMPLE 3(386)

N-(3,5-Difluorophenyl)-3-(1,4-dioxa-8-azaspiro[4.5]dec-8-yl)azetidine-1-carboxamide HPLC retention time (min.): 3.04; MS: 707 (2M+H)$^+$, 354 (M+H)$^+$.

EXAMPLE 3(387)

3-(1,4-Dioxa-8-azaspiro[4.5]dec-8-yl)-N-(4-methoxyphenyl)azetidine-1-carboxamide HPLC retention time (min.): 2.85; MS: 695 (2M+H)$^+$, 348 (M+H)$^+$.

EXAMPLE 3(388)

N-(3,5-Dimethylphenyl)-3-(1,4-dioxa-8-azaspiro[4.5]dec-8-yl)azetidine-1-carboxamide HPLC retention time (min.): 3.08; MS: 691 (2M+H)$^+$, 346 (M+H)$^+$.

EXAMPLE 3(389)

3-(1,4-Dioxa-8-azaspiro[4.5]dec-8-yl)-N-(3-fluorophenyl)azetidine-1-carboxamide

HPLC retention time (min.): 2.94; MS: 671 (2M+H)$^+$, 336 (M+H)$^+$.

EXAMPLE 3(390)

Methyl 3-({[3-(1,4-dioxa-8-azaspiro[4.5]dec-8-yl)azetidin-1-yl]carbonyl}amino)benzoate HPLC retention time (min.): 2.96; MS: 751 (2M+H)$^+$, 376 (M+H)$^+$.

EXAMPLE 3(391)

3-(1,4-Dioxa-8-azaspiro[4.5]dec-8-yl)-N-[3-(methylsulfanyl)phenyl]azetidine-1-carboxamide HPLC retention time (min.): 3.05; MS: 727 (2M+H)$^+$, 364 (M+H)$^+$.

EXAMPLE 3(392)

3-(1,4-Dioxa-8-azaspiro[4.5]dec-8-yl)-N-(2-methylphenyl)azetidine-1-carboxamide

HPLC retention time (min.): 2.84; MS: 663 (2M+H)$^+$, 332 (M+H)$^+$.

EXAMPLE 3(393)

N-Propyl-3-pyrrolidin-1-ylazetidine-1-carboxamide

HPLC retention time (min.): 2.91(condition B); MS: 212 (M+H)$^+$.

EXAMPLE 3(394)

Ethyl N-[(3-pyrrolidin-1-ylazetidin-1-yl)carbonyl]glycinate

HPLC retention time (min.): 2.86(condition B); MS: 256 (M+H)$^+$.

EXAMPLE 3(395)

N-Hexyl-3-pyrrolidin-1-ylazetidine-1-carboxamide

HPLC retention time (min.): 3.03; MS: 254 (M+H)$^+$.

EXAMPLE 3(396)

N-(4-Fluorophenyl)-3-pyrrolidin-1-ylazetidine-1-carboxamide

HPLC retention time (min.): 2.69; MS: 264 (M+H)$^+$.

EXAMPLE 3(397)

N-(3-Methylphenyl)-3-pyrrolidin-1-ylazetidine-1-carboxamide

HPLC retention time (min.): 2.90; MS: 519 (2M+H)$^+$, 260 (M+H)$^+$.

EXAMPLE 3(398)

3-Pyrrolidin-1-yl-N-(2-thien-2-ylethyl)azetidine-1-carboxamide

HPLC retention time (min.): 2.79; MS: 280 (M+H)$^+$.

EXAMPLE 3(399)

N-(4-Isopropylphenyl)-3-pyrrolidin-1-ylazetidine-1-carboxamide

HPLC retention time (min.): 3.15; MS: 575 (2M+H)$^+$, 288 (M+H)$^+$.

EXAMPLE 3(400)

N-(3-Chlorophenyl)-3-pyrrolidin-1-ylazetidine-1-carboxamide

HPLC retention time (min.): 3.00; MS: 559 (2M+H)$^+$, 282, 280 (M+H)$^+$.

EXAMPLE 3(401)

N-(2,5-Dimethylphenyl)-3-pyrrolidin-1-ylazetidine-1-carboxamide

HPLC retention time (min.): 2.91; MS: 547 (2M+H)$^+$, 274 (M+H)$^+$.

EXAMPLE 3(402)

N-(4-Chlorophenyl)-3-pyrrolidin-1-ylazetidine-1-carboxamide

HPLC retention time (min.): 3.00; MS: 282, 280 (M+H)$^+$.

EXAMPLE 3(403)

N-Benzyl-3-pyrrolidin-1-ylazetidine-1-carboxamide

HPLC retention time (min.): 3.13(condition B); MS: 260 (M+H)$^+$.

EXAMPLE 3(404)

N-(1-Naphthyl)-3-pyrrolidin-1-ylazetidine-1-carboxamide

HPLC retention time (min.): 2.97; MS: 591 (2M+H)$^+$, 296 (M+H)$^+$.

EXAMPLE 3(405)

N-(2-Naphthyl)-3-pyrrolidin-1-ylazetidine-1-carboxamide

HPLC retention time (min.): 3.09; MS: 591 (2M+H)$^+$, 296 (M+H)$^+$.

EXAMPLE 3(406)

N-[1-(1-Naphthyl)ethyl]-3-pyrrolidin-1-ylazetidine-1-carboxamide

HPLC retention time (min.): 3.12; MS: 647 (2M+H)$^+$, 324 (M+H)$^+$, 170.

EXAMPLE 3(407)

N-(3,4-Dimethylphenyl)-3-pyrrolidin-1-ylazetidine-1-carboxamide

HPLC retention time (min.): 3.01; MS: 547 (2M+H)$^+$, 274 (M+H)$^+$.

EXAMPLE 3(408)

N-(4-Methylphenyl)-3-pyrrolidin-1-ylazetidine-1-carboxamide

HPLC retention time (min.): 2.89; MS: 519 (2M+H)$^+$, 260 (M+H)$^+$.

EXAMPLE 3(409)

N-Cyclohexyl-3-pyrrolidin-1-ylazetidine-1-carboxamide

HPLC retention time (min.): 2.80; MS: 252 (M+H)$^+$.

EXAMPLE 3(410)

N-(2,6-Dimethylphenyl)-3-pyrrolidin-1-ylazetidine-1-carboxamide

HPLC retention time (min.): 2.73; MS: 547 (2M+H)$^+$, 274 (M+H)$^+$.

EXAMPLE 3(411)

N-(2-Ethoxyphenyl)-3-pyrrolidin-1-ylazetidine-1-carboxamide

HPLC retention time (min.): 2.96; MS: 579 (2M+H)$^+$, 290 (M+H)$^+$.

EXAMPLE 3(412)

N-(2-Ethylphenyl)-3-pyrrolidin-1-ylazetidine-1-carboxamide

HPLC retention time (min.): 2.87; MS: 547 (2M+H)$^+$, 274 (M+H)$^+$.

EXAMPLE 3(413)

N-(4-Ethoxyphenyl)-3-pyrrolidin-1-ylazetidine-1-carboxamide

HPLC retention time (min.): 2.91; MS: 579 (2M+H)$^+$, 290 (M+H)$^+$.

EXAMPLE 3(414)

N-(2-Phenylethyl)-3-pyrrolidin-1-ylazetidine-1-carboxamide

HPLC retention time (min.): 2.90; MS: 274 (M+H)$^+$.

EXAMPLE 3(415)

N-Phenyl-3-pyrrolidin-1-ylazetidine-1-carboxamide

HPLC retention time (min.): 3.13(condition B); MS: 491 (2M+H)$^+$, 246 (M+H)$^+$.

EXAMPLE 3(416)

N-(2-Chlorophenyl)-3-pyrrolidin-1-ylazetidine-1-carboxamide

HPLC retention time (min.): 2.75; MS: 282, 280 (M+H)$^+$.

EXAMPLE 3(417)

N-(2-Fluorophenyl)-3-pyrrolidin-1-ylazetidine-1-carboxamide

HPLC retention time (min.): 3.14(condition B); MS: 527 (2M+H)$^+$, 264 (M+H)$^+$.

EXAMPLE 3(418)

3-Pyrrolidin-1-yl-N-[3-(trifluoromethyl)phenyl]azetidine-1-carboxamide

HPLC retention time (min.): 3.12; MS: 627 (2M+H)$^+$, 314 (M+H)$^+$.

EXAMPLE 3(419)

N-Cyclopentyl-3-pyrrolidin-1-ylazetidine-1-carboxamide

HPLC retention time (min.): 3.07(condition B); MS: 238 (M+H)$^+$.

EXAMPLE 3(420)

N-(2,4-Dimethylphenyl)-3-pyrrolidin-1-ylazetidine-1-carboxamide

HPLC retention time (min.): 2.92; MS: 547 (2M+H)$^+$, 274 (M+H)$^+$.

EXAMPLE 3(421)

N-(3,5-Dichlorophenyl)-3-pyrrolidin-1-ylazetidine-1-carboxamide

HPLC retention time (min.): 3.19; MS: 629, 627 (2M+H)$^+$, 316, 314 (M+H)$^+$.

EXAMPLE 3(422)

N-[3,5-Bis(trifluoromethyl)phenyl]-3-pyrrolidin-1-ylazetidine-1-carboxamide

HPLC retention time (min.): 3.35; MS: 763 (2M+H)$^+$, 382 (M+H)$^+$.

EXAMPLE 3(423)

N-(3-Phenoxyphenyl)-3-pyrrolidin-1-ylazetidine-1-carboxamide

HPLC retention time (min.): 3.24; MS: 675 (2M+H)$^+$, 338 (M+H)$^+$.

EXAMPLE 3(424)

N-(3,5-Difluorophenyl)-3-pyrrolidin-1-ylazetidine-1-carboxamide

HPLC retention time (min.): 2.97; MS: 282 (M+H)$^+$.

EXAMPLE 3(425)

N-(4-Methoxyphenyl)-3-pyrrolidin-1-ylazetidine-1-carboxamide

HPLC retention time (min.): 2.68; MS: 551 (2M+H)$^+$, 276 (M+H)$^+$.

EXAMPLE 3(426)

N-(3,5-Dimethylphenyl)-3-pyrrolidin-1-ylazetidine-1-carboxamide

HPLC retention time (min.): 3.04; MS: 547 (2M+H)$^+$, 274 (M+H)$^+$.

EXAMPLE 3(427)

N-(3-Fluorophenyl)-3-pyrrolidin-1-ylazetidine-1-carboxamide

HPLC retention time (min.): 2.84; MS: 264 (M+H)$^+$.

EXAMPLE 3(428)

Methyl 3-{[(3-pyrrolidin-1-ylazetidin-1-yl)carbonyl]amino}benzoate

HPLC retention time (min.): 2.91; MS: 607 (2M+H)$^+$, 304 (M+H)$^+$.

EXAMPLE 3(429)

N-[3-(Methylsulfanyl)phenyl]-3-pyrrolidin-1-ylazetidine-1-carboxamide

HPLC retention time (min.): 2.99; MS: 583 (2M+H)$^+$, 292 (M+H)$^+$.

EXAMPLE 3(430)

3-Piperidin-1-yl-N-propylazetidine-1-carboxamide

HPLC retention time (min.): 3.04(condition B); MS: 226 (M+H)$^+$.

EXAMPLE 3(431)

Ethyl N-[(3-piperidin-1-ylazetidin-1-yl)carbonyl]glycinate

HPLC retention time (min.): 2.98(condition B); MS: 270 (M+H)$^+$.

EXAMPLE 3(432)

N-Hexyl-3-piperidin-1-ylazetidine-1-carboxamide

HPLC retention time (min.): 3.06; MS: 268 (M+H)$^+$.

EXAMPLE 3(433)

N-(4-Fluorophenyl)-3-piperidin-1-ylazetidine-1-carboxamide

HPLC retention time (min.): 2.81; MS: 278 (M+H)$^+$.

EXAMPLE 3(434)

N-(3-Methylphenyl)-3-piperidin-1-ylazetidine-1-carboxamide

HPLC retention time (min.): 2.94; MS: 547 (2M+H)$^+$, 274 (M+H)$^+$.

EXAMPLE 3(435)

3-Piperidin-1-yl-N-(2-thien-2-ylethyl)azetidine-1-carboxamide

HPLC retention time (min.): 2.85; MS: 294 (M+H)$^+$.

EXAMPLE 3(436)

N-(4-Isopropylphenyl)-3-piperidin-1-ylazetidine-1-carboxamide

HPLC retention time (min.): 3.18; MS: 603 (2M+H)$^+$, 302 (M+H)$^+$.

EXAMPLE 3(437)

N-(3-Chlorophenyl)-3-piperidin-1-ylazetidine-1-carboxamide

HPLC retention time (min.): 3.02; MS: 587 (2M+H)$^+$, 296, 294 (M+H)$^+$.

EXAMPLE 3(438)

N-(2,5-Dimethylphenyl)-3-piperidin-1-ylazetidine-1-carboxamide

HPLC retention time (min.): 2.96; MS: 575 (2M+H)$^+$, 288 (M+H)$^+$.

EXAMPLE 3(439)

N-(4-Chlorophenyl)-3-piperidin-1-ylazetidine-1-carboxamide

HPLC retention time (min.): 3.03; MS: 587 (2M+H)$^+$, 296, 294 (M+H)$^+$.

EXAMPLE 3(440)

N-Benzyl-3-piperidin-1-ylazetidine-1-carboxamide

HPLC retention time (min.): 2.77; MS: 274 (M+H)$^+$.

EXAMPLE 3(441)

N-(1-Naphthyl)-3-piperidin-1-ylazetidine-1-carboxamide

HPLC retention time (min.): 2.99; MS: 619 (2M+H)$^+$, 310 (M+H)$^+$.

EXAMPLE 3(442)

N-(2-Naphthyl)-3-piperidin-1-ylazetidine-1-carboxamide

HPLC retention time (min.): 3.11.; MS: 619 (2M+H)$^+$, 310 (M+H)$^+$.

EXAMPLE 3(443)

N-[1-(1-Naphthyl)ethyl]-3-piperidin-1-ylazetidine-1-carboxamide

HPLC retention time (min.): 3.16; MS: 675 (2M+H)$^+$, 338 (M+H)$^+$, 184.

EXAMPLE 3(444)

N-(3,4-Dimethylphenyl)-3-piperidin-1-ylazetidine-1-carboxamide

HPLC retention time (min.): 3.04; MS: 575 (2M+H)$^+$, 288 (M+H)$^+$.

EXAMPLE 3(445)

N-(4-Methylphenyl)-3-piperidin-1-ylazetidine-1-carboxamide

HPLC retention time (min.): 2.93; MS: 547 (2M+H)$^+$, 274 (M+H)$^+$.

EXAMPLE 3(446)

N-Cyclohexyl-3-piperidin-1-ylazetidine-1-carboxamide

HPLC retention time (min.): 2.85; MS: 266 (M+H)$^+$.

EXAMPLE 3(447)

N-(2,6-Dimethylphenyl)-3-piperidin-1-ylazetidine-1-carboxamide

HPLC retention time (min.): 2.82; MS: 575 (2M+H)$^+$, 288 (M+H)$^+$.

EXAMPLE 3(448)

N-(2-Ethoxyphenyl)-3-piperidin-1-ylazetidine-1-carboxamide

HPLC retention time (min.): 2.98; MS: 607 (2M+H)$^+$, 304 (M+H)$^+$.

EXAMPLE 3(449)

N-(2-Ethylphenyl)-3-piperidin-1-ylazetidine-1-carboxamide

HPLC retention time (min.): 2.92; MS: 575 (2M+H)$^+$, 288 (M+H)$^+$.

EXAMPLE 3(450)

N-(4-Ethoxyphenyl)-3-piperidin-1-ylazetidine-1-carboxamide

HPLC retention time (min.): 2.96; MS: 607 (2M+H)$^+$, 304 (M+H)$^+$.

EXAMPLE 3(451)

N-(2-Phenylethyl)-3-piperidin-1-ylazetidine-1-carboxamide

HPLC retention time (min.): 2.94; MS: 288 (M+H)$^+$.

EXAMPLE 3(452)

N-Phenyl-3-piperidin-1-ylazetidine-1-carboxamide

HPLC retention time (min.): 2.66; MS: 260 (M+H)$^+$.

EXAMPLE 3(453)

N-(2-Chlorophenyl)-3-piperidin-1-ylazetidine-1-carboxamide

HPLC retention time (min.): 2.85; MS: 296, 294 (M+H)$^+$.

EXAMPLE 3(454)

N-(2-Fluorophenyl)-3-piperidin-1-ylazetidine-1-carboxamide

HPLC retention time (min.): 3.28(condition B); MS: 555 (2M+H)$^+$, 278 (M+H)$^+$.

EXAMPLE 3(455)

3-Piperidin-1-yl-N-[3-(trifluoromethyl)phenyl]azetidine-1-carboxamide

HPLC retention time (min.): 3.14; MS: 655 (2M+H)$^+$, 328 (M+H)$^+$.

EXAMPLE 3(456)

N-Cyclopentyl-3-piperidin-1-ylazetidine-1-carboxamide

HPLC retention time (min.): 3.19(condition B); MS: 252 (M+H)$^+$.

EXAMPLE 3(457)

N-(2,4-Dimethylphenyl)-3-piperidin-1-ylazetidine-1-carboxamide

HPLC retention time (min.): 2.95; MS: 575 (2M+H)$^+$, 288 (M+H)$^+$.

EXAMPLE 3(458)

N-(3,5-Dichlorophenyl)-3-piperidin-1-ylazetidine-1-carboxamide

HPLC retention time (min.): 3.22; MS: 657, 655 (2M+H)$^+$, 330, 328 (M+H)$^+$.

EXAMPLE 3(459)

N-[3,5-Bis(trifluoromethyl)phenyl]-3-piperidin-1-ylazetidine-1-carboxamide

HPLC retention time (min.): 3.38; MS: 791 (2M+H)$^+$, 396 (M+H)$^+$.

EXAMPLE 3(460)

N-(3-Phenoxyphenyl)-3-piperidin-1-ylazetidine-1-carboxamide

HPLC retention time (min.): 3.26; MS: 703 (2M+H)$^+$, 352 (M+H)$^+$.

EXAMPLE 3(461)

N-(3,5-Difluorophenyl)-3-piperidin-1-ylazetidine-1-carboxamide

HPLC retention time (min.): 3.01; MS: 591 (2M+H)$^+$, 296 (M+H)$^+$.

EXAMPLE 3(462)

N-(4-Methoxyphenyl)-3-piperidin-1-ylazetidine-1-carboxamide

HPLC retention time (min.): 2.78; MS: 579 (2M+H)$^+$, 290 (M+H)$^+$.

EXAMPLE 3(463)

N-(3,5-Dimethylphenyl)-3-piperidin-1-ylazetidine-1-carboxamide

HPLC retention time (min.): 3.05; MS: 575 (2M+H)$^+$, 288 (M+H)$^+$.

EXAMPLE 3(464)

N-(3-Fluorophenyl)-3-piperidin-1-ylazetidine-1-carboxamide

HPLC retention time (min.): 2.88; MS: 555 (2M+H)$^+$, 278 (M+H)$^+$.

EXAMPLE 3(465)

Methyl 3-{[(3-piperidin-1-ylazetidin-1-yl)carbonyl]amino}benzoate

HPLC retention time (min.): 2.94; MS: 635 (2M+H)$^+$, 318 (M+H)$^+$.

EXAMPLE 3(466)

N-[3-(Methylsulfanyl)phenyl]-3-piperidin-1-ylazetidine-1-carboxamide

HPLC retention time (min.): 3.02; MS: 611 (2M+H)$^+$, 306 (M+H)$^+$.

EXAMPLE 3(467)

N-(2-Methylphenyl)-3-piperidin-1-ylazetidine-1-carboxamide

HPLC retention time (min.): 2.71; MS: 274 (M+H)$^+$.

EXAMPLE 3(468)

3-Azepan-1-yl-N-propylazetidine-1-carboxamide

HPLC retention time (min.): 3.19(condition B); MS: 240 (M+H)$^+$.

EXAMPLE 3(469)

Ethyl N-[(3-azepan-1-ylazetidin-1-yl)carbonyl]glycinate

HPLC retention time (min.): 3.12(condition B); MS: 284 (M+H)$^+$.

EXAMPLE 3(470)

3-Azepan-1-yl-N-hexylazetidine-1-carboxamide

HPLC retention time (min.): 3.10; MS: 282 (M+H)$^+$.

EXAMPLE 3(471)

3-Azepan-1-yl-N-(4-fluorophenyl)azetidine-1-carboxamide

HPLC retention time (min.): 2.91; MS: 292 (M+H)$^+$.

EXAMPLE 3(472)

3-Azepan-1-yl-N-(3-methylphenyl)azetidine-1-carboxamide

HPLC retention time (min.): 3.01; MS: 575 (2M+H)$^+$, 288 (M+H)$^+$.

EXAMPLE 3(473)

3-Azepan-1-yl-N-(2-thien-2-ylethyl)azetidine-1-carboxamide

HPLC retention time (min.): 2.93; MS: 308 (M+H)$^+$.

EXAMPLE 3(474)

3-Azepan-1-yl-N-(4-isopropylphenyl)azetidine-1-carboxamide

HPLC retention time (min.): 3.23; MS: 631 (2M+H)$^+$, 316 (M+H)$^+$.

EXAMPLE 3(475)

3-Azepan-1-yl-N-(3-chlorophenyl)azetidine-1-carboxamide

HPLC retention time (min.): 3.09; MS: 615 (2M+H)$^+$, 310, 308 (M+H)$^+$.

EXAMPLE 3(476)

3-Azepan-1-yl-N-(2,5-dimethylphenyl)azetidine-1-carboxamide

HPLC retention time (min.): 3.02; MS: 603 (2M+H)$^+$, 302 (M+H)$^+$.

EXAMPLE 3(477)

3-Azepan-1-yl-N-(4-chlorophenyl)azetidine-1-carboxamide

HPLC retention time (min.): 3.08; MS: 310, 308 (M+H)$^+$.

EXAMPLE 3(478)

3-Azepan-1-yl-N-benzylazetidine-1-carboxamide

HPLC retention time (min.): 2.89; MS: 288 (M+H)$^+$.

EXAMPLE 3(479)

3-Azepan-1-yl-N-(1-naphthyl)azetidine-1-carboxamide

HPLC retention time (min.): 3.05; MS: 647 (2M+H)$^+$, 324 (M+H)$^+$.

EXAMPLE 3(480)

3-Azepan-1-yl-N-(2-naphthyl)azetidine-1-carboxamide

HPLC retention time (min.): 3.15; MS: 647 (2M+H)$^+$, 324 (M+H)$^+$.

EXAMPLE 3(481)

3-Azepan-1-yl-N-[1-(1-naphthyl)ethyl]azetidine-1-carboxamide

HPLC retention time (min.): 3.21; MS: 703 (2M+H)$^+$, 352 (M+H)$^+$.

EXAMPLE 3(482)

3-Azepan-1-yl-N-(3,4-dimethylphenyl)azetidine-1-carboxamide

HPLC retention time (min.): 3.09; MS: 603 (2M+H)$^+$, 302 (M+H)$^+$.

EXAMPLE 3(483)

3-Azepan-1-yl-N-(4-methylphenyl)azetidine-1-carboxamide

HPLC retention time (min.): 3.00; MS: 575 (2M+H)$^+$, 288 (M+H)$^+$.

EXAMPLE 3(484)

3-Azepan-1-yl-N-cyclohexylazetidine-1-carboxamide

HPLC retention time (min.): 2.92; MS: 280 (M+H)$^+$.

EXAMPLE 3(485)

3-Azepan-1-yl-N-(2,6-dimethylphenyl)azetidine-1-carboxamide

HPLC retention time (min.): 2.91; MS: 603 (2M+H)$^+$, 302 (M+H)$^+$.

EXAMPLE 3(486)

3-Azepan-1-yl-N-(2-ethoxyphenyl)azetidine-1-carboxamide

HPLC retention time (min.): 3.04; MS: 635 (2M+H)$^+$, 318 (M+H)$^+$.

EXAMPLE 3(487)

3-Azepan-1-yl-N-(2-ethylphenyl)azetidine-1-carboxamide

HPLC retention time (min.): 2.98; MS: 603 (2M+H)$^+$, 302 (M+H)$^+$.

EXAMPLE 3(488)

3-Azepan-1-yl-N-(4-ethoxyphenyl)azetidine-1-carboxamide

HPLC retention time (min.): 3.01; MS: 635 (2M+H)$^+$, 318 (M+H)$^+$.

EXAMPLE 3(489)

3-Azepan-1-yl-N-(2-phenylethyl)azetidine-1-carboxamide

HPLC retention time (min.): 3.00; MS: 302 (M+H)$^+$.

EXAMPLE 3(490)

3-Azepan-1-yl-N-phenylazetidine-1-carboxamide

HPLC retention time (min.): 2.84; MS: 274 (M+H)$^+$.

EXAMPLE 3(491)

3-Azepan-1-yl-N-(2-chlorophenyl)azetidine-1-carboxamide

HPLC retention time (min.): 2.93; MS: 310, 308 (M+H)$^+$.

EXAMPLE 3(492)

3-Azepan-1-yl-N-(2-fluorophenyl)azetidine-1-carboxamide

HPLC retention time (min.): 2.79; MS: 292 (M+H)$^+$.

EXAMPLE 3(493)

3-Azepan-1-yl-N-[3-(trifluoromethyl)phenyl]azetidine-1-carboxamide

HPLC retention time (min.): 3.19; MS: 342 (M+H)$^+$.

EXAMPLE 3(494)

3-Azepan-1-yl-N-cyclopentylazetidine-1-carboxamide

HPLC retention time (min.): 2.78; MS: 266 (M+H)$^+$.

EXAMPLE 3(495)

3-Azepan-1-yl-N-(2,4-dimethylphenyl)azetidine-1-carboxamide

HPLC retention time (min.): 3.01; MS: 603 (2M+H)$^+$, 302 (M+H)$^+$.

EXAMPLE 3(496)

3-Azepan-1-yl-N-(3,5-dichlorophenyl)azetidine-1-carboxamide

HPLC retention time (min.): 3.26; MS: 685, 683 (2M+H)$^+$, 344, 342 (M+H)$^+$.

EXAMPLE 3(497)

3-Azepan-1-yl-N-[3,5-bis(trifluoromethyl)phenyl]azetidine-1-carboxamide

HPLC retention time (min.): 3.41; MS: 819 (2M+H)$^+$, 410 (M+H)$^+$.

EXAMPLE 3(498)

3-Azepan-1-yl-N-(3-phenoxyphenyl)azetidine-1-carboxamide

HPLC retention time (min.): 3.31; MS: 731 (2M+H)$^+$, 366 (M+H)$^+$.

EXAMPLE 3(499)

3-Azepan-1-yl-N-(3,5-difluorophenyl)azetidine-1-carboxamide

HPLC retention time (min.): 3.06; MS: 310 (M+H)$^+$.

EXAMPLE 3(500)

3-Azepan-1-yl-N-(4-methoxyphenyl)azetidine-1-carboxamide

HPLC retention time (min.): 2.88; MS: 607 (2M+H)$^+$, 304 (M+H)$^+$.

EXAMPLE 3(501)

3-Azepan-1-yl-N-(3,5-dimethylphenyl)azetidine-1-carboxamide

HPLC retention time (min.): 3.11; MS: 603 (2M+H)$^+$, 302 (M+H)$^+$.

EXAMPLE 3(502)

3-Azepan-1-yl-N-(3-fluorophenyl)azetidine-1-carboxamide

HPLC retention time (min.): 2.96; MS: 583 (2M+H)$^+$, 292 (M+H)$^+$.

EXAMPLE 3(503)

Methyl 3-{[(3-azepan-1-ylazetidin-1-yl)carbonyl]amino}benzoate

HPLC retention time (min.): 2.99; MS: 663 (2M+H)$^+$, 332 (M+H)$^+$.

EXAMPLE 3(504)

3-Azepan-1-yl-N-[3-(methylsulfanyl)phenyl]azetidine-1-carboxamide

HPLC retention time (min.): 3.07; MS: 639 (2M+H)$^+$, 320 (M+H)$^+$.

EXAMPLE 3(505)

3-Azepan-1-yl-N-(2-methylphenyl)azetidine-1-carboxamide

HPLC retention time (min.): 2.86; MS: 575 (2M+H)$^+$, 288 (M+H)$^+$.

EXAMPLE 3(506)

3-(Diisobutylamino)-N-ethylazetidine-1-carboxamide

HPLC retention time (min.): 2.76; MS: 256 (M+H)$^+$.

EXAMPLE 3(507)

3-(Diisobutylamino)-N-propylazetidine-1-carboxamide

HPLC retention time (min.): 2.89; MS: 270 (M+H)$^+$.

EXAMPLE 3(508)

Ethyl N-{[3-(diisobutylamino)azetidin-1-yl]carbonyl}glycinate

HPLC retention time (min.): 2.88; MS: 314 (M+H)$^+$.

EXAMPLE 3(509)

3-(Diisobutylamino)-N-hexylazetidine-1-carboxamide

HPLC retention time (min.): 3.28; MS: 312 (M+H)$^+$.

EXAMPLE 3(510)

3-(Diisobutylamino)-N-(4-fluorophenyl)azetidine-1-carboxamide

HPLC retention time (min.): 3.14; MS: 322 (M+H)$^+$.

EXAMPLE 3(511)

3-(Diisobutylamino)-N-(3-methylphenyl)azetidine-1-carboxamide

HPLC retention time (min.): 3.20; MS: 318 (M+H)+.

EXAMPLE 3(512)

3-(Diisobutylamino)-N-(2-thien-2-ylethyl)azetidine-1-carboxamide

HPLC retention time (min.): 3.13; MS: 338 (M+H)+.

EXAMPLE 3(513)

3-(Diisobutylamino)-N-(4-isopropylphenyl)azetidine-1-carboxamide

HPLC retention time (min.): 3.40; MS: 346 (M+H)+.

EXAMPLE 3(514)

N-(3-Chlorophenyl)-3-(diisobutylamino)azetidine-1-carboxamide

HPLC retention time (min.): 3.27; MS: 340, 338 (M+H)+.

EXAMPLE 3(515)

3-(Diisobutylamino)-N-(2,5-dimethylphenyl)azetidine-1-carboxamide

HPLC retention time (min.): 3.20; MS: 332 (M+H)+.

EXAMPLE 3(516)

N-(4-Chlorophenyl)-3-(diisobutylamino)azetidine-1-carboxamide

HPLC retention time (min.): 3.27; MS: 340, 338 (M+H)+.

EXAMPLE 3(517)

N-Benzyl-3-(diisobutylamino)azetidine-1-carboxamide

HPLC retention time (min.): 3.10; MS: 318 (M+H)+.

EXAMPLE 3(518)

3-(Diisobutylamino)-N-(1-naphthyl)azetidine-1-carboxamide

HPLC retention time (min.): 3.22; MS: 707 (2M+H)+, 354 (M+H)+.

EXAMPLE 3(519)

3-(Diisobutylamino)-N-(2-naphthyl)azetidine-1-carboxamide

HPLC retention time (min.): 3.33; MS: 707 (2M+H)+, 354 (M+H)+.

EXAMPLE 3(520)

3-(Diisobutylamino)-N-[1-(1-naphthyl)ethyl]azetidine-1-carboxamide

HPLC retention time (min.): 3.36; MS: 382 (M+H)+.

EXAMPLE 3(521)

3-(Diisobutylamino)-N-(3,4-dimethylphenyl)azetidine-1-carboxamide

HPLC retention time (min.): 3.26; MS: 332 (M+H)+.

EXAMPLE 3(522)

3-(Diisobutylamino)-N-(4-methylphenyl)azetidine-1-carboxamide

HPLC retention time (min.): 3.19; MS: 318 (M+H)+.

EXAMPLE 3(523)

N-Cyclohexyl-3-(diisobutylamino)azetidine-1-carboxamide

HPLC retention time (min.): 3.13; MS: 310 (M+H)+.

EXAMPLE 3(524)

3-(Diisobutylamino)-N-(2,6-dimethylphenyl)azetidine-1-carboxamide

HPLC retention time (min.): 3.11; MS: 663 (2M+H)+, 332 (M+H)+.

EXAMPLE 3(525)

3-(Diisobutylamino)-N-(2-ethoxyphenyl)azetidine-1-carboxamide

HPLC retention time (min.): 3.25; MS: 348 (M+H)+.

EXAMPLE 3(526)

3-(diisobutylamino)-N-(2-ethylphenyl)azetidine-1-carboxamide

HPLC retention time (min.): 3.19; MS: 332 (M+H)+.

EXAMPLE 3(527)

3-(Diisobutylamino)-N-(4-ethoxyphenyl)azetidine-1-carboxamide

HPLC retention time (min.): 3.20; MS: 695 (2M+H)+, 348 (M+H)+.

EXAMPLE 3(528)

3-(Diisobutylamino)-N-(2-phenylethyl)azetidine-1-carboxamide

HPLC retention time (min.): 3.17; MS: 332 (M+H)+.

EXAMPLE 3(529)

3-(Diisobutylamino)-N-phenylazetidine-1-carboxamide

HPLC retention time (min.): 3.10; MS: 304 (M+H)+.

EXAMPLE 3(530)

N-(2-Chlorophenyl)-3-(diisobutylamino)azetidine-1-carboxamide

HPLC retention time (min.): 3.16; MS: 340, 338 (M+H)$^+$.

EXAMPLE 3(531)

3-(Diisobutylamino)-N-(2-fluorophenyl)azetidine-1-carboxamide

HPLC retention time (min.): 3.07; MS: 322 (M+H)$^+$.

EXAMPLE 3(532)

3-(Diisobutylamino)-N-[3-(trifluoromethyl)phenyl]azetidine-1-carboxamide

HPLC retention time (min.): 3.36; MS: 372 (M+H)$^+$.

EXAMPLE 3(533)

N-Cyclopentyl-3-(diisobutylamino)azetidine-1-carboxamide

HPLC retention time (min.): 3.04; MS: 296 (M+H)$^+$.

EXAMPLE 3(534)

3-(Diisobutylamino)-N-(2,4-dimethylphenyl)azetidine-1-carboxamide

HPLC retention time (min.): 3.20; MS: 332 (M+H)$^+$.

EXAMPLE 3(535)

N-(3,5-Dichlorophenyl)-3-(diisobutylamino)azetidine-1-carboxamide

HPLC retention time (min.): 3.44; MS: 374, 372 (M+H)$^+$.

EXAMPLE 3(536)

N-[3,5-Bis(trifluoromethyl)phenyl]-3-(diisobutylamino)azetidine-1-carboxamide

HPLC retention time (min.): 3.57; MS: 440 (M+H)$^+$.

EXAMPLE 3(537)

3-(Diisobutylamino)-N-(3-phenoxyphenyl)azetidine-1-carboxamide

HPLC retention time (min.): 3.47; MS: 791 (2M+H)$^+$, 396 (M+H)$^+$.

EXAMPLE 3(538)

N-(3,5-Difluorophenyl)-3-(diisobutylamino)azetidine-1-carboxamide

HPLC retention time (min.): 3.27; MS: 340 (M+H)$^+$.

EXAMPLE 3(539)

3-(Diisobutylamino)-N-(4-methoxyphenyl)azetidine-1-carboxamide

HPLC retention time (min.): 3.09; MS: 334 (M+H)$^+$.

EXAMPLE 3(540)

3-(Diisobutylamino)-N-(3,5-dimethylphenyl)azetidine-1-carboxamide

HPLC retention time (min.): 3.29; MS: 332 (M+H)$^+$.

EXAMPLE 3(541)

3-(Diisobutylamino)-N-(3-fluorophenyl)azetidine-1-carboxamide

HPLC retention time (min.): 3.18; MS: 322 (M+H)$^+$.

EXAMPLE 3(542)

Methyl 3-({[3-(diisobutylamino)azetidin-1-yl]carbonyl}amino)benzoate

HPLC retention time (min.): 3.16; MS: 723 (2M+H)$^+$, 362 (M+H)$^+$.

EXAMPLE 3(543)

3-(Diisobutylamino)-N-[3-(methylsulfanyl)phenyl]azetidine-1-carboxamide

HPLC retention time (min.): 3.25; MS: 699 (2M+H)$^+$, 350 (M+H)$^+$.

Example 3(544)

3-(Diisobutylamino)-N-(2-methylphenyl)azetidine-1-carboxamide

HPLC retention time (min.): 3.10; MS: 318 (M+H)$^+$.

EXAMPLE 3(545)

3-Morpholin-4-yl-N-propylazetidine-1-carboxamide

HPLC retention time (min.): 2.68(condition B); MS: 228 (M+H)$^+$.

EXAMPLE 3(546)

N-Hexyl-3-morpholin-4-ylazetidine-1-carboxamide

HPLC retention time (min.): 3.01; MS: 270 (M+H)$^+$.

EXAMPLE 3(547)

N-(4-Fluorophenyl)-3-morpholin-4-ylazetidine-1-carboxamide

HPLC retention time (min.): 3.02(condition B); MS: 559 (2M+H)$^+$, 280 (M+H)$^+$.

EXAMPLE 3(548)

N-(3-Methylphenyl)-3-morpholin-4-ylazetidine-1-carboxamide

HPLC retention time (min.): 2.86; MS: 551 (2M+H)$^+$, 276 (M+H)$^+$.

EXAMPLE 3(549)

3-Morpholin-4-yl-N-(2-thien-2-ylethyl)azetidine-1-carboxamide

HPLC retention time (min.): 2.73; MS: 296 (M+H)$^+$.

EXAMPLE 3(550)

N-(4-Isopropylphenyl)-3-morpholin-4-ylazetidine-1-carboxamide

HPLC retention time (min.): 3.14; MS: 607 (2M+H)$^+$, 304 (M+H)$^+$.

EXAMPLE 3(551)

N-(3-Chlorophenyl)-3-morpholin-4-ylazetidine-1-carboxamide

HPLC retention time (min.): 2.97; MS: 591 (2M+H)$^+$, 298, 296 (M+H)$^+$.

EXAMPLE 3(552)

N-(2,5-Dimethylphenyl)-3-morpholin-4-ylazetidine-1-carboxamide

HPLC retention time (min.): 2.88; MS: 579 (2M+H)$^+$, 290 (M+H)$^+$.

EXAMPLE 3(553)

N-(4-Chlorophenyl)-3-morpholin-4-ylazetidine-1-carboxamide

HPLC retention time (min.): 2.98; MS: 298, 296 (M+H)$^+$.

EXAMPLE 3(554)

N-Benzyl-3-morpholin-4-ylazetidine-1-carboxamide

HPLC retention time (min.): 2.97(condition B); MS: 276 (M+H)$^+$.

EXAMPLE 3(555)

3-Morpholin-4-yl-N-(1-naphthyl)azetidine-1-carboxamide

HPLC retention time (min.): 2.93; MS: 623 (2M+H)$^+$, 312 (M+H)$^+$.

EXAMPLE 3(556)

3-Morpholin-4-yl-N-(2-naphthyl)azetidine-1-carboxamide

HPLC retention time (min.): 3.06; MS: 623 (2M+H)$^+$, 312 (M+H)$^+$.

EXAMPLE 3(557)

3-Morpholin-4-yl-N-[1-(1-naphthyl)ethyl]azetidine-1-carboxamide

HPLC retention time (min.): 3.12; MS: 679 (2M+H)$^+$, 340 (M+H)$^+$, 186.

EXAMPLE 3(558)

N-(3,4-Dimethylphenyl)-3-morpholin-4-ylazetidine-1-carboxamide

HPLC retention time (min.): 2.98; MS: 579 (2M+H)$^+$, 290 (M+H)$^+$.

EXAMPLE 3(559)

N-(4-Methylphenyl)-3-morpholin-4-ylazetidine-1-carboxamide

HPLC retention time (min.): 2.86; MS: 551 (2M+H)$^+$, 276 (M+H)$^+$.

EXAMPLE 3(560)

N-Cyclohexyl-3-morpholin-4-ylazetidine-1-carboxamide

HPLC retention time (min.): 2.73; MS: 268 (M+H)$^+$.

EXAMPLE 3(561)

N-(2,6-Dimethylphenyl)-3-morpholin-4-ylazetidine-1-carboxamide

HPLC retention time (min.): 2.57; MS: 290 (M+H)$^+$.

EXAMPLE 3(562)

N-(2-Ethoxyphenyl)-3-morpholin-4-ylazetidine-1-carboxamide

HPLC retention time (min.): 2.91; MS: 611 (2M+H)$^+$, 306 (M+H)$^+$.

EXAMPLE 3(563)

N-(2-Ethylphenyl)-3-morpholin-4-ylazetidine-1-carboxamide

HPLC retention time (min.): 2.81; MS: 579 (2M+H)$^+$, 290 (M+H)$^+$.

EXAMPLE 3(564)

N-(4-Ethoxyphenyl)-3-morpholin-4-ylazetidine-1-carboxamide

HPLC retention time (min.): 2.88; MS: 611 (2M+H)$^+$, 306 (M+H)$^+$.

EXAMPLE 3(565)

3-Morpholin-4-yl-N-(2-phenylethyl)azetidine-1-carboxamide

HPLC retention time (min.): 2.87; MS: 290 (M+H)$^+$.

EXAMPLE 3(566)

3-Morpholin-4-yl-N-phenylazetidine-1-carboxamide

HPLC retention time (-min.): 2.96(condition B); MS: 523 (2M+H)$^+$, 262 (M+H)$^+$.

EXAMPLE 3(567)

N-(2-Chlorophenyl)-3-morpholin-4-ylazetidine-1-carboxamide

HPLC retention time (min.): 3.10(condition B); MS: 591 (2M+H)$^+$, 298, 296 (M+H)$^+$.

EXAMPLE 3(568)

N-(2-Fluorophenyl)-3-morpholin-4-ylazetidine-1-carboxamide

HPLC retention time (min.): 2.96 (condition B); MS: 559 (2M+H)$^+$, 280 (M+H)$^+$.

EXAMPLE 3(569)

3-Morpholin-4-yl-N-[3-(trifluoromethyl)phenyl]azetidine-1-carboxamide

HPLC retention time (min.): 3.09; MS: 330 (M+H)$^+$.

EXAMPLE 3(570)

N-Cyclopentyl-3-morpholin-4-ylazetidine-1-carboxamide

HPLC retention time (min.): 2.91(condition B); MS: 254 (M+H)$^+$.

EXAMPLE 3(571)

N-(2,4-Dimethylphenyl)-3-morpholin-4-ylazetidine-1-carboxamide

HPLC retention time (min.): 2.88; MS: 579 (2M+H)$^+$, 290 (M+H)$^+$.

EXAMPLE 3(572)

N-(3,5-Dichlorophenyl)-3-morpholin-4-ylazetidine-1-carboxamide

HPLC retention time (min.): 3.16; MS: 661, 659 (2M+H)$^+$, 332, 330 (M+H)$^+$.

EXAMPLE 3(573)

N-[3,5-Bis(trifluoromethyl)phenyl]-3-morpholin-4-ylazetidine-1-carboxamide

HPLC retention time (min.): 3.34; MS: 398 (M+H)$^+$.

EXAMPLE 3(574)

3-Morpholin-4-yl-N-(3-phenoxyphenyl)azetidine-1-carboxamide

HPLC retention time (min.): 3.21; MS: 707 (2M+H)$^+$, 354 (M+H)$^+$.

EXAMPLE 3(575)

N-(3,5-Difluorophenyl)-3-morpholin-4-ylazetidine-1-carboxamide

HPLC retention time (min.): 2.95; MS: 298 (M+H)$^+$.

EXAMPLE 3(576)

N-(4-Methoxyphenyl)-3-morpholin-4-ylazetidine-1-carboxamide

HPLC retention time (min.): 2.97(condition B); MS: 583 (2M+H)$^+$, 292 (M+H)$^+$.

EXAMPLE 3(577)

N-(3,5-Dimethylphenyl)-3-morpholin-4-ylazetidine-1-carboxamide

HPLC retention time (min.): 3.01; MS: 579 (2M+H)$^+$, 290 (M+H)$^+$.

EXAMPLE 3(578)

N-(3-Fluorophenyl)-3-morpholin-4-ylazetidine-1-carboxamide

HPLC retention time (min.): 2.77; MS: 280 (M+H)$^+$.

EXAMPLE 3(579)

Methyl 3-{[(3-morpholin-4-ylazetidin-1-yl)carbonyl]amino}benzoate

HPLC retention time (min.): 2.88; MS: 639 (2M+H)$^+$, 320 (M+H)$^+$.

EXAMPLE 3(580)

N-[3-(Methylsulfanyl)phenyl]-3-morpholin-4-ylazetidine-1-carboxamide

HPLC retention time (min.): 2.97; MS: 615 (2M+H)$^+$, 308 (M+H)$^+$.

EXAMPLE 3(581)

N-Hexyl-3-(4-methylpiperazin-1-yl)azetidine-1-carboxamide

HPLC retention time (min.): 3.01; MS: 565 (2M+H)$^+$, 283 (M+H)$^+$.

EXAMPLE 3(582)

N-(4-Fluorophenyl)-3-(4-methylpiperazin-1-yl)azetidine-1-carboxamide

HPLC retention time (min.): 2.78; MS: 585 (2M+H)$^+$, 293 (M+H)$^+$.

EXAMPLE 3(583)

N-(3-Methylphenyl)-3-(4-methylpiperazin-1-yl)azetidine-1-carboxamide

HPLC retention time (min.): 2.89; MS: 577 (2M+H)$^+$, 289 (M+H)$^+$.

EXAMPLE 3(584)

3-(4-Methylpiperazin-1-yl)-N-(2-thien-2-ylethyl)azetidine-1-carboxamide

HPLC retention time (min.): 2.79; MS: 617 (2M+H)$^+$, 309 (M+H)$^+$.

EXAMPLE 3(585)

N-(4-Isopropylphenyl)-3-(4-methylpiperazin-1-yl)azetidine-1-carboxamide

HPLC retention time (min.): 3.13; MS: 633 (2M+H)$^+$, 317 (M+H)$^+$.

EXAMPLE 3(586)

N-(3-Chlorophenyl)-3-(4-methylpiperazin-1-yl)azetidine-1-carboxamide

HPLC retention time (min.): 3.00; MS: 617 (2M+H)$^+$, 309 (M+H)$^+$.

EXAMPLE 3(587)

N-(2,5-Dimethylphenyl)-3-(4-methylpiperazin-1-yl)azetidine-1-carboxamide

HPLC retention time (min.): 2.90; MS: 605 (2M+H)$^+$, 303 (M+H)$^+$.

EXAMPLE 3(588)

N-(4-Chlorophenyl)-3-(4-methylpiperazin-1-yl)azetidine-1-carboxamide

HPLC retention time (min.): 2.99; MS: 617 (2M+H)$^+$, 311, 309 (M+H)$^+$.

EXAMPLE 3(589)

N-Benzyl-3-(4-methylpiperazin-1-yl)azetidine-1-carboxamide

HPLC retention time (min.): 2.68; MS: 289 (M+H)$^+$.

EXAMPLE 3(590)

3-(4-Methylpiperazin-1-yl)-N-(1-naphthyl)azetidine-1-carboxamide

HPLC retention time (min.): 2.94; MS: 649 (2M+H)$^+$, 325 (M+H)$^+$.

EXAMPLE 3(591)

3-(4-Methylpiperazin-1-yl)-N-(2-naphthyl)azetidine-1-carboxamide

HPLC retention time (min.): 3.07; MS: 649 (2M+H)$^+$, 325 (M+H)$^+$.

EXAMPLE 3(592)

3-(4-Methylpiperazin-1-yl)-N-[1-(1-naphthyl)ethyl]azetidine-1-carboxamide

HPLC retention time (min.): 3.10; MS: 705 (2M+H)$^+$, 353 (M+H)$^+$.

EXAMPLE 3(593)

N-(3,4-Dimethylphenyl)-3-(4-methylpiperazin-1-yl)azetidine-1-carboxamide

HPLC retention time (min.): 2.99; MS: 605 (2M+H)$^+$, 303 (M+H)$^+$.

EXAMPLE 3(594)

N-(4-Methylphenyl)-3-(4-methylpiperazin-1-yl)azetidine-1-carboxamide

HPLC retention time (min.): 2.90; MS: 577 (2M+H)$^+$, 289 (M+H)$^+$.

EXAMPLE 3(595)

N-Cyclohexyl-3-(4-methylpiperazin-1-yl)azetidine-1-carboxamide

HPLC retention time (min.): 2.81; MS: 561 (2M+H)$^+$, 281 (M+H)$^+$.

EXAMPLE 3(596)

N-(2,6-Dimethylphenyl)-3-(4-methylpiperazin-1-yl)azetidine-1-carboxamide

HPLC retention time (min.): 2.75; MS: 605 (2M+H)$^+$, 303 (M+H)$^+$.

EXAMPLE 3(597)

N-(2-Ethoxyphenyl)-3-(4-methylpiperazin-1-yl)azetidine-1-carboxamide

HPLC retention time (min.): 2.95; MS: 637 (2M+H)$^+$, 319 (M+H)$^+$.

EXAMPLE 3(598)

N-(2-Ethylphenyl)-3-(4-methylpiperazin-1-yl)azetidine-1-carboxamide

HPLC retention time (min.): 2.86; MS: 605 (2M+H)$^+$, 303 (M+H)$^+$.

EXAMPLE 3(599)

N-(4-Ethoxyphenyl)-3-(4-methylpiperazin-1-yl)azetidine-1-carboxamide

HPLC retention time (min.): 2.91; MS: 637 (2M+H)$^+$, 319 (M+H)$^+$.

EXAMPLE 3(600)

3-(4-Methylpiperazin-1-yl)-N-(2-phenylethyl)azetidine-1-carboxamide

HPLC retention time (min.): 2.87; MS: 303 (M+H)$^+$.

EXAMPLE 3(601)

3-(4-Methylpiperazin-1-yl)-N-phenylazetidine-1-carboxamide

HPLC retention time (min.): 2.91(condition B); MS: 549 (2M+H)$^+$, 275 (M+H)$^+$.

EXAMPLE 3(602)

N-(2-Chlorophenyl)-3-(4-methylpiperazin-1-yl)azetidine-1-carboxamide

HPLC retention time (min.): 2.83; MS: 617 (2M+H)$^+$, 311, 309 (M+H)$^+$.

EXAMPLE 3(603)

N-(2-Fluorophenyl)-3-(4-methylpiperazin-1-yl)azetidine-1-carboxamide

HPLC retention time (min.): 2.91(condition B); MS: 585 $(2M+H)^+$, 293 $(M+H)^+$.

EXAMPLE 3(604)

3-(4-Methylpiperazin-1-yl)-N-[3-(trifluoromethyl)phenyl]azetidine-1-carboxamide

HPLC retention time (min.): 3.09; MS: 685 $(2M+H)^+$, 343 $(M+H)^+$.

EXAMPLE 3(605)

N-Cyclopentyl-3-(4-methylpiperazin-1-yl)azetidine-1-carboxamide

HPLC retention time (min.): 2.84(condition B); MS: 267 $(M+H)^+$.

EXAMPLE 3(606)

N-(2,4-Dimethylphenyl)-3-(4-methylpiperazin-1-yl)azetidine-1-carboxamide

HPLC retention time (min.): 2.93; MS: 605 $(2M+H)^+$, 303 $(M+H)^+$.

EXAMPLE 3(607)

N-(3,5-Dichlorophenyl)-3-(4-methylpiperazin-1-yl)azetidine-1-carboxamide

HPLC retention time (min.): 3.17; MS: 687, 685 $(2M+H)^+$, 345, 343 $(M+H)^+$;
TLC:Rf 0.83 (chloroform:methanol:ammonia water=80:20:1);
NMR($CD_3OD$): d 2.30 (s, 3H), 2.32-2.67 (m, 8H), 3.16-3.27 (m, 1H), 3.90 (dd, J=9.15, 5.13 Hz, 2H), 4.06-4.14 (m, 2H), 7.02 (t, J=1.83 Hz, 1H), 7.50 (d, J=1.83 Hz, 2H).

EXAMPLE 3(608)

N-[3,5-Bis(trifluoromethyl)phenyl]-3-(4-methylpiperazin-1-yl)azetidine-1-carboxamide HPLC retention time (min.): 3.34; MS: 821 $(2M+H)^+$, 411 $(M+H)^+$.

EXAMPLE 3(609)

3-(4-Methylpiperazin-1-yl)-N-(3-phenoxyphenyl)azetidine-1-carboxamide

HPLC retention time (min.): 3.21; MS: 733 $(2M+H)^+$, 367 $(M+H)^+$.

EXAMPLE 3(610)

N-(3,5-Difluorophenyl)-3-(4-methylpiperazin-1-yl)azetidine-1-carboxamide

HPLC retention time (min.): 2.98; MS: 621 $(2M+H)^+$, 311 $(M+H)^+$.

EXAMPLE 3(611)

N-(4-Methoxyphenyl)-3-(4-methylpiperazin-1-yl)azetidine-1-carboxamide

HPLC retention time (min.): 2.92(condition B); MS: 609 $(2M+H)^+$, 305 $(M+H)^+$.

EXAMPLE 3(612)

N-(3,5-Dimethylphenyl)-3-(4-methylpiperazin-1-yl)azetidine-1-carboxamide

HPLC retention time (min.): 3.02; MS: 605 $(2M+H)^+$, 303 $(M+H)^+$.

EXAMPLE 3(613)

N-(3-Fluorophenyl)-3-(4-methylpiperazin-1-yl)azetidine-1-carboxamide

HPLC retention time (min.): 2.86; MS: 585 $(2M+H)^+$, 293 $(M+H)^+$.

EXAMPLE 3(614)

Methyl 3-({[3-(4-methylpiperazin-1-yl)azetidin-1-yl]carbonyl}amino)benzoate

HPLC retention time (min.): 2.90; MS: 665 $(2M+H)^+$, 333 $(M+H)^+$.

EXAMPLE 3(615)

3-(4-Methylpiperazin-1-yl)-N-[3-(methylsulfanyl)phenyl]azetidine-1-carboxamide

HPLC retention time (min.): 2.98; MS: 641 $(2M+H)^+$, 321 $(M+H)^+$.

EXAMPLE 3(616)

N-Ethyl-3-(4-phenylpiperazin-1-yl)azetidine-1-carboxamide

HPLC retention time (min.): 2.83; MS: 289 $(M+H)^+$.

EXAMPLE 3(617)

3-(4-Phenylpiperazin-1-yl)-N-propylazetidine-1-carboxamide

HPLC retention time (min.): 2.93; MS: 303 $(M+H)^+$.

EXAMPLE 3(618)

Ethyl N-{[3-(4-phenylpiperazin-1-yl)azetidin-1-yl]carbonyl}glycinate

HPLC retention time (min.): 2.92; MS: 347 $(M+H)^+$.

EXAMPLE 3(619)

N-Hexyl-3-(4-phenylpiperazin-1-yl)azetidine-1-carboxamide

HPLC retention time (min.): 3.26; MS: 345 $(M+H)^+$.

EXAMPLE 3(620)

N-(4-Fluorophenyl)-3-(4-phenylpiperazin-1-yl)azetidine-1-carboxamide

HPLC retention time (min.): 3.14; MS: 355 (M+H)$^+$.

EXAMPLE 3(621)

N-(3-Methylphenyl)-3-(4-phenylpiperazin-1-yl)azetidine-1-carboxamide

HPLC retention time (min.): 3.18; MS: 701 (2M+H)$^+$, 351 (M+H)$^+$.

EXAMPLE 3(622)

3-(4-Phenylpiperazin-1-yl)-N-(2-thien-2-ylethyl)azetidine-1-carboxamide

HPLC retention time (min.): 3.13; MS: 371 (M+H)$^+$.

EXAMPLE 3(623)

N-(4-Isopropylphenyl)-3-(4-phenylpiperazin-1-yl)azetidine-1-carboxamide

HPLC retention time (min.): 3.36; MS: 757 (2M+H)$^+$, 379 (M+H)$^+$.

EXAMPLE 3(624)

N-(3-Chlorophenyl)-3-(4-phenylpiperazin-1-yl)azetidine-1-carboxamide

HPLC retention time (min.): 3.25; MS: 741 (2M+H)$^+$, 373, 371 (M+H)$^+$.

EXAMPLE 3(625)

N-(2,5-Dimethylphenyl)-3-(4-phenylpiperazin-1-yl)azetidine-1-carboxamide

HPLC retention time (min.): 3.18; MS: 729 (2M+H)$^+$, 365 (M+H)$^+$.

EXAMPLE 3(626)

N-(4-Chlorophenyl)-3-(4-phenylpiperazin-1-yl)azetidine-1-carboxamide

HPLC retention time (min.): 3.23; MS: 741 (2M+H)$^+$, 373, 371 (M+H)$^+$.

EXAMPLE 3(627)

N-Benzyl-3-(4-phenylpiperazin-1-yl)azetidine-1-carboxamide

HPLC retention time (min.): 3.10; MS: 351 (M+H)$^+$.

EXAMPLE 3(628)

N-(1-Naphthyl)-3-(4-phenylpiperazin-1-yl)azetidine-1-carboxamide

HPLC retention time (min.): 3.21; MS: 773 (2M+H)$^+$, 387 (M+H)$^+$.

EXAMPLE 3(629)

N-(2-Naphthyl)-3-(4-phenylpiperazin-1-yl)azetidine-1-carboxamide

HPLC retention time (min.): 3.29; MS: 773 (2M+H)$^+$, 387 (M+H)$^+$.

EXAMPLE 3(630)

N-[1-(1-Naphthyl)ethyl]-3-(4-phenylpiperazin-1-yl)azetidine-1-carboxamide

HPLC retention time (min.): 3.33; MS: 829 (2M+H)$^+$, 415 (M+H)$^+$.

EXAMPLE 3(631)

N-(3,4-Dimethylphenyl)-3-(4-phenylpiperazin-1-yl)azetidine-1-carboxamide

HPLC retention time (min.): 3.25; MS: 729 (2M+H)$^+$, 365 (M+H)$^+$.

EXAMPLE 3(632)

N-(4-Methylphenyl)-3-(4-phenylpiperazin-1-yl)azetidine-1-carboxamide

HPLC retention time (min.): 3.18; MS: 701 (2M+H)$^+$, 351 (M+H)$^+$.

EXAMPLE 3(633)

N-Cyclohexyl-3-(4-phenylpiperazin-1-yl)azetidine-1-carboxamide

HPLC retention time (min.): 3.13; MS: 343 (M+H)$^+$.

EXAMPLE 3(634)

N-(2,6-Dimethylphenyl)-3-(4-phenylpiperazin-1-yl)azetidine-1-carboxamide

HPLC retention time (min.): 3.13; MS: 729 (2M+H)$^+$, 365 (M+H)$^+$.

EXAMPLE 3(635)

N-(2-Ethoxyphenyl)-3-(4-phenylpiperazin-1-yl)azetidine-1-carboxamide

HPLC retention time (min.): 3.21; MS: 761 (2M+H)$^+$, 381 (M+H)$^+$.

EXAMPLE 3(636)

N-(2-Ethylphenyl)-3-(4-phenylpiperazin-1-yl)azetidine-1-carboxamide

HPLC retention time (min.): 3.16; MS: 729 (2M+H) +, 365 (M+H)$^+$.

EXAMPLE 3(637)

N-(4-Ethoxyphenyl)-3-(4-phenylpiperazin-1-yl)azetidine-1-carboxamide

HPLC retention time (min.): 3.18; MS: 761 (2M+H)$^+$, 381 (M+H)$^+$.

EXAMPLE 3(638)

N-(2-Phenylethyl)-3-(4-phenylpiperazin-1-yl)azetidine-1-carboxamide

HPLC retention time (min.): 3.16; MS: 365 (M+H)$^+$.

EXAMPLE 3(639)

N-Phenyl-3-(4-phenylpiperazin-1-yl)azetidine-1-carboxamide

HPLC retention time (min.): 3.09; MS: 673 (2M+H)$^+$, 337 (M+H)$^+$.

EXAMPLE 3(640)

N-(2-Chlorophenyl)-3-(4-phenylpiperazin-1-yl)azetidine-1-carboxamide

HPLC retention time (min.): 3.14; MS: 741 (2M+H)$^+$, 373, 371 (M+H)$^+$.

EXAMPLE 3(641)

N-(2-Fluorophenyl)-3-(4-phenylpiperazin-1-yl)azetidine-1-carboxamide

HPLC retention time (min.): 3.08; MS: 709 (2M+H)$^+$, 355 (M+H)$^+$.

EXAMPLE 3(642)

3-(4-Phenylpiperazin-1-yl)-N-[3-(trifluoromethyl)phenyl]azetidine-1-carboxamide

HPLC retention time (min.): 3.34; MS: 809 (2M+H)$^+$, 405 (M+H)$^+$.

EXAMPLE 3(643)

N-Cyclopentyl-3-(4-phenylpiperazin-1-yl)azetidine-1-carboxamide

HPLC retention time (min.): 3.05; MS: 329 (M+H)$^+$.

EXAMPLE 3(644)

N-(2,4-Dimethylphenyl)-3-(4-phenylpiperazin-1-yl)azetidine-1-carboxamide

HPLC retention time (min.): 3.18; MS: 729 (2M+H)$^+$, 365 (M+H)$^+$.

EXAMPLE 3(645)

N-(3,5-Dichlorophenyl)-3-(4-phenylpiperazin-1-yl)azetidine-1-carboxamide

HPLC retention time (min.): 3.40; MS: 811, 809 (2M+H)$^+$, 407, 405 (M+H)$^+$.

EXAMPLE 3(646)

N-[3,5-Bis(trifluoromethyl)phenyl]-3-(4-phenylpiperazin-1-yl)azetidine-1-carboxamide HPLC retention time (min.): 3.54; MS: 945 (2M+H)$^+$, 473 (M+H)$^+$.

EXAMPLE 3(647)

N-(3-Phenoxyphenyl)-3-(4-phenylpiperazin-1-yl)azetidine-1-carboxamide

HPLC retention time (min.): 3.43; MS: 857 (2M+H)$^+$, 429 (M+H)$^+$.

EXAMPLE 3(648)

N-(3,5-Difluorophenyl)-3-(4-phenylpiperazin-1-yl)azetidine-1-carboxamide

HPLC retention time (min.): 3.23; MS: 745 (2M+H)$^+$, 373 (M+H)$^+$.

EXAMPLE 3(649)

N-(4-Methoxyphenyl)-3-(4-phenylpiperazin-1-yl)azetidine-1-carboxamide

HPLC retention time (min.): 3.09; MS: 733 (2M+H)$^+$, 367 (M+H)$^+$.

EXAMPLE 3(650)

N-(3,5-Dimethylphenyl)-3-(4-phenylpiperazin-1-yl)azetidine-1-carboxamide

HPLC retention time (min.): 3.26; MS: 729 (2M+H)$^+$, 365 (M+H)$^+$.

EXAMPLE 3(651)

N-(3-Fluorophenyl)-3-(4-phenylpiperazin-1-yl)azetidine-1-carboxamide

HPLC retention time (min.): 3.17; MS: 709 (2M+H)$^+$, 355 (M+H)$^+$.

EXAMPLE 3(652)

Methyl 3-({[3-(4-phenylpiperazin-1-yl)azetidin-1-yl]carbonyl}amino)benzoate

HPLC retention time (min.): 3.16; MS: 789 (2M+H)$^+$, 395 (M+H)$^+$.

EXAMPLE 3(653)

N-[3-(Methylsulfanyl)phenyl]-3-(4-phenylpiperazin-1-yl)azetidine-1-carboxamide

HPLC retention time (min.): 3.23; MS: 765 (2M+H)$^+$, 383 (M+H)$^+$.

EXAMPLE 3(654)

N-(2-methylphenyl)-3-(4-phenylpiperazin-1-yl)azetidine-1-carboxamide

HPLC retention time (min.): 3.11; MS: 701 (2M+H)$^+$, 351 (M+H)$^+$.

EXAMPLE 3(655)

N-Ethyl-3-(4-phenylpiperidin-1-yl)azetidine-1-carboxamide

HPLC retention time (min.): 2.99; MS: 288 (M+H)$^+$, 279.

EXAMPLE 3(656)

3-(4-phenylpiperidin-1-yl)-N-propylazetidine-1-carboxamide

HPLC retention time (min.): 3.01; MS: 302 (M+H)$^+$.

EXAMPLE 3(657)

Ethyl N-{[3-(4-phenylpiperidin-1-yl)azetidin-1-yl]carbonyl})glycinate

HPLC retention time (min.): 2.99; MS: 346 (M+H)$^+$.

EXAMPLE 3(658)

N-Hexyl-3-(4-phenylpiperidin-1-yl)azetidine-1-carboxamide

HPLC retention time (min.): 3.31; MS: 687 (2M+H)$^+$, 344 (M+H)$^+$.

EXAMPLE 3(659)

N-(4-Fluorophenyl)-3-(4-phenylpiperidin-1-yl)azetidine-1-carboxamide

HPLC retention time (min.): 3.19; MS: 707 (2M+H)$^+$, 354 (M+H)$^+$.

EXAMPLE 3(660)

N-(3-Methylphenyl)-3-(4-phenylpiperidin-1-yl)azetidine-1-carboxamide

HPLC retention time (min.): 3.23; MS: 699 (2M+H)$^+$, 350 (M+H)$^+$.

EXAMPLE 3(661)

3-(4-Phenylpiperidin-1-yl)-N-(2-thien-2-ylethyl)azetidine-1-carboxamide

HPLC retention time (min.): 3.18; MS: 739 (2M+H)$^+$, 370 (M+H)$^+$.

EXAMPLE 3(662)

N-(4-Isopropylphenyl)-3-(4-phenylpiperidin-1-yl)azetidine-1-carboxamide

HPLC retention time (min.): 3.42; MS: 755 (2M+H)$^+$, 378 (M+H)$^+$.

EXAMPLE 3(663)

N-(3-Chlorophenyl)-3-(4-phenylpiperidin-1-yl)azetidine-1-carboxamide

HPLC retention time (min.): 3.29; MS: 739 (2M+H)$^+$, 372, 370 (M+H)$^+$.

EXAMPLE 3(664)

N-(2,5-Dimethylphenyl)-3-(4-phenylpiperidin-1-yl)azetidine-1-carboxamide

HPLC retention time (min.): 3.24; MS: 727 (2M+H)$^+$, 364 (M+H)$^+$.

EXAMPLE 3(665)

N-(4-Chlorophenyl)-3-(4-phenylpiperidin-1-yl)azetidine-1-carboxamide

HPLC retention time (min.): 3.29; MS: 739 (2M+H)$^+$, 372, 370 (M+H)$^+$.

EXAMPLE 3(666)

N-Benzyl-3-(4-phenylpiperidin-1-yl)azetidine-1-carboxamide

HPLC retention time (min.): 3.16; MS: 699 (2M+H)$^+$, 350 (M+H)$^+$.

EXAMPLE 3(667)

N-(1-Naphthyl)-3-(4-phenylpiperidin-1-yl)azetidine-1-carboxamide

HPLC retention time (min.): 3.27; MS: 771 (2M+H)$^+$, 386 (M+H)$^+$.

EXAMPLE 3(668)

N-(2-Naphthyl)-3-(4-phenylpiperidin-1-yl)azetidine-1-carboxamide

HPLC retention time (min.): 3.35; MS: 771 (2M+H)$^+$, 386 (M+H)$^+$.

EXAMPLE 3(669)

N-[1-(1-Naphthyl)ethyl]-3-(4-phenylpiperidin-1-yl)azetidine-1-carboxamide

HPLC retention time (min.): 3.38; MS: 827 (2M+H)$^+$, 414 (M+H)$^+$.

EXAMPLE 3(670)

N-(3,4-Dimethylphenyl)-3-(4-phenylpiperidin-1-yl)azetidine-1-carboxamide

HPLC retention time (min.): 3.30; MS: 727 (2M+H)$^+$, 364 (M+H)$^+$.

EXAMPLE 3(671)

N-(4-Methylphenyl)-3-(4-phenylpiperidin-1-yl)azetidine-1-carboxamide

HPLC retention time (min.): 3.23; MS: 699 (2M+H)$^+$, 350 (M+H)$^+$.

EXAMPLE 3(672)

N-Cyclohexyl-3-(4-phenylpiperidin-1-yl)azetidine-1-carboxamide

HPLC retention time (min.): 3.18; MS: 683 (2M+H)$^+$, 342 (M+H)$^+$;
TLC:Rf 0.71 (chloroform:methanol=9:1);
NMR(CD$_3$OD): δ 7.29-7.10 (m, 5H), 3.97 (br t, J=8.4 Hz, 2H), 3.84-3.76 (m, 2H), 3.54-3.38 (m, 1H), 3.22-3.10 (m, 1H), 3.02-2.92 (m, 2H), 2.61-2.48 (m, 1H), 2.08-1.98 (m, 2H), 1.88-1.54 (m, 9H), 1.42-1.10 (m, 5H).

EXAMPLE 3(673)

N-(2,6-Dimethylphenyl)-3-(4-phenylpiperidin-1-yl)azetidine-1-carboxamide

HPLC retention time (min.): 3.18; MS: 727 (2M+H)$^+$, 364 (M+H)$^+$.

EXAMPLE 3(674)

N-(2-Ethoxyphenyl)-3-(4-phenylpiperidin-1-yl)azetidine-1-carboxamide

HPLC retention time (min.): 3.28; MS: 759 (2M+H)$^+$, 380 (M+H)$^+$.

EXAMPLE 3(675)

N-(2-Ethylphenyl)-3-(4-phenylpiperidin-1-yl)azetidine-1-carboxamide

HPLC retention time (min.): 3.23; MS: 727 (2M+H)$^+$, 364 (M+H)$^+$.

EXAMPLE 3(676)

N-(4-Ethoxyphenyl)-3-(4-phenylpiperidin-1-yl)azetidine-1-carboxamide

HPLC retention time (min.): 3.23; MS: 759 (2M+H)$^+$, 380 (M+H)$^+$.

EXAMPLE 3(677)

N-(2-Phenylethyl)-3-(4-phenylpiperidin-1-yl)azetidine-1-carboxamide

HPLC retention time (min.): 3.22; MS: 727 (2M+H)$^+$, 364 (M+H)$^+$.

EXAMPLE 3(678)

N-Phenyl-3-(4-phenylpiperidin-1-yl)azetidine-1-carboxamide

HPLC retention time (min.): 3.15; MS: 671 (2M+H)$^+$, 336 (M+H)$^+$.

EXAMPLE 3(679)

N-(2-Chlorophenyl)-3-(4-phenylpiperidin-1-yl)azetidine-1-carboxamide

HPLC retention time (min.): 3.19; MS: 739 (2M+H)$^+$, 372, 370 (M+H)$^+$.

EXAMPLE 3(680)

N-(2-Fluorophenyl)-3-(4-phenylpiperidin-1-yl)azetidine-1-carboxamide

HPLC retention time (min.): 3.15; MS: 707 (2M+H)$^+$, 354 (M+H)$^+$.

EXAMPLE 3(681)

3-(4-Phenylpiperidin-1-yl)-N-[3-(trifluoromethyl)phenyl]azetidine-1-carboxamide

HPLC retention time (min.): 3.37; MS: 807 (2M+H)$^+$, 404 (M+H)$^+$.

EXAMPLE 3(682)

N-Cyclopentyl-3-(4-phenylpiperidin-1-yl)azetidine-1-carboxamide

HPLC retention time (min.): 3.11; MS: 328 (M+H)$^+$.

EXAMPLE 3(683)

N-(2,4-Dimethylphenyl)-3-(4-phenylpiperidin-1-yl)azetidine-1-carboxamide

HPLC retention time (min.): 3.24; MS: 727 (2M+H)$^+$, 364 (M+H)$^+$.

EXAMPLE 3(684)

N-(3,5-Dichlorophenyl)-3-(4-phenylpiperidin-1-yl)azetidine-1-carboxamide

HPLC retention time (min.): 3.45; MS: 809, 807 (2M+H)$^+$, 406, 404 (M+H)$^+$.

EXAMPLE 3(685)

N-[3,5-Bis(trifluoromethyl)phenyl]-3-(4-phenylpiperidin-1-yl)azetidine-1-carboxamide HPLC retention time (min.): 3.58; MS: 943 (2M+H)$^+$, 472 (M+H)$^+$.

EXAMPLE 3(686)

N-(3-Phenoxyphenyl)-3-(4-phenylpiperidin-1-yl)azetidine-1-carboxamide

HPLC retention time (min.): 3.46; MS: 855 (2M+H)$^+$, 428 (M+H)$^+$.

EXAMPLE 3(687)

N-(3,5-Difluorophenyl)-3-(4-phenylpiperidin-1-yl)azetidine-1-carboxamide

HPLC retention time (min.): 3.30; MS: 743 (2M+H)$^+$, 372 (M+H)$^+$.

EXAMPLE 3(688)

N-(4-Methoxyphenyl)-3-(4-phenylpiperidin-1-yl)azetidine-1-carboxamide

HPLC retention time (min.): 3.15; MS: 731 (2M+H)$^+$, 366 (M+H)$^+$.

EXAMPLE 3(689)

N-(3,5-Dimethylphenyl)-3-(4-phenylpiperidin-1-yl)azetidine-1-carboxamide

HPLC retention time (min.): 3.31; MS: 727 (2M+H)$^+$, 364 (M+H)$^+$.

EXAMPLE 3(690)

N-(3-Fluorophenyl)-3-(4-phenylpiperidin-1-yl)azetidine-1-carboxamide

HPLC retention time (min.): 3.22; MS: 707 (2M+H)$^+$, 354 (M+H)$^+$.

EXAMPLE 3(691)

Methyl 3-({[3-(4-phenylpiperidin-1-yl)azetidin-1-yl]carbonyl}amino)benzoate

HPLC retention time (min.): 3.20; MS: 787 (2M+H)$^+$, 394 (M+H)$^+$.

EXAMPLE 3(692)

N-[3-(Methylsulfanyl)phenyl]-3-(4-phenylpiperidin-1-yl)azetidine-1-carboxamide

HPLC retention time (min.): 3.28; MS: 763 (2M+H)$^+$, 382 (M+H)$^+$.

EXAMPLE 3(693)

N-(2-Methylphenyl)-3-(4-phenylpiperidin-1-yl)azetidine-1-carboxamide

HPLC retention time (min.): 3.16; MS: 699 (2M+H)$^+$, 350 (M+H)$^+$.

EXAMPLE 3(694)

3-(4-benzylpiperidin-1-yl)-N-ethylazetidine-1-carboxamide

HPLC retention time (min.): 3.04; MS: 302 (M+H)$^+$, 293.

EXAMPLE 3(695)

3-(4-Benzylpiperidin-1-yl)-N-propylazetidine-1-carboxamide

HPLC retention time (min.): 3.09; MS: 316 (M+H)$^+$.

EXAMPLE 3(696)

Ethyl N-{[3-(4-benzylpiperidin-1-yl)azetidin-1-yl]carbonyl}glycinate

HPLC retention time (min.): 3.09; MS: 360 (M+H)$^+$.

EXAMPLE 3(697)

3-(4-Benzylpiperidin-1-yl)-N-hexylazetidine-1-carboxamide

HPLC retention time (min.): 3.37; MS: 715 (2M+H)$^+$, 358 (M+H)$^+$.

EXAMPLE 3(698)

3-(4-Benzylpiperidin-1-yl)-N-(4-fluorophenyl)azetidine-1-carboxamide

HPLC retention time (min.): 3.27; MS: 735 (2M+H)$^+$, 368 (M+H)$^+$.

EXAMPLE 3(699)

3-(4-Benzylpiperidin-1-yl)-N-(3-methylphenyl)azetidine-1-carboxamide

HPLC retention time (min.): 3.30; MS: 727 (2M+H)$^+$, 364 (M+H)$^+$.

EXAMPLE 3(700)

3-(4-Benzylpiperidin-1-yl)-N-(2-thien-2-ylethyl)azetidine-1-carboxamide

HPLC retention time (min.): 3.26; MS: 767 (2M+H)$^+$, 384 (M+H)$^+$.

EXAMPLE 3(701)

3-(4-Benzylpiperidin-1-yl)-N-(4-isopropylphenyl)azetidine-1-carboxamide

HPLC retention time (min.): 3.46; MS: 783 (2M+H)$^+$, 392 (M+H)$^+$.

EXAMPLE 3(702)

3-(4-Benzylpiperidin-1-yl)-N-(3-chlorophenyl)azetidine-1-carboxamide

HPLC retention time (min.): 3.38; MS: 767 (2M+H)$^+$, 386, 384 (M+H)$^+$.

EXAMPLE 3(703)

3-(4-Benzylpiperidin-1-yl)-N-(2,5-dimethylphenyl)azetidine-1-carboxamide

HPLC retention time (min.): 3.32; MS: 755 (2M+H)$^+$, 378 (M+H)$^+$.

EXAMPLE 3(704)

3-(4-Benzylpiperidin-1-yl)-N-(4-chlorophenyl)azetidine-1-carboxamide

HPLC retention time (min.): 3.35; MS: 767 (2M+H)$^+$, 386, 384 (M+H)$^+$.

EXAMPLE 3(705)

N-Benzyl-3-(4-benzylpiperidin-1-yl)azetidine-1-carboxamide

HPLC retention time (min.): 3.24; MS: 727 (2M+H)$^+$, 364 (M+H)$^+$.

EXAMPLE 3(706)

3-(4-Benzylpiperidin-1-yl)-N-(1-naphthyl)azetidine-1-carboxamide

HPLC retention time (min.): 3.32; MS: 799 (2M+H)$^+$, 400 (M+H)$^+$.

EXAMPLE 3(707)

3-(4-Benzylpiperidin-1-yl)-N-(2-naphthyl)azetidine-1-carboxamide

HPLC retention time (min.): 3.40; MS: 799 (2M+H)$^+$, 400 (M+H)$^+$.

EXAMPLE 3(708)

3-(4-Benzylpiperidin-1-yl)-N-[1-(1-naphthyl)ethyl]azetidine-1-carboxamide

HPLC retention time (min.): 3.43; MS: 855 (2M+H)$^+$, 428 (M+H)$^+$.

EXAMPLE 3(709)

3-(4-Benzylpiperidin-1-yl)-N-(3,4-dimethylphenyl)azetidine-1-carboxamide

HPLC retention time (min.): 3.36; MS: 755 (2M+H)$^+$, 378 (M+H)$^+$.

EXAMPLE 3(710)

3-(4-Benzylpiperidin-1-yl)-N-(4-methylphenyl)azetidine-1-carboxamide

HPLC retention time (min.): 3.31; MS: 727 (2M+H)$^+$, 364 (M+H)$^+$.

EXAMPLE 3(711)

3-(4-Benzylpiperidin-1-yl)-N-cyclohexylazetidine-1-carboxamide

HPLC retention time (min.): 3.25; MS: 711 (2M+H)$^+$, 356 (M+H)$^+$.

EXAMPLE 3(712)

3-(4-Benzylpiperidin-1-yl)-N-(2,6-dimethylphenyl)azetidine-1-carboxamide

HPLC retention time (min.): 3.26; MS: 755 (2M+H)$^+$, 378 (M+H)$^+$.

EXAMPLE 3(713)

3-(4-Benzylpiperidin-1-yl)-N-(2-ethoxyphenyl)azetidine-1-carboxamide

HPLC retention time (min.): 3.34; MS: 787 (2M+H)$^+$, 394 (M+H)$^+$.

EXAMPLE 3(714)

3-(4-Benzylpiperidin-1-yl)-N-(2-ethylphenyl)azetidine-1-carboxamide

HPLC retention time (min.): 3.31; MS: 755 (2M+H)$^+$, 378 (M+H)$^+$.

EXAMPLE 3(715)

3-(4-Benzylpiperidin-1-yl)-N-(4-ethoxyphenyl)azetidine-1-carboxamide

HPLC retention time (min.): 3.30; MS: 787 (2M+H)$^+$, 394 (M+H)$^+$.

EXAMPLE 3(716)

3-(4-Benzylpiperidin-1-yl)-N-(2-phenylethyl)azetidine-1-carboxamide

HPLC retention time (min.): 3.30; MS: 755 (2M+H)$^+$, 378 (M+H)$^+$.

EXAMPLE 3(717)

3-(4-Benzylpiperidin-1-yl)-N-phenylazetidine-1-carboxamide

HPLC retention time (min.): 3.23; MS: 699 (2M+H)$^+$, 350 (M+H)$^+$.

EXAMPLE 3(718)

3-(4-Benzylpiperidin-1-yl)-N-(2-chlorophenyl)azetidine-1-carboxamide

HPLC retention time (min.): 3.28; MS: 767 (2M+H)$^+$, 386, 384 (M+H)$^+$.

EXAMPLE 3(719)

3-(4-Benzylpiperidin-1-yl)-N-(2-fluorophenyl)azetidine-1-carboxamide

HPLC retention time (min.): 3.24; MS: 735 (2M+H), 368 (M+H)$^+$.

EXAMPLE 3(720)

3-(4-Benzylpiperidin-1-yl)-N-[3-(trifluoromethyl)phenyl]azetidine-1-carboxamide

HPLC retention time (min.): 3.45; MS: 835 (2M+H)$^+$, 418 (M+H)$^+$.

EXAMPLE 3(721)

3-(4-Benzylpiperidin-1-yl)-N-cyclopentylazetidine-1-carboxamide

HPLC retention time (min.): 3.19; MS: 683 (2M+H)$^+$, 342 (M+H)$^+$.

EXAMPLE 3(722)

3-(4-Benzylpiperidin-1-yl)-N-(2,4-dimethylphenyl)azetidine-1-carboxamide

HPLC retention time (min.): 3.31; MS: 755 (2M+H)$^+$, 378 (M+H)$^+$.

EXAMPLE 3(723)

3-(4-Benzylpiperidin-1-yl)-N-(3,5-dichlorophenyl)azetidine-1-carboxamide

HPLC retention time (min.): 3.49; MS: 837, 835 $(2M+H)^+$, 420, 418 $(M+H)^+$.

EXAMPLE 3(724)

3-(4-Benzylpiperidin-1-yl)-N-[3,5-bis(trifluoromethyl)phenyl]azetidine-1-carboxamide HPLC retention time (min.): 3.63; MS: 971 $(2M+H)^+$, 486 $(M+H)^+$.

EXAMPLE 3(725)

3-(4-Benzylpiperidin-1-yl)-N-(3-phenoxyphenyl)azetidine-1-carboxamide

HPLC retention time (min.): 3.53; MS: 883 $(2M+H)^+$, 442 $(M+H)^+$.

EXAMPLE 3(726)

3-(4-Benzylpiperidin-1-yl)-N-(3,5-difluorophenyl)azetidine-1-carboxamide

HPLC retention time (min.): 3.35; MS: 771 $(2M+H)^+$, 386 $(M+H)^+$.

EXAMPLE 3(727)

3-(4-Benzylpiperidin-1-yl)-N-(4-methoxyphenyl)azetidine-1-carboxamide

HPLC retention time (min.): 3.22; MS: 759 $(2M+H)^+$, 380 $(M+H)^+$.

EXAMPLE 3(728)

3-(4-Benzylpiperidin-1-yl)-N-(3,5-dimethylphenyl)azetidine-1-carboxamide

HPLC retention time (min.): 3.37; MS: 755 $(2M+H)^+$, 378 $(M+H)^+$.

EXAMPLE 3(729)

3-(4-Benzylpiperidin-1-yl)-N-(3-fluorophenyl)azetidine-1-carboxamide

HPLC retention time (min.): 3.29; MS: 735 $(2M+H)^+$, 368 $(M+H)^+$.

EXAMPLE 3(730)

Methyl 3-({[3-(4-benzylpiperidin-1-yl)azetidin-1-yl]carbonyl}amino)benzoate

HPLC retention time (min.): 3.28; MS: 815 $(2M+H)^+$, 408 $(M+H)^+$.

EXAMPLE 3(731)

3-(4-Benzylpiperidin-1-yl)-N-[3-(methylsulfanyl)phenyl]azetidine-1-carboxamide

HPLC retention time (min.): 3.35; MS: 791 $(2M+H)^+$, 396 $(M+H)^+$.

EXAMPLE 3(732)

3-(4-Benzylpiperidin-1-yl)-N-(2-methylphenyl)azetidine-1-carboxamide

HPLC retention time (min.): 3.23; MS: 727 $(2M+H)^+$, 364 $(M+H)^+$.

EXAMPLE 3(733)

3-(2,3-Dihydro-1H-indol-1-yl)-N-ethylazetidine-1-carboxamide

HPLC retention time (min.): 3.22; MS: 246 $(M+H)^+$.

EXAMPLE 3(734)

3-(2,3-Dihydro-1H-indol-1-yl)-N-propylazetidine-1-carboxamide

HPLC retention time (min.): 3.37; MS: 260 $(M+H)^+$.

EXAMPLE 3(735)

Ethyl N-{[3-(2,3-dihydro-1H-indol-1-yl)azetidin-1-yl]carbonyl}glycinate

HPLC retention time (min.): 3.29; MS: 304 $(M+H)^+$.

EXAMPLE 3(736)

3-(2,3-Dihydro-1H-indol-1-yl)-N-hexylazetidine-1-carboxamide

HPLC retention time (min.): 3.82; MS: 603 $(2M+H)^+$, 302 $(M+H)^+$.

EXAMPLE 3(737)

3-(2,3-Dihydro-1H-indol-1-yl)-N-(4-fluorophenyl)azetidine-1-carboxamide

HPLC retention time (min.): 3.66; MS: 312 $(M+H)^+$.

EXAMPLE 3(738)

3-(2,3-Dihydro-1H-indol-1-yl)-N-(3-methylphenyl)azetidine-1-carboxamide

HPLC retention time (min.): 3.73; MS: 615 $(2M+H)^+$, 308 $(M+H)^+$.

EXAMPLE 3(739)

3-(2,3-Dihydro-1H-indol-1-yl)-N-(2-thien-2-ylethyl)azetidine-1-carboxamide

HPLC retention time (min.): 3.61; MS: 655 $(2M+H)^+$, 328 $(M+H)^+$.

EXAMPLE 3(740)

3-(2,3-Dihydro-1H-indol-1-yl)-N-(4-isopropylphenyl)azetidine-1-carboxamide

HPLC retention time (min.): 3.93; MS: 671 $(2M+H)^+$, 336 $(M+H)^+$.

EXAMPLE 3(741)

N-(3-Chlorophenyl)-3-(2,3-dihydro-1H-indol-1-yl)azetidine-1-carboxamide

HPLC retention time (min.): 3.82; MS: 655 (2M+H)$^+$, 328 (M+H)$^+$.

EXAMPLE 3(742)

3-(2,3-Dihydro-1H-indol-1-yl)-N-(2,5-dimethylphenyl)azetidine-1-carboxamide

HPLC retention time (min.): 3.76; MS: 643 (2M+H)$^+$, 322 (M+H)$^+$.

EXAMPLE 3(743)

N-(4-Chlorophenyl)-3-(2,3-dihydro-1H-indol-1-yl)azetidine-1-carboxamide

HPLC retention time (min.): 3.81; MS: 655 (2M+H)$^+$, 330, 328 (M+H)$^+$.

EXAMPLE 3(744)

N-Benzyl-3-(2,3-dihydro-1H-indol-1-yl)azetidine-1-carboxamide

HPLC retention time (min.): 3.58; MS: 615 (2M+H)$^+$, 308 (M+H)$^+$.

EXAMPLE 3(745)

3-(2,3-Dihydro-1H-indol-1-yl)-N-(1-naphthyl)azetidine-1-carboxamide

HPLC retention time (min.): 3.76; MS: 687 (2M+H)$^+$, 344 (M+H)$^+$.

EXAMPLE 3(746)

3-(2,3-Dihydro-1H-indol-1-yl)-N-(2-naphthyl)azetidine-1-carboxamide

HPLC retention time (min.): 3.86; MS: 687 (2M+H)$^+$, 344 (M+H)$^+$.

EXAMPLE 3(747)

3-(2,3-Dihydro-1H-indol-1-yl)-N-[1-(1-naphthyl)ethyl]azetidine-1-carboxamide

HPLC retention time (min.): 3.87; MS: 743 (2M+H)$^+$, 372 (M+H)$^+$, 218.

EXAMPLE 3(748)

3-(2,3-Dihydro-1H-indol-1-yl)-N-(3,4-dimethylphenyl)azetidine-1-carboxamide

HPLC retention time (min.): 3.80; MS: 643 (2M+H)$^+$, 322 (M+H)$^+$.

EXAMPLE 3(749)

3-(2,3-Dihydro-1H-indol-1-yl)-N-(4-methylphenyl)azetidine-1-carboxamide

HPLC retention time (min.): 3.73; MS: 615 (2M+H)$^+$, 308 (M+H)$^+$.

EXAMPLE 3(750)

N-Cyclohexyl-3-(2,3-dihydro-1H-indol-1-yl)azetidine-1-carboxamide

HPLC retention time (min.): 3.66; MS: 599 (2M+H)$^+$, 300 (M+H)$^+$.

EXAMPLE 3(751)

3-(2,3-Dihydro-1H-indol-1-yl)-N-(2,6-dimethylphenyl)azetidine-1-carboxamide

HPLC retention time (min.): 3.65; MS: 643 (2M+H)$^+$, 322 (M+H)$^+$.

EXAMPLE 3(752)

3-(2,3-Dihydro-1H-indol-1-yl)-N-(2-ethoxyphenyl)azetidine-1-carboxamide

HPLC retention time (min.): 3.90; MS: 675 (2M+H)$^+$, 338 (M+H)$^+$.

EXAMPLE 3(753)

3-(2,3-Dihydro-1H-indol-1-yl)-N-(2-ethylphenyl)azetidine-1-carboxamide

HPLC retention time (min.): 3.74; MS: 643 (2M+H)$^+$, 322 (M+H)$^+$.

EXAMPLE 3(754)

3-(2,3-Dihydro-1H-indol-1-yl)-N-(4-ethoxyphenyl)azetidine-1-carboxamide

HPLC retention time (min.): 3.68; MS: 675 (2M+H)$^+$, 338 (M+H)$^+$.

EXAMPLE 3(755)

3-(2,3-Dihydro-1H-indol-1-yl)-N-(2-phenylethyl)azetidine-1-carboxamide

HPLC retention time (min.): 3.65; MS: 643 (2M+H)$^+$, 322 (M+H)$^+$.

EXAMPLE 3(756)

3-(2,3-Dihydro-1H-indol-1-yl)-N-phenylazetidine-1-carboxamide

HPLC retention time (min.): 3.61; MS: 294 (M+H)$^+$.

EXAMPLE 3(757)

N-(2-Chlorophenyl)-3-(2,3-dihydro-1H-indol-1-yl)azetidine-1-carboxamide

HPLC retention time (min.): 3.82; MS: 655 (2M+H)$^+$, 330, 328 (M+H)$^+$.

EXAMPLE 3(758)

3-(2,3-Dihydro-1H-indol-1-yl)-N-(2-fluorophenyl)azetidine-1-carboxamide

HPLC retention time (min.): 3.65; MS: 312 (M+H)$^+$.

EXAMPLE 3(759)

3-(2,3-Dihydro-1H-indol-1-yl)-N-[3-(trifluoromethyl)phenyl]azetidine-1-carboxamide HPLC retention time (min.): 3.90; MS: 723 (2M+H)$^+$, 362 (M+H)$^+$.

EXAMPLE 3(760)

N-Cyclopentyl-3-(2,3-dihydro-1H-indol-1-yl)azetidine-1-carboxamide

HPLC retention time (min.): 3.55; MS: 571 (2M+H)$^+$, 286 (M+H)$^+$.

EXAMPLE 3(761)

3-(2,3-Dihydro-1H-indol-1-yl)-N-(2,4-dimethylphenyl)azetidine-1-carboxamide

HPLC retention time (min.): 3.73; MS: 643 (2M+H)$^+$, 322 (M+H)$^+$.

EXAMPLE 3(762)

N-(3,5-Dichlorophenyl)-3-(2,3-dihydro-1H-indol-1-yl)azetidine-1-carboxamide

HPLC retention time (min.): 4.06; MS: 725, 723 (2M+H)$^+$, 364, 362 (M+H)$^+$.

EXAMPLE 3(763)

N-[3,5-Bis(trifluoromethyl)phenyl]-3-(2,3-dihydro-1H-indol-1-yl)azetidine-1-carboxamide HPLC retention time (min.): 4.16; MS: 430 (M+H)$^+$.

EXAMPLE 3(764)

3-(2,3-Dihydro-1H-indol-1-yl)-N-(3-phenoxyphenyl)azetidine-1-carboxamide

HPLC retention time (min.): 4.00; MS: 771 (2M+H)$^+$, 386 (M+H)$^+$.

EXAMPLE 3(765)

N-(3,5-Difluorophenyl)-3-(2,3-dihydro-1H-indol-1-yl)azetidine-1-carboxamide

HPLC retention time (min.): 3.83; MS: 330 (M+H)$^+$.

EXAMPLE 3(766)

3-(2,3-Dihydro-1H-indol-1-yl)-N-(4-methoxyphenyl)azetidine-1-carboxamide

HPLC retention time (min.): 3.59; MS: 647 (2M+H)$^+$, 324 (M+H)$^+$.

EXAMPLE 3(767)

3-(2,3-dihydro-1H-indol-1-yl)-N-(3,5-dimethylphenyl)azetidine-1-carboxamide

HPLC retention time (min.): 3.84; MS: 643 (2M+H)$^+$, 322 (M+H)$^+$.

EXAMPLE 3(768)

3-(2,3-Dihydro-1H-indol-1-yl)-N-(3-fluorophenyl)azetidine-1-carboxamide

HPLC retention time (min.): 3.73; MS: 623 (2M+H)$^+$, 312 (M+H)$^+$.

EXAMPLE 3(769)

Methyl 3-({[3-(2,3-dihydro-1H-indol-1-yl)azetidin-1-yl]carbonyl}amino)benzoate

HPLC retention time (min.): 3.68; MS: 703 (2M+H)$^+$, 352 (M+H)$^+$.

EXAMPLE 3(770)

3-(2,3-Dihydro-1H-indol-1-yl)-N-[3-(methylsulfanyl)phenyl]azetidine-1-carboxamide HPLC retention time (min.): 3.79; MS: 679 (2M+H)$^+$, 340 (M+H)$^+$.

EXAMPLE 3(771)

3-(2,3-Dihydro-1H-indol-1-yl)-N-(2-methylphenyl)azetidine-1-carboxamide

HPLC retention time (min.): 3.64; MS: 615 (2M+H)$^+$, 308 (M+H)$^+$.

EXAMPLE 3(772)

3-(3,4-Dihydroquinolin-1(2H)-yl)-N-propylazetidine-1-carboxamide

HPLC retention time (min.): 3.50; MS: 274 (M+H)$^+$.

EXAMPLE 3(773)

Ethyl N-{[3-(3,4-dihydroquinolin-1(2H)-yl)azetidin-1-yl]carbonyl}glycinate

HPLC retention time (min.): 3.42; MS: 318 (M+H)$^+$.

EXAMPLE 3(774)

3-(3,4-Dihydroquinolin-1(2H)-yl)-N-hexylazetidine-1-carboxamide

HPLC retention time (min.): 3.94; MS: 631 (2M+H)$^+$, 316 (M+H)$^+$.

EXAMPLE 3(775)

3-(3,4-Dihydroquinolin-1(2H)-yl)-N-(4-fluorophenyl)azetidine-1-carboxamide

HPLC retention time (min.): 3.78; MS: 326 (M+H)$^+$.

EXAMPLE 3(776)

3-(3,4-Dihydroquinolin-1(2H)-yl)-N-(3-methylphenyl)azetidine-1-carboxamide

HPLC retention time (min.): 3.86; MS: 643 (2M+H)$^+$, 322 (M+H)$^+$.

EXAMPLE 3(777)

3-(3,4-Dihydroquinolin-1(2H)-yl)-N-(2-thien-2-yl-ethyl)azetidine-1-carboxamide

HPLC retention time (min.): 3.73; MS: 683 (2M+H)$^+$, 342 (M+H)$^+$.

EXAMPLE 3(778)

3-(3,4-Dihydroquinolin-1(2H)-yl)-N-(4-isopropylphenyl)azetidine-1-carboxamide

HPLC retention time (min.): 4.04; MS: 699 (2M+H)$^+$, 350 (M+H)$^+$.

EXAMPLE 3(779)

N-(3-Chlorophenyl)-3-(3,4-dihydroquinolin-1(2H)-yl)azetidine-1-carboxamide

HPLC retention time (min.): 3.95; MS: 683 (2M+H)$^+$, 344, 342 (M+H)$^+$.

EXAMPLE 3(780)

3-(3,4-Dihydroquinolin-1(2H)-yl)-N-(2,5-dimethylphenyl)azetidine-1-carboxamide

HPLC retention time (min.): 3.86; MS: 671 (2M+H)$^+$, 336 (M+H)$^+$.

EXAMPLE 3(781)

N-(4-Chlorophenyl)-3-(3,4-dihydroquinolin-1(2H)-yl)azetidine-1-carboxamide

HPLC retention time (min.): 3.92; MS: 683 (2M+H)$^+$, 344, 342 (M+H)$^+$.

EXAMPLE 3(782)

N-Benzyl-3-(3,4-dihydroquinolin-1(2H)-yl)azetidine-1-carboxamide

HPLC retention time (min.): 3.71; MS: 643 (2M+H)$^+$, 322 (M+H)$^+$.

EXAMPLE 3(783)

3-(3,4-Dihydroquinolin-1(2H)-yl)-N-(1-naphthyl)azetidine-1-carboxamide

HPLC retention time (min.): 3.87; MS: 715 (2M+H)$^+$, 358 (M+H)$^+$.

EXAMPLE 3(784)

3-(3,4-Dihydroquinolin-1(2H)-yl)-N-(2-naphthyl)azetidine-1-carboxamide

HPLC retention time (min.): 3.98; MS: 715 (2M+H)$^+$, 358 (M+H)$^+$.

EXAMPLE 3(785)

3-(3,4-Dihydroquinolin-1(2H)-yl)-N-[1-(1-naphthyl)ethyl]azetidine-1-carboxamide

HPLC retention time (min.): 3.98; MS: 771 (2M+H)$^+$, 386 (M+H)$^+$, 232.

EXAMPLE 3(786)

3-(3,4-Dihydroquinolin-1(2H)-yl)-N-(3,4-dimethylphenyl)azetidine-1-carboxamide

HPLC retention time (min.): 3.92; MS: 671 (2M+H) +, 336 (M+H)$^+$.

EXAMPLE 3(787)

3-(3,4-Dihydroquinolin-1(2H)-yl)-N-(4-methylphenyl)azetidine-1-carboxamide

HPLC retention time (min.): 3.84; MS: 643 (2M+H)$^+$, 322 (M+H)$^+$.

EXAMPLE 3(788)

N-Cyclohexyl-3-(3,4-dihydroquinolin-1(2H)-yl)azetidine-1-carboxamide

HPLC retention time (min.): 3.77; MS: 627 (2M+H)$^+$, 314 (M+H)$^+$.

EXAMPLE 3(789)

3-(3,4-Dihydroquinolin-1(2H)-yl)-N-(2,6-dimethylphenyl)azetidine-1-carboxamide

HPLC retention time (min.): 3.76; MS: 671 (2M+H)$^+$, 336 (M+H)$^+$.

EXAMPLE 3(790)

3-(3,4-Dihydroquinolin-1(2H)-yl)-N-(2-ethoxyphenyl)azetidine-1-carboxamide

HPLC retention time (min.): 4.02; MS: 703 (2M+H)$^+$, 352 (M+H)$^+$.

EXAMPLE 3(791)

3-(3,4-Dihydroquinolin-1(2H)-yl)-N-(2-ethylphenyl)azetidine-1-carboxamide

HPLC retention time (min.): 3.86; MS: 671 (2M+H)$^+$, 336 (M+H)$^+$.

EXAMPLE 3(792)

3-(3,4-Dihydroquinolin-1(2H)-yl)-N-(4-ethoxyphenyl)azetidine-1-carboxamide

HPLC retention time (min.): 3.81; MS: 703 (2M+H)$^+$, 352 (M+H)$^+$.

EXAMPLE 3(793)

3-(3,4-Dihydroquinolin-1(2H)-yl)-N-(2-phenylethyl)azetidine-1-carboxamide

HPLC retention time (min.): 3.77; MS: 671 (2M+H)$^+$, 336 (M+H)$^+$.

EXAMPLE 3(794)

3-(3,4-Dihydroquinolin-1(2H)-yl)-N-phenylazetidine-1-carboxamide

HPLC retention time (min.): 3.75; MS: 615 (2M+H)$^+$, 308 (M+H)$^+$.

EXAMPLE 3(795)

N-(2-Chlorophenyl)-3-(3,4-dihydroquinolin-1(2H)-yl)azetidine-1-carboxamide

HPLC retention time (min.): 3.96; MS: 344, 342 (M+H)$^+$.

EXAMPLE 3(796)

3-(3,4-Dihydroquinolin-1(2H)-yl)-N-(2-fluorophenyl)azetidine-1-carboxamide

HPLC retention time (min.): 3.79; MS: 326 (M+H)$^+$.

EXAMPLE 3(797)

3-(3,4-Dihydroquinolin-1(2H)-yl)-N-[3-(trifluoromethyl)phenyl]azetidine-1-carboxamide HPLC retention time (min.): 4.02; MS: 751 (2M+H)$^+$, 376 (M+H)$^+$.

EXAMPLE 3(798)

N-Cyclopentyl-3-(3,4-dihydroquinolin-1(2H)-yl)azetidine-1-carboxamide

HPLC retention time (min.): 3.67; MS: 599 (2M+H)$^+$, 300 (M+H)$^+$.

EXAMPLE 3(799)

3-(3,4-Dihydroquinolin-1(2H)-yl)-N-(2,4-dimethylphenyl)azetidine-1-carboxamide

HPLC retention time (min.): 3.86; MS: 671 (2M+H)$^+$, 336 (M+H)$^+$.

EXAMPLE 3(800)

N-(3,5-Dichlorophenyl)-3-(3,4-dihydroquinolin-1(2H)-yl)azetidine-1-carboxamide

HPLC retention time (min.): 4.17; MS: 753, 751 (2M+H)$^+$, 378, 376 (M+H)$^+$.

EXAMPLE 3(801)

N-[3,5-Bis(trifluoromethyl)phenyl]-3-(3,4-dihydroquinolin-1(2H)-yl)azetidine-1-carboxamide HPLC retention time (min.): 4.26; MS: 444 (M+H)$^+$.

EXAMPLE 3(802)

3-(3,4-Dihydroquinolin-1(2H)-yl)-N-(3-phenoxyphenyl)azetidine-1-carboxamide

HPLC retention time (min.): 4.11; MS: 799 (2M+H)$^+$, 400 (M+H)$^+$.

EXAMPLE 3(803)

N-(3,5-Difluorophenyl)-3-(3,4-dihydroquinolin-1(2H)-yl)azetidine-1-carboxamide

HPLC retention time (min.): 3.95; MS: 344 (M+H)$^+$.

EXAMPLE 3(804)

3-(3,4-Dihydroquinolin-1(2H)-yl)-N-(4-methoxyphenyl)azetidine-1-carboxamide

HPLC retention time (min.): 3.69; MS: 675 (2M+H)$^+$, 338 (M+H)$^+$.

EXAMPLE 3(805)

3-(3,4-Dihydroquinolin-1(2H)-yl)-N-(3,5-dimethylphenyl)azetidine-1-carboxamide

HPLC retention time (min.): 3.95; MS: 671 (2M+H)$^+$, 336 (M+H)$^+$.

EXAMPLE 3(806)

3-(3,4-Dihydroquinolin-1(2H)-yl)-N-(3-fluorophenyl)azetidine-1-carboxamide

HPLC retention time (min.): 3.85; MS: 326 (M+H)$^+$.

EXAMPLE 3(807)

Methyl 3-({[3-(3,4-dihydroquinolin-1(2H)-yl)azetidin-1-yl]carbonyl}amino)benzoate HPLC retention time (min.): 3.80; MS: 731 (2M+H)$^+$, 366 (M+H)$^+$.

EXAMPLE 3(808)

3-(3,4-Dihydroquinolin-1(2H)-yl)-N-[3-(methylsulfanyl)phenyl]azetidine-1-carboxamide HPLC retention time (min.): 3.90; MS: 707 (2M+H)$^+$, 354 (M+H)$^+$.

EXAMPLE 3(809)

3-(3,4-Dihydroquinolin-1(2H)-yl)-N-(2-methylphenyl)azetidine-1-carboxamide

HPLC retention time (min.): 3.76; MS: 643 (2M+H)$^+$, 322 (M+H)$^+$.

EXAMPLE 4

N-[3,5-Bis(trifluoromethyl)phenyl]-3-piperazin-1-ylazetidine-1-carboxamide

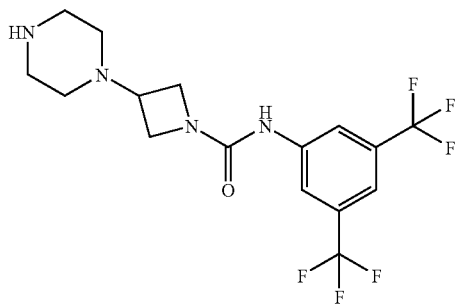

To a solution of the compound, prepared in Example 3 (1.04 g), in dichloromethane (21 mL) was added 2,6-lutidine (0.49 mL) at room temperature. To the mixture was added trimethylsilyl triflate (0.57 mL) dropwise, and the mixture was stirred for 80 minutes. The reaction solution was diluted with dichloromethane and to the mixture were added water and 5N aqueous solution of sodium hydroxide and it was extracted with dichloromethane. To the organic layer was added methanol and the mixture was concentrated. The residue was purified by column chromatography on silica gel (chloroform:methanol:triethylamine=10:1:1→3:1:1). The obtained compound was washed with tert-butyl methyl ether and tert-butyl methyl ether/hexane, and dried to give the compound of the present invention (800 mg) having the following physical data.

TLC:Rf 0.21 (chloroform:methanol:triethylamine=5:1:1);

NMR(CD$_3$OD): δ 2.45 (m, 4H), 2.94 (m, 4H), 3.23 (m, 1H), 3.95 (dd, J=9.00, 5.00 Hz, 2H), 4.13 (t, J=9.00 Hz, 2H), 7.51 (s, 1H), 8.11 (s, 2H).

EXAMPLE 5

3-(4-Benzylpiperazin-1-yl)-N-[3,5-bis(trifluoromethyl)phenyl]azetidine-1-carboxamide

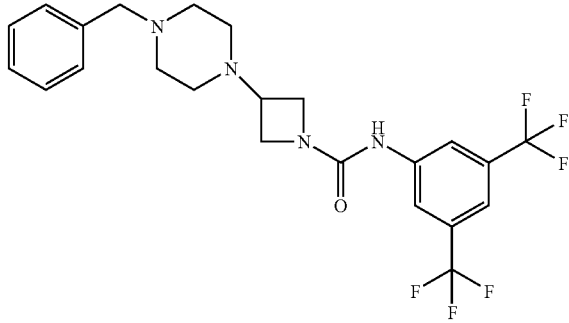

To a solution of the compound, prepared in Example 4 (20 mg), in tetrahydrofuran (0.25 mL) was added acetic acid (0.004 mL), and to the mixture was added 0.50 mol/L solution of benzaldehyde in dichloroethane (0.15 mL) at room temperature and the mixture was stirred for a while and it was allowed to stand for 30 minutes. To a solution of the compound, prepared in Example 4 (20 mg), in tetrahydrofuran (0.25 mL) was added acetic acid (0.004 mL), and then to the mixture was added a 0.50 mol/L solution of benzaldehyde in dichloroethane at room temperature, and the mixture was allowed to stand for 7.5 hours. To the reaction solution was added MP-triacetoxyborohydride (macroporous triethylammonium methyl polystyrene triacetoxyborohydride) (Argonote Technology Inc.; Cat. #.800415) (2.01 mmol/g, 75 mg) and it was shaken for a while and allowed to stand overnight. Thereto was added polystyrene sulfonylhydrazide (Argonote Technology Inc.; Cat. #.800272) (2.54 mmol/g, 59 mg) and tetrahydrofuran (0.35 mL), and the mixture was allowed to stand for 7.5 hours. The resin was filtered off and washed with tetrahydrofuran and concentrated. The obtained residue was purified by column chromatography on silica gel (hexane:ethyl acetate=1:2→ethyl acetate→ethyl acetate:methanol=20:1) to give the compound of the present invention (13 mg) having the following physical data.

TLC:Rf 0.42 (ethyl acetate:methanol=10:1);

NMR(CDCl$_3$):δ 2.50 (m, 8H), 3.26 (m, 1H), 3.54 (s, 2H), 3.98 (dd, J=8.00, 5.00 Hz, 2H), 4.09 (t, J=8.00 Hz, 2H), 6.22 (s, 1H), 7.29 (m, 5H), 7.50 (s, 1H), 7.90 (s, 2H).

EXAMPLES 5(1) to 5(122)

The following compounds of the present invention were prepared from an aldehyde derivative corresponding to benzaldehyde using a procedure analogous to that described for Example 5.

Example 5(1)

N-[3,5-Bis(trifluoromethyl)phenyl]-3-[4-(3-phenylpropyl)piperazin-1-yl]azetidine-1-carboxamide acetate

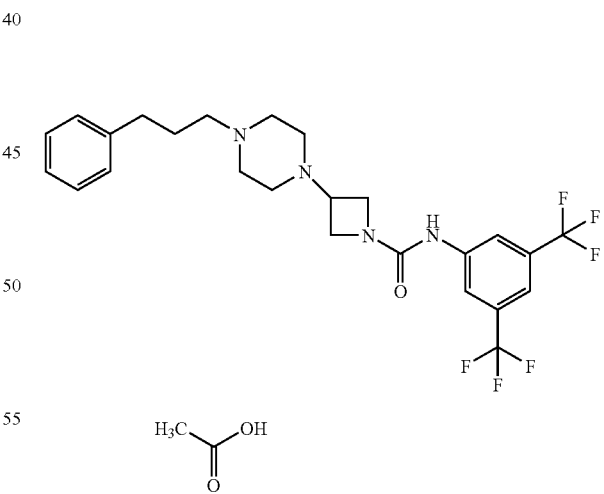

TLC:Rf 0.24 (ethyl acetate:methanol=10:1);

NMR(CDCl$_3$): δ 1.85 (m, 2H), 2.06 (s, 3H), 2.56 (m, 12H), 3.28 (m, 1H), 4.00 (dd, J=8.00, 5.50 Hz, 2H), 4.10 (t, J=8.00 Hz, 2H), 6.33 (s, 1H), 7.19 (m, 3H), 7.29 (m, 2H), 7.50 (s, 1H), 7.92 (s, 2H).

Example 5(2)

N-[3,5-Bis(trifluoromethyl)phenyl]-3-{4-[(1-methyl-1H-pyrrole-2-yl)methyl]piperazin-1-yl}azetidine-1-carboxamide
HPLC retention time (min.): 3.43; MS: 979 (2M+H)$^+$, 490 (M+H)$^+$.

Example 5(3)

N-[3,5-Bis(trifluoromethyl)phenyl]-3-{4-[(1,5-dimethyl-3-oxy-2-phenyl-2,3-dihydro-1H-pyrazole-4-yl)methyl]piperazin-1-yl}azetidine-1-carboxamide
HPLC retention time (min.): 3.38; MS: 597 (M+H)$^+$.

Example 5(4)

N-[3,5-Bis(trifluoromethyl)phenyl]-3-{4-[(5-methyl-2-furyl)methyl]piperazin-1-yl}azetidine-1-carboxamide
HPLC retention time (min.): 3.45; MS: 981 (2M+H)$^+$, 491 (M+H)$^+$.

Example 5(5)

[5-({4-[1-({[3,5-Bis(trifluoromethyl)phenyl]amino}carbonyl)azetidine-3-yl]piperazin-1-yl}methyl)-2-furyl]methyl acetate
HPLC retention time (min.): 3.42; MS: 549 (M+H)$^+$.

Example 5(6)

N-[3,5-Bis(trifluoromethyl)phenyl]-3-(4-{[5-(hydroxymethyl)-2-furyl]methyl}piperazin-1-yl)azetidine-1-carboxamide
HPLC retention time (min.): 3.31; MS: 507 (M+H)$^+$.

Example 5(7)

3-(4-Benzylpiperazin-1-yl)-N-[3,5-bis(trifluoromethyl)phenyl]azetidine-1-carboxamide
HPLC retention time (min.): 3.44; MS: 973 (2M+H)$^+$, 487 (M+H)$^+$.

Example 5(8)

N-[3,5-Bis(trifluoromethyl)phenyl]-3-[4-(2-methoxybenzyl)piperazin-1-yl]azetidine-1-carboxamide
HPLC retention time (min.): 3.45; MS: 517 (M+H)$^+$.

Example 5(9)

N-[3,5-Bis(trifluoromethyl)phenyl]-3-[4-(2,3-dimethoxybenzyl)piperazin-1-yl]azetidine-1-carboxamide
HPLC retention time (min.): 3.48; MS: 547 (M+H)$^+$.

Example 5(10)

N-[3,5-Bis(trifluoromethyl)phenyl]-3-[4-(2,4-dimethoxybenzyl)piperazin-1-yl]azetidine-1-carboxamide
HPLC retention time (min.): 3.49; MS: 547 (M+H)$^+$.

Example 5(11)

N-[3,5-Bis(trifluoromethyl)phenyl]-3-[4-(2,4,6-trimethoxybenzyl)piperazin-1-yl]azetidine-1-carboxamide
HPLC retention time (min.): 3.53; MS: 577 (M+H)$^+$, 181.

Example 5(12)

N-[3,5-Bis(trifluoromethyl)phenyl]-3-[4-(2,5-dimethoxybenzyl)piperazin-1-yl]azetidine-1-carboxamide
HPLC retention time (min.): 3.49; MS: 547 (M+H)$^+$.

Example 5(13)

[2-({4-[1-({[3,5-Bis(trifluoromethyl)phenyl]amino}carbonyl)azetidine-3-yl]piperazin-1-yl}methyl)phenoxy]acetic acid
HPLC retention time (min.): 3.42; MS: 561 (M+H)$^+$.

Example 5(14)

N-[3,5-Bis(trifluoromethyl)phenyl]-3-{4-[2-(trifluoromethyl)benzyl]piperazin-1-yl}azetidine-1-carboxamide
HPLC retention time (min.): 3.58; MS: 555 (M+H)$^+$.

Example 5(15)

N-[3,5-Bis(trifluoromethyl)phenyl]-3-[4-(2-methylbenzyl)piperazin-1-yl]azetidine-1-carboxamide
HPLC retention time (min.): 3.48; MS: 501 (M+H)$^+$.

Example 5(16)

N-[3,5-Bis(trifluoromethyl)phenyl]-3-[4-(3-cyanobenzyl)piperazin-1-yl]azetidine-1-carboxamide
HPLC retention time (min.): 3.45; MS: 512 (M+H)$^+$.

Example 5(17)

N-[3,5-Bis(trifluoromethyl)phenyl]-3-[4-(3-fluorobenzyl)piperazin-1-yl]azetidine-1-carboxamide
HPLC retention time (min.): 3.46; MS: 505 (M+H)$^+$.

Example 5(18)

N-[3,5-Bis(trifluoromethyl)phenyl]-3-[4-(3-fluoro-4-methoxybenzyl)piperazin-1-yl]azetidine-1-carboxamide
HPLC retention time (min.): 3.48; MS: 535 (M+H)$^+$.

Example 5(19)

N-[3,5-Bis(trifluoromethyl)phenyl]-3-[4-(3-phenoxybenzyl)piperazin-1-yl]azetidine-1-carboxamide
HPLC retention time (min.): 3.66; MS: 579 (M+H)$^+$.

Example 5(20)

N-[3,5-Bis(trifluoromethyl)phenyl]-3-[4-(3-methoxybenzyl)piperazin-1-yl]azetidine-1-carboxamide
HPLC retention time (min.): 3.46; MS: 517 (M+H)$^+$.

Example 5(21)

N-[3,5-Bis(trifluoromethyl)phenyl]-3-[4-(3,4-dimethoxybenzyl)piperazin-1-yl]azetidine-1-carboxamide
HPLC retention time (min.): 3.41; MS: 547 (M+H)$^+$.

Example 5(22)

N-[3,5-Bis(trifluoromethyl)phenyl]-3-[4-(3,4,5-trimethoxybenzyl)piperazin-1-yl]azetidine-1-carboxamide
HPLC retention time (min.): 3.45; MS: 577 (M+H)$^+$, 181.

Example 5(23)

3-(4-[4-(Benzyloxy)-3-methoxybenzyl]piperazin-1-yl)-N-[3,5-bis(trifluoromethyl)phenyl]azetidine-1-carboxamide
HPLC retention time (min.): 3.63; MS: 623 (M+H)$^+$, 227.

Example 5(24)

3-{4-[3-(Benzyloxy)benzyl]piperazin-1-yl}-N-[3,5-bis(trifluoromethyl)phenyl]azetidine-1-carboxamide
HPLC retention time (min.): 3.68; MS: 593 (M+H)$^+$.

Example 5(25)

N-[3,5-Bis(trifluoromethyl)phenyl]-3-[4-(3-hydroxybenzyl)piperazin-1-yl]azetidine-1-carboxamide
HPLC retention time (min.): 3.38; MS: 503 (M+H)$^+$.

Example 5(26)

N-[3,5-Bis(trifluoromethyl)phenyl]-3-[4-(3-hydroxy-4-methoxybenzyl)piperazin-1-yl]azetidine-1-carboxamide
HPLC retention time (min.): 3.40; MS: 533 (M+H)$^+$.

Example 5(27)

N-[3,5-Bis(trifluoromethyl)phenyl]-3-{4-[3-(trifluoromethyl)benzyl]piperazin-1-yl}azetidine-1-carboxamide
HPLC retention time (min.): 3.57; MS: 555 (M+H)$^+$.

Example 5(28)

N-[3,5-Bis(trifluoromethyl)phenyl]-3-[4-(3-methylbenzyl)piperazin-1-yl]azetidine-1-carboxamide
HPLC retention time (min.): 3.51; MS: 501 (M+H)$^+$.

Example 5(29)

N-[3,5-Bis(trifluoromethyl)phenyl]-3-[4-(4-cyanobenzyl)piperazin-1-yl]azetidine-1-carboxamide
HPLC retention time (min.): 3.43; MS: 512 (M+H)$^+$.

Example 5(30)

N-[3,5-Bis(trifluoromethyl)phenyl]-3-[4-(4-fluorobenzyl)piperazin-1-yl]azetidine-1-carboxamide
HPLC retention time (min.): 3.46; MS: 505 (M+H)$^+$.

Example 5(31)

3-{4-[4-(Acetylamino)benzyl]piperazin-1-yl}-N-[3,5-bis(trifluoromethyl)phenyl]azetidine-1-carboxamide
HPLC retention time (min.): 3.35; MS: 544 (M+H)$^+$.

Example 5(32)

N-[3,5-Bis(trifluoromethyl)phenyl]-3-{4-[4-(dimethylamino)benzyl]piperazin-1-yl}azetidine-1-carboxamide
HPLC retention time (min.): 3.29; MS: 530 (M+H)$^+$, 397, 134.

Example 5(33)

N-[3,5-Bis(trifluoromethyl)phenyl]-3-{4-[4-(diethylamino)benzyl]piperazin-1-yl}azetidine-1-carboxamide
HPLC retention time (min.): 3.25; MS: 558 (M+H)$^+$, 469, 162.

Example 5(34)

N-[3,5-Bis(trifluoromethyl)phenyl]-3-[4-(4-phenoxybenzyl)piperazin-1-yl]azetidine-1-carboxamide
HPLC retention time (min.): 3.65; MS: 579 (M+H)$^+$.

Example 5(35)

N-[3,5-Bis(trifluoromethyl)phenyl]-3-[4-(4-methoxybenzyl)piperazin-1-yl]azetidine-1-carboxamide
HPLC retention time (min.): 3.47; MS: 517 (M+H)$^+$.

Example 5(36)

3-{4-[4-(Benzyloxy)benzyl]piperazin-1-yl}-N-[3,5-bis(trifluoromethyl)phenyl]azetidine-1-carboxamide
HPLC retention time (min.): 3.67; MS: 593 (M+H)$^+$.

Example 5(37)

N-[3,5-Bis(trifluoromethyl)phenyl]-3-[4-(1H-imidazol-2-ylmethyl)piperazin-1-yl]azetidine-1-carboxamide
HPLC retention time (min.): 3.18; MS: 953 (2M+H)$^+$, 477 (M+H)$^+$.

Example 5(38)

N-[3,5-Bis(trifluoromethyl)phenyl]-3-[4-(1-naphthylmethyl)piperazin-1-yl]azetidine-1-carboxamide
HPLC retention time (min.): 3.55; MS: 537 (M+H)$^+$.

Example 5(39)

N-[3,5-Bis(trifluoromethyl)phenyl]-3-{4-[(4-methoxy-1-naphthyl)methyl]piperazin-1-yl}azetidine-1-carboxamide
HPLC retention time (min.): 3.59; MS: 567 (M+H)$^+$, 171.

Example 5(40)

3-{4-[3,4-Bis(benzyloxy)benzyl]piperazin-1-yl}-N-[3,5-bis(trifluoromethyl)phenyl]azetidine-1-carboxamide
HPLC retention time (min.): 3.83; MS: 699 (M+H)$^+$.

Example 5(41)

N-[3,5-Bis(trifluoromethyl)phenyl]-3-[4-(1H-pyrrole-2-ylmethyl)piperazin-1-yl]azetidine-1-carboxamide
HPLC retention time (min.): 3.38; MS: 951 (2M+H)$^+$, 476 (M+H)$^+$, 397.

Example 5(42)

N-[3,5-Bis(trifluoromethyl)phenyl]-3-[4-(thien-2-ylmethyl)piperazin-1-yl]azetidine-1-carboxamide
HPLC retention time (min.): 3.43; MS: 985 (2M+H)$^+$, 493 (M+H)$^+$.

Example 5(43)

N-[3,5-Bis(trifluoromethyl)phenyl]-3-{4-[(3-methylthien-2-yl)methyl]piperazin-1-yl}azetidine-1-carboxamide
HPLC retention time (min.): 3.47; MS: 507 (M+H)$^+$.

Example 5(44)

N-[3,5-Bis(trifluoromethyl)phenyl]-3-{4-[(4-bromothien-2-yl)methyl]piperazin-1-yl}azetidine-1-carboxamide HPLC retention time (min.): 3.51; MS: 573, 571 (M+H)+.

Example 5(45)

N-[3,5-Bis(trifluoromethyl)phenyl]-3-{4-[(5-bromothien-2-yl)methyl]piperazin-1-yl}azetidine-1-carboxamide HPLC retention time (min.): 3.53; MS: 573, 571 (M+H)+.

Example 5(46)

N-[3,5-Bis(trifluoromethyl)phenyl]-3-[4-(1H-indol-3-ylmethyl)piperazin-1-yl]azetidine-1-carboxamide HPLC retention time (min.): 3.49; MS: 526 (M+H)+, 397.

Example 5(47)

N-[3,5-Bis(trifluoromethyl)phenyl]-3-[4-(pyridin-4-ylmethyl)piperazin-1-yl]azetidine-1-carboxamide HPLC retention time (min.): 3.18; MS: 975 (2M+H)+, 488 (M+H)+.

Example 5(48)

N-[3,5-Bis(trifluoromethyl)phenyl]-3-[4-(4-hydroxybenzyl)piperazin-1-yl]azetidine-1-carboxamide HPLC retention time (min.): 3.38; MS: 503 (M+H)+.

Example 5(49)

3-[4-(1,1'-Biphenyl-4-ylmethyl)piperazin-1-yl]-N-[3,5-bis(trifluoromethyl)phenyl]azetidine-1-carboxamide HPLC retention time (min.): 3.63; MS: 563 (M+H)+.

Example 5(50)

Methyl 4-({4-[1-({[3,5-bis(trifluoromethyl)phenyl]amino}carbonyl)azetidine-3-yl]piperazin-1-yl}methyl)benzoate HPLC retention time (min.): 3.45; MS: 545 (M+H)+.

Example 5(51)

4-({4-[1-({[3,5-Bis(trifluoromethyl)phenyl]amino}carbonyl)azetidine-3-yl]piperazin-1-yl}methyl)benzoate HPLC retention time (min.): 3.38; MS: 531 (M+H)+.

Example 5(52)

N-[3,5-Bis(trifluoromethyl)phenyl]-3-{4-[4-(trifluoromethyl)benzyl]piperazin-1-yl}azetidine-1-carboxamide HPLC retention time (min.): 3.57; MS: 555 (M+H)+.

Example 5(53)

N-[3,5-Bis(trifluoromethyl)phenyl]-3-[4-(4-methylbenzyl)piperazin-1-yl]azetidine-1-carboxamide HPLC retention time (min.): 3.50; MS: 501 (M+H)+.

Example 5(54)

{4-[1-({[3,5-Bis(trifluoromethyl)phenyl]amino}carbonyl)azetidine-3-yl]piperazin-1-yl}acetic acid HPLC retention time (min.): 3.28; MS: 909 (2M+H)+, 455 (M+H)+.

Example 5(55)

N-[3,5-Bis(trifluoromethyl)phenyl]-3-{4-[(2E)-2-methylbut-2-enyl]piperazin-1-yl}azetidine-1-carboxamide HPLC retention time (min.): 3.42; MS: 929 (2M+H)+, 465 (M+H)+.

Example 5(56)

N-[3,5-Bis(trifluoromethyl)phenyl]-3-(4-isobutylpiperazin-1-yl)azetidine-1-carboxamide HPLC retention time (min.): 3.37; MS: 905 (2M+H)+, 453 (M+H)+.

Example 5(57)

N-[3,5-Bis(trifluoromethyl)phenyl]-3-[4-(2-ethylhexyl)piperazin-1-yl]azetidine-1-carboxamide HPLC retention time (min.): 3.61; MS: 509 (M+H)+.

Example 5(58)

N-[3,5-Bis(trifluoromethyl)phenyl]-3-(4-{(2E)-3-[4-(dimethylamino)phenyl]prop-2-enyl}piperazin-1-yl)azetidine-1-carboxamide HPLC retention time (min.): 3.28; MS: 556 (M+H)+, 397, 160.

Example 5(59)

N-[3,5-Bis(trifluoromethyl)phenyl]-3-(4-isopentylpiperazin-1-yl)azetidine-1-carboxamide HPLC retention time (min.): 3.43; MS: 933 (2M+H)+, 467 (M+H)+.

Example 5(60)

N-[3,5-Bis(trifluoromethyl)phenyl]-3-(4-propylpiperazin-1-yl)azetidine-1-carboxamide HPLC retention time (min.): 3.33; MS: 877 (2M+H)+, 439 (M+H)+.

Example 5(61)

N-[3,5-Bis(trifluoromethyl)phenyl]-3-{4-[3-(methylsulfanyl)propyl]piperazin-1-yl}azetidine-1-carboxamide HPLC retention time (min.): 3.39; MS: 969 (2M+H)+, 485 (M+H)+.

Example 5(62)

N-[3,5-Bis(trifluoromethyl)phenyl]-3-(4-butylpiperazin-1-yl)azetidine-1-carboxamide HPLC retention time (min.): 3.40; MS: 905 (2M+H)+, 453 (M+H)+.

Example 5(63)

N-[3,5-Bis(trifluoromethyl)phenyl]-3-[4-(quinolin-2-ylmethyl)piperazin-1-yl]azetidine-1-carboxamide HPLC retention time (min.): 3.33; MS: 538 (M+H)+.

Example 5(64)

N-[3,5-Bis(trifluoromethyl)phenyl]-3-[4-(3-nitrobenzyl)piperazin-1-yl]azetidine-1-carboxamide
HPLC retention time (min.): 3.48; MS: 532 (M+H)$^+$.

Example 5(65)

N-[3,5-Bis(trifluoromethyl)phenyl]-3-[4-(3,5-di-tert-butyl--4-hydroxybenzyl)piperazin-1-yl]azetidine-1-carboxamide
HPLC retention time (min.): 3.79; MS: 615 (M+H)$^+$.

Example 5(66)

N-[3,5-Bis(trifluoromethyl)phenyl]-3-[4-(2,3-dihydro-1,4-benzodioxin-6-ylmethyl)piperazin-1-yl]azetidine-1-carboxamide
HPLC retention time (min.): 3.46; MS: 545 (M+H)$^+$.

Example 5(67)

N-[3,5-Bis(trifluoromethyl)phenyl]-3-[4-(3-furylmethyl)piperazin-1-yl]azetidine-1-carboxamide
HPLC retention time (min.): 3.38; MS: 953 (2M+H)$^+$, 477 (M+H)$^+$.

Example 5(68)

4-{4-[1-({[3,5-Bis(trifluoromethyl)phenyl]amino}carbonyl)azetidine-3-yl]piperazin-1-yl}butanoic acid
HPLC retention time (min.): 3.26; MS: 483 (M+H)$^+$, 397.

Example 5(69)

N-[3,5-Bis(trifluoromethyl)phenyl]-3-[4-(2,6-dimethoxybenzyl)piperazin-1-yl]azetidine-1-carboxamide
HPLC retention time (min.): 3.51; MS: 547 (M+H)$^+$.

Example 5(70)

N-[3,5-Bis(trifluoromethyl)phenyl]-3-(4-{4-[3-(dimethylamino)propoxy]benzyl}piperazin-1-yl)azetidine-1-carboxamide
HPLC retention time (min.): 3.26; MS: 588 (M+H)$^+$.

Example 5(71)

N-[3,5-Bis(trifluoromethyl)phenyl]-3-{4-[(2-methyl-1H-indol-3-yl)methyl]piperazin-1-yl}azetidine-1-carboxamide
HPLC retention time (min.): 3.52; MS: 540 (M+H)$^+$, 397, 144.

Example 5(72)

N-[3,5-Bis(trifluoromethyl)phenyl]-3-[4-(cyclopropylmethyl)piperazin-1-yl]azetidine-1-carboxamide
HPLC retention time (min.): 3.36; MS: 901 (2M+H)$^+$, 451 (M+H)$^+$.

Example 5(73)

3-{4-[4-(Allyloxy)benzyl]piperazin-1-yl}-N-[3,5-bis(trifluoromethyl)phenyl]azetidine-1-carboxamide
HPLC retention time (min.): 3.55; MS: 543 (M+H)$^+$.

Example 5(74)

N-[3,5-Bis(trifluoromethyl)phenyl]-3-{4-[4-(octyloxy)benzyl]piperazin-1-yl}azetidine-1-carboxamide
HPLC retention time (min.): 4.01; MS: 615 (M+H)$^+$.

Example 5(75)

N-[3,5-Bis(trifluoromethyl)phenyl]-3-{4-[(1-methyl-1H-indol-3-yl)methyl]piperazin-1-yl}azetidine-1-carboxamide
HPLC retention time (min.): 3.54; MS: 540 (M+H)$^+$, 144.

Example 5(76)

3-[4-(1-Benzofuran-2-ylmethyl)piperazin-1-yl]-N-[3,5-bis(trifluoromethyl)phenyl]azetidine-1-carboxamide
HPLC retention time (min.): 3.54; MS: 527 (M+H)$^+$.

Example 5(77)

N-[3,5-Bis(trifluoromethyl)phenyl]-3-[4-(4-pyrrolidin-1-ylbenzyl)piperazin-1-yl]azetidine-1-carboxamide
HPLC retention time (min.): 3.57; MS: 556 (M+H)$^+$, 160.

Example 5(78)

3-{4-[2-(Benzyloxy)benzyl]piperazin-1-yl}-N-[3,5-bis(trifluoromethyl)phenyl]azetidine-1-carboxamide
HPLC retention time (min.): 3.67; MS: 593 (M+H)$^+$.

Example 5(79)

N-[3,5-Bis(trifluoromethyl)phenyl]-3-{4-[4-(heptyloxy)benzyl]piperazin-1-yl}azetidine-1-carboxamide
HPLC retention time (min.): 3.91; MS: 601 (M+H)$^+$.

Example 5(80)

3-[4-(1,3-Benzodioxol-4-ylmethyl)piperazin-1-yl]-N-[3,5-bis(trifluoromethyl)phenyl]azetidine-1-carboxamide

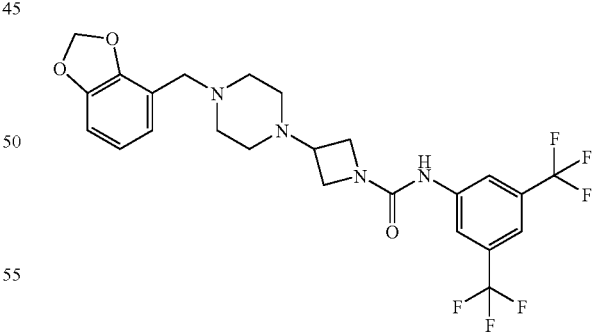

HPLC retention time (min.): 3.46; MS: 531 (M+H)$^+$.

Example 5(81)

N-[3,5-Bis(trifluoromethyl)phenyl]-3-{4-[(3,5,6-trimethylcyclohex-3-en-1-yl)methyl]piperazin-1-yl}azetidine-1-carboxamide
HPLC retention time (min.): 3.62; MS: 533 (M+H)$^+$.

Example 5(82)

N-[3,5-Bis(trifluoromethyl)phenyl]-3-{4-[4-(hexyloxy)-3-methoxybenzyl]piperazin-1-yl}azetidine-1-carboxamide
HPLC retention time (min.): 3.79; MS: 617 (M+H)+, 221.

Example 5(83)

N-[3,5-Bis(trifluoromethyl)phenyl]-3-{4-[(6-chloro-1,3-benzodioxol-5-yl)methyl]piperazin-1-yl}azetidine-1-carboxamide
HPLC retention time (min.): 3.51; MS: 567, 565 (M+H)+.

Example 5(84)

N-[3,5-Bis(trifluoromethyl)phenyl]-3-{4-[(5-ethyl-2-furyl)methyl]piperazin-1-yl}azetidine-1-carboxamide
HPLC retention time (min.): 3.51; MS: 505 (M+H)+.

Example 5(85)

N-[3,5-Bis(trifluoromethyl)phenyl]-3-[4-(4-tert-butylbenzyl)piperazin-1-yl]azetidine-1-carboxamide
HPLC retention time (min.): 3.66; MS: 543 (M+H)+.

Example 5(86)

N-[3,5-Bis(trifluoromethyl)phenyl]-3-[4-(3,7-dimethyloct-6-enyl)piperazin-1-yl]azetidine-1-carboxamide
HPLC retention time (min.): 3.71; MS: 535 (M+H)+.

Example 5(87)

N-[3,5-Bis(trifluoromethyl)phenyl]-3-{4-[2-(tert-butylsulfanyl)benzyl]piperazin-1-yl}azetidine-1-carboxamide
HPLC retention time (min.): 3.68; MS: 575 (M+H)+.

Example 5(88)

N-[3,5-Bis(trifluoromethyl)phenyl]-3-{4-[4-(trifluoromethoxy)benzyl]piperazin-1-yl}azetidine-1-carboxamide
HPLC retention time (min.): 3.59; MS: 571 (M+H)+.

Example 5(89)

N-[3,5-Bis(trifluoromethyl)phenyl]-3-{4-[(3,5-dimethyl-1-phenyl-1H-pyrazole-4-yl)methyl]piperazin-1-yl}azetidine-1-carboxamide
HPLC retention time (min.): 3.48; MS: 581 (M+H)+, 185.

Example 5(90)

N-[3,5-Bis(trifluoromethyl)phenyl]-3-(4-{2-[(4-chlorophenyl)sulfanyl]benzyl}piperazin-1-yl)azetidine-1-carboxamide
HPLC retention time (min.): 3.78; MS: 631, 629 (M+H)+.

Example 5(91)

N-[3,5-Bis(trifluoromethyl)phenyl]-3-{4-[(3-methyl-1-benzothien-2-yl)methyl]piperazin-1-yl}azetidine-1-carboxamide
HPLC retention time (min.): 3.61; MS: 557 (M+H)+.

Example 5(92)

N-[3,5-Bis(trifluoromethyl)phenyl]-3-{4-[(4-hydroxy-1-naphthyl)methyl]piperazin-1-yl}azetidine-1-carboxamide
HPLC retention time (min.): 3.50; MS: 553 (M+H)+, 397.

Example 5(93)

N-[3,5-Bis(trifluoromethyl)phenyl]-3-(4-{4-[2-(diethylamino)ethoxy]benzyl}piperazin-1-yl)azetidine-1-carboxamide
HPLC retention time (min.): 3.26; MS: 602 (M+H)+.

Example 5(94)

N-[3,5-Bis(trifluoromethyl)phenyl]-3-(4-{[(1R,5R)-6,6-dimethylbicyclo[3.1.1]hept-2-en-2-yl]methyl}piperazin-1-yl)azetidine-1-carboxamide

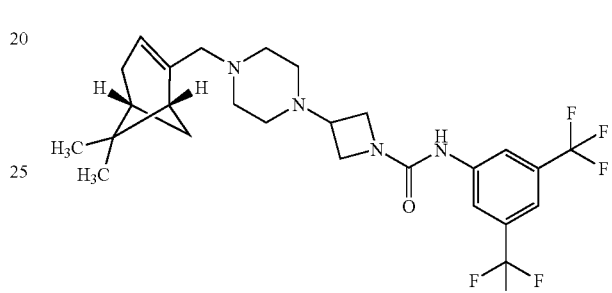

HPLC retention time (min.): 3.61; MS:531 (M+H)+.

Example 5(95)

N-[3,5-Bis(trifluoromethyl)phenyl]-3-{4-[(6-methoxy-2-naphthyl)methyl]piperazin-1-yl}azetidine-1-carboxamide
HPLC retention time (min.): 3.57; MS:567 (M+H)+, 171.

Example 5(96)

N-[3,5-Bis(trifluoromethyl)phenyl]-3-[4-({4-[(2E)-4-methylpent-2-enyl]cyclohex-3-en-1-yl}methyl)piperazin-1-yl]azetidine-1-carboxamide
HPLC retention time (min.): 3.79; MS:573 (M+H)+.

Example 5(97)

N-[3,5-Bis(trifluoromethyl)phenyl]-3-{4-[(5-chloro-3-methyl-1-phenyl-1H-pyrazol-4-yl)methyl]piperazin-1-yl}azetidine-1-carboxamide
HPLC retention time (min.): 3.54; MS:601 (M+H)+, 205.

Example 5(98)

N-[3,5-Bis(trifluoromethyl)phenyl]-3-{4-[(2-chloroquinolin-3-yl)methyl]piperazin-1-yl}azetidine-1-carboxamide
HPLC retention time (min.): 3.51; MS:574, 572 (M+H)+.

Example 5(99)

2-(Acetylamino)-1-{4-[1-({[3,5-bis(trifluoromethyl)phenyl]amino}carbonyl)azetidin-3-yl]piperazin-1-yl}-1,2-dideoxy-D-galactitol

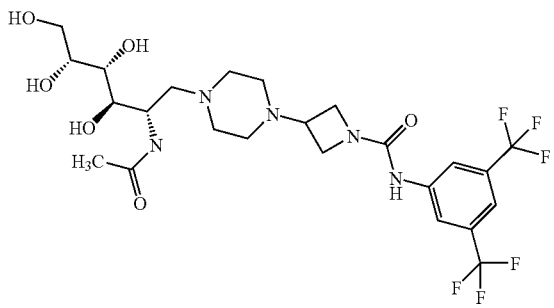

HPLC retention time (min.): 3.27; MS:793, 602 (M+H)+, 397.

Example 5(100)

5-{4-[1-({[3,5-Bis(trifluoromethyl)phenyl]amino}carbonyl)azetidin-3-yl]piperazin-1-yl}-4,5-dideoxy-D-erhthro-pentitol

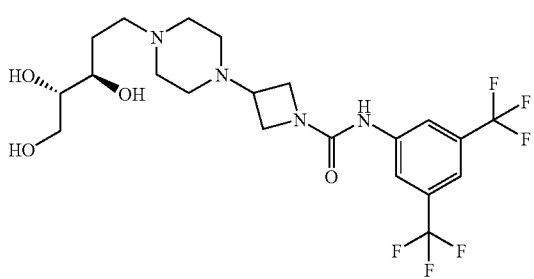

HPLC retention time (min.): 3.24; MS:515 (M+H)+.

Example 5(101)

N-[3,5-Bis(trifluoromethyl)phenyl]-3-(4-{[(3a'S,5'S,6'R,6a'S)-6'-hydroxytetrahydrospiro[cyclohexane-1,2'-furo[2,3-d][1,3]dioxol]-5'-yl]methyl}piperazin-1-yl)azetidine-1-carboxamide

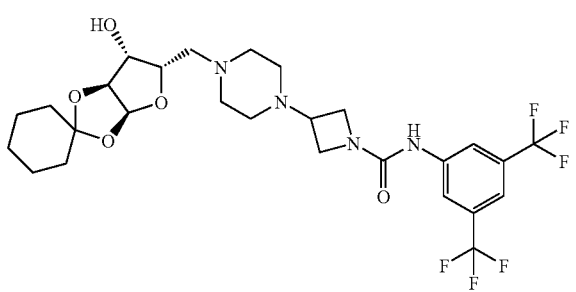

HPLC retention time (min.): 3.48; MS:609 (M+H)+.

Example 5(102)

N-[3,5-Bis(trifluoromethyl)phenyl]-3-[4-(1,3-thiazol-2-ylmethyl)piperazin-1-yl]azetidine-1-carboxamide HPLC retention time (min.): 3.34; MS:987 (2M+H)+, 494 (M+H)+.

Example 5(103)

N-[3,5-Bis(trifluoromethyl)phenyl]-3-{4-[(5-ethylthien-2-yl)methyl]piperazin-1-yl}azetidine-1-carboxamide HPLC retention time (min.): 3.55; MS:521 (M+H)+.

Example 5(104)

4-({4-[1-({[3,5-Bis(trifluoromethyl)phenyl]amino}carbonyl)azetidin-3-yl]piperazin-1-yl)methyl}phenylboronic acid HPLC retention time (min.): 3.39; MS:531 (M+H)+, 503.

Example 5(105)

N-[3,5-Bis(trifluoromethyl)phenyl]-3-{4-[(8-hydroxyquinolin-2-yl)methyl]piperazin-1-yl}azetidine-1-carboxamide HPLC retention time (min.): 3.42; MS:554 (M+H)+.

Example 5(106)

N-[3,5-Bis(trifluoromethyl)phenyl]-3-{4-[(4-methyl-1H-imidazol-5-yl)methyl]piperazin-1-yl}azetidine-1-carboxamide HPLC retention time (min.): 3.26; MS:981 (2M+H)+, 491 (M+H)+, 397.

Example 5(107)

N-[3,5-Bis(trifluoromethyl)phenyl]-3-{4-[(2-phenyl-1H-imidazol-4-yl)methyl]piperazin-1-yl}azetidine-1-carboxamide HPLC retention time (min.): 3.28; MS:553 (M+H)+.

Example 5(108)

N-[3,5-Bis(trifluoromethyl)phenyl]-3-[4-({5-[3,5-bis(trifluoromethyl)phenyl]-2-furyl}methyl)piperazin-1-yl]azetidine-1-carboxamide HPLC retention time (min.): 3.83; MS:689 (M+H)+.

Example 5(109)

Methyl 3-({4-[1-({[3,5-bis(trifluoromethyl)phenyl]amino}carbonyl)azetidin-3-yl]piperazin-1-yl}methyl)benzoate HPLC retention time (min.): 3.46; MS:545 (M+H)+.

Example 5(110)

N-[3,5-Bis(trifluoromethyl)phenyl]-3-{4-[(2,4-dioxo-1,2,3,4-tetrahydropyrimidin-5-yl)methyl]piperazin-1-yl}azetidine-1-carboxamide HPLC retention time (min.): 3.26; MS:521 (M+H)+, 397.

Example 5(111)

N-[3,5-Bis(trifluoromethyl)phenyl]-3-(4-{[5-(4-chlorophenyl)-2-furyl]methyl}piperazin-1-yl)azetidine-1-carboxamide HPLC retention time (min.): 3.70; MS:589, 587 (M+H)$^+$, 193, 191.

Example 5(112)

Methyl 2-({4-[1-({[3,5-bis(trifluoromethyl)phenyl]amino}carbonyl)azetidin-3-yl]piperazin-1-yl}methyl)benzoate HPLC retention time (min.): 3.46; MS:545 (M+H)$^+$.

Example 5(113)

N-[3,5-Bis(trifluoromethyl)phenyl]-3-{4-[3-(5-methyl-2-furyl)butyl]piperazin-1-yl}azetidine-1-carboxamide HPLC retention time (min.): 3.55; MS:533 (M+H)$^+$.

Example 5(114)

N-[3,5-Bis(trifluoromethyl)phenyl]-3-(4-{[5-(3-chlorophenyl)-2-furyl]methyl}piperazin-1-yl)azetidine-1-carboxamide HPLC retention time (min.): 3.69; MS:589, 587 (M+H)$^+$, 193, 191.

Example 5(115)

Methyl 3-({4-[1-({[3,5-bis(trifluoromethyl)phenyl]amino}carbonyl)azetidin-3-yl]piperazin-1-yl}methyl)-1-indole-6-carboxylate HPLC retention time (min.): 3.49; MS:584 (M+H)$^+$, 397, 188.

Example 5(116)

N-[3,5-Bis(trifluoromethyl)phenyl]-3-{4-[4-(methylsulfonyl)benzyl]piperazin-1-yl}azetidine-1-carboxamide HPLC retention time (min.): 3.38; MS:565 (M+H)$^+$.

Example 5(117)

N-[3,5-Bis(trifluoromethyl)phenyl]-3-(4-{[5-(2-chlorophenyl)-2-furyl]methyl}piperazin-1-yl)azetidine-1-carboxamide HPLC retention time (min.): 3.67; MS:589, 587 (M+H)$^+$, 193, 191.

Example 5(118)

N-[3,5-Bis(trifluoromethyl)phenyl]-3-{4-[(3-phenyl-1H-pyrazol-4-yl)methyl]piperazin-1-yl}azetidine-1-carboxamide HPLC retention time (min.): 3.43; MS:553 (M+H)$^+$.

Example 5(119)

N-[3,5-Bis(trifluoromethyl)phenyl]-3-[4-({5-[2-(trifluoromethyl)phenyl]-2-furyl}methyl)piperazin-1-yl]azetidine-1-carboxamide HPLC retention time (min.): 3.70; MS:621 (M+H)$^+$.

Example 5(120)

N-[3,5-Bis(trifluoromethyl)phenyl]-3-[4-({5-[3-(trifluoromethyl)phenyl]-2-furyl}methyl)piperazin-1-yl]azetidine-1-carboxamide HPLC retention time (min.): 3.72; MS:621 (M+H)$^+$, 225.

Example 5(121)

N-[3,5-Bis(trifluoromethyl)phenyl]-3-[4-({5-[2-chloro-5-(trifluoromethyl)phenyl]-2-furyl}methyl)piperazin-1-yl]azetidine-1-carboxamide HPLC retention time (min.): 3.78; MS:657, 655 (M+H)$^+$.

Example 5(122)

N-[3,5-Bis(trifluoromethyl)phenyl]-3-[4-({5-[2-(trifluoromethoxy)phenyl]-2-furyl}methyl)piperazin-1-yl]azetidine-1-carboxamide HPLC retention time (min.): 3.74; MS:637 (M+H)$^+$, 241.

BIOLOGICAL EXAMPLE

Evaluation of Antagonistic Activity for EDG-5 by Monitoring the Concentration Change of Intracellular Calcium Ion Chinese hamster ovary (CHO) cells in which human EDG-5 gene was overexpressed were cultured in Ham's F12 medium (GIBCO BRL) containing 10% FBS (fetal bovine serum), penicillin/streptomycin. and blasticidin (5 µg/mL). Thus cultured cells were incubated in a Fura2 (5 µM)-AM solution [Ham's F12 medium containing FBS (10%), HEPES buffer (20 mM, pH7.4), and probenecid (2.5 mM)] at 37° C. for 60 minutes. Then the cells were washed once with a Hanks' solution (2.5 mM) containing probenecid and immersed into the Hanks' solution. A plate was set on a fluorescent drug screening system, and the concentration of intracellular calcium ion was measured for 30 seconds with no stimulation. A solution of a compound (dimethyl sulfoxide (DMSO) solution of 1 nM to 10 µM at the final concentration) to be tested was added. After lapse of 5 minutes, S1P (final concentration: 100 nM) was added, the concentration of intracellular calcium ion before and after the addition of SiP was measured every 3 seconds (excitation wave length: 340 nm and 380 nm; fluorescent wave length: 500 nm).

The antagonisitc activity for EDG-5 was calculated as an inhibition rate (%) by the following equation, wherein the peak value of S1P (final concentration: 100 nM) in a well into which DMSO was added instead of the test compound was regarded as a control value (A), and in the cells treated with the compound the difference value (B) between the value before addition of the compound and that after the addition was obtained and compared with the control value.

Inhibition rate (%)=((A-B)/A)×100

IC$_{50}$ value was given as the concentration of the compound of the present invention at which it shows an inhibition rate of 50%. As a result, the compound of the present invention showed an antagonisitic activity against EDG-5. For example, the IC$_{50}$ value of the compound of Example 3(18) was 950 nM.

FORMULATION EXAMPLE 1

N-[3,5-bis(trifluoromethyl)phenyl]-3-[ethyl(phenyl)amino]azetidine-1-carboxamide (100 g), carboxymethylcellulose calcium (20.0 g), magnesium stearate (10.0 g) and microcrystalline cellulose (870 g) were admixed in a conventional method and it was punched out to give 10,000 tablets each containing 10 mg of active ingredient.

FORMULATION EXAMPLE 2

N-[3,5-bis(trifluoromethyl)phenyl]-3-[ethyl(phenyl)amino]azetidine-1-carboxamide (200 g), mannitol (2 kg) and distilled water (50 L) were admixed in a conventional method, and the mixture was filtrated over a dust removal filter. 5 ml of the solution was filled into each ampoule and the ampoules were heat-sterilized with an autoclave to give 10,000 ampoules each containing 20 mg of active ingredient.

INDUSTRIAL APPLICABILITY

Because of having EDG-5 antagonism, the compound of the present invention is useful as a preventive and/or therapeutic agent for, for example, diseases caused by blood vessel contraction (e.g. cerebrovascular spasms disease, cardiovascular spasms diseases, coronary artery spasms disease, hypertension, pulmonary hypertension, renal diseases, myocardial infarction, angina pectoris, arrhythmia, portal hypertension, varicosity and the like), arteriosclerosis, pulmonary fibrosis, hepatic fibrosis, renal fibrosis, respiratory diseases (e.g. bronchial asthma, chronic obstructive pulmonary diseases and the like), nephropathy, diabetes, hyperlipemia and the like. Therefore, the compound of the present invention. is applicable as a pharmaceutical.

The invention claimed is:

1. A compound of the formula (I):

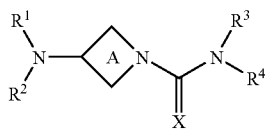

wherein
ring A is an azetidine ring,
X is oxygen,
$R^1$ and $R^2$ are each independently $C_{1-8}$ alkyl which may have substituent(s) or a benzene ring which may have substituent(s),
$R^3$ is hydrocarbon group which may have substituent(s),
$R^4$ is hydrogen,
$R^1$ and $R^2$ may be taken together with the adjacent nitrogen atom to form a piperidine, pyrrolidine, morpholine, piperazine, indoline, tetrahydroquinoline or tetrahydroisoquinoline ring group which may have further substituent(s), or
a salt thereof.

2. The compound according to claim 1, which is a compound of the formula (I-1):

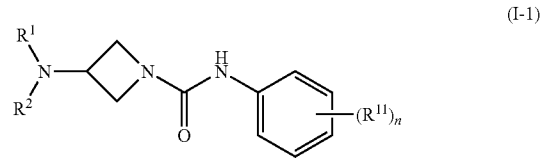

wherein
$R^1$ is a benzene ring which may have substituent(s),
$R^2$ is $C_{1-8}$ alkyl which may have substituent(s) or a benzene ring which may have substituent(s),
$R^{11}$ is substituent(s), and
n is 0 or an integer of 1-5, with the proviso that when n is 2 or more, the plural $R^{11}$s may be the same or different.

3. The compound according to claim 1 wherein $R^1$ and $R^2$ are taken together with the adjacent nitrogen atom to form a piperidine, pyrrolidine, morpholine, piperazine, indoline, tetrahydroquinoline and tetrahydroisoquinoline ring group which may further have substituent(s).

4. The compound according to claim 1, which is selected from the group consisting of N-(3,5-dichlorophenly)-3-(4-phenylpiperidin-1-yl)azetidine-1-carboxamide, 3-(2,3-dihydro-1H-indol-1-yl)-N-[3-(trifluoromethly)phenyl]azetidine-1-carboxamide, N-(3,5-dichlorophenyl)-3-(2,3-dihydro-1H-indol-1-yl)azetidine-1-carboxamied, N-[3,5-bis(trifluoromethyl)phenyl]-3-(2,3-dihydro-1H-indol-1-yl)azetidine-1-carboxamide, 3-(2,3-dihydro-1H-indol-1-yl)-N-(3-phenoxyphenyl)azetidine-1-carboxamide, N-[3,5-bis(trifloromethly)phenyl]-3-[methyl(phenyl)amino]azetidine-1-carboxamide and N-[3,5-bis(trifluoromethyl) phenyl]-3-[ethyl(phenyl)amino]azetidine-1-carboxamide.

5. A pharmaceutical composition comprising the compound of the formula (I), or a salt thereof described in claim 1, together with a pharmaceutically acceptable carrier.

* * * * *